US012623989B2

(12) United States Patent
Tulaphol et al.

(10) Patent No.: US 12,623,989 B2
(45) Date of Patent: May 12, 2026

(54) ONE-POT ACID-CATALYZED LEVULINIC ACID PRODUCTION FROM LIGNOCELLULOSIC BIOMASS

(71) Applicant: University of Louisville Research Foundation, Inc., Louisville, KY (US)

(72) Inventors: Sarttrawut Tulaphol, Nongyai Chonburi (TH); Noppadon Sathitsuksanoh, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 243 days.

(21) Appl. No.: 17/604,112

(22) PCT Filed: Apr. 16, 2020

(86) PCT No.: PCT/US2020/028553
§ 371 (c)(1),
(2) Date: Oct. 15, 2021

(87) PCT Pub. No.: WO2020/214835
PCT Pub. Date: Oct. 22, 2020

(65) Prior Publication Data
US 2022/0220055 A1     Jul. 14, 2022

Related U.S. Application Data

(60) Provisional application No. 62/834,775, filed on Apr. 16, 2019.

(51) Int. Cl.
| | |
|---|---|
| *C07C 51/00* | (2006.01) |
| *C07D 307/68* | (2006.01) |
| *C07H 1/08* | (2006.01) |
| *C07H 3/02* | (2006.01) |

(52) U.S. Cl.
CPC ............ *C07C 51/00* (2013.01); *C07D 307/68* (2013.01); *C07H 1/08* (2013.01); *C07H 3/02* (2013.01)

(58) Field of Classification Search
CPC ......... C07C 51/00; C07C 59/185; C07H 1/08; C07H 3/02; C07D 307/68
See application file for complete search history.

(56) References Cited

U.S. PATENT DOCUMENTS

| | | | |
|---|---|---|---|
| 5,608,105 | A | 3/1997 | Fitzpatrick |
| 5,916,780 | A | 6/1999 | Foody et al. |
| 8,663,392 | B2 | 3/2014 | Zhang |
| 9,346,730 | B2 | 5/2016 | De Vries et al. |
| 9,663,835 | B2 | 5/2017 | Zhang |
| 2012/0202272 | A1 | 8/2012 | Chatterjee et al. |
| 2014/0209261 | A1 | 7/2014 | Fougere et al. |
| 2014/0316161 | A1 | 10/2014 | Mullen et al. |
| 2015/0052806 | A1 | 2/2015 | Frey et al. |
| 2016/0176838 | A1 | 6/2016 | Sathitsuksanoh et al. |
| 2017/0183322 | A1 | 6/2017 | Pasanen |
| 2017/0190682 | A1 | 7/2017 | Retsina et al. |
| 2017/0191099 | A1 | 7/2017 | Mcdonald et al. |

FOREIGN PATENT DOCUMENTS

| | | |
|---|---|---|
| IN | 2016/31036686 A | 4/2018 |

OTHER PUBLICATIONS

Gandolfi, S.; et al. "Complete Chemical Analysis of Carmagnola Hemp Hurds and Structural Features of Its Components" 2013, BioResources, vol. 8, pp. 2641-2656. (Year: 2013).*

Binder, J.B.; Raines, R.T. "Fermentable sugars by chemical hydrolysis of biomass" 2010, Proceedings of the National Academies of Sciences, vol. 107, pp. 4516-4521. (Year: 2010).*

Peleteiro, S.; et al. "Furan manufacture from softwood hemicelluloses by aqueous fractionation and further reaction in a catalyzed ionic liquid: a biorefinery approach" 2014, Journal of Cleaner Production, vol. 76, pp. 200-203. (Year: 2014).*

Sathitsuksanoh, N.; et al. "Saccharification of a Potential Bioenergy Crop, *Phragmites australis* (Common Reed), by Lignocellulose Fractionation Followed by Enzymatic Hydrolysis at Decreased Cellulase Loadings" 2009, Ind. Eng. Chem. Res., vol. 48, pp. 6441-6447. (Year: 2009).*

Mirmohamadsadeghi, S.; et al. "Improvement of Solid-State Biogas Production from Wood by Concentrated Phosphoric Acid Pretreatment" 2016, BioResources, vol. 11, pp. 3230-3243. (Year: 2016).*

Hu, J.; et al. "The synergistic action of accessory enzymes enhances the hydrolytic potential of a "cellulase mixture" but is highly substrate specific" 2013, Biotechnology for Biofuels and Bioproducts, vol. 6, article No. 112 (Year: 2013).*

(Continued)

*Primary Examiner* — Andrea Olson
*Assistant Examiner* — Benjamin M Brandsen
(74) *Attorney, Agent, or Firm* — Hamilton, Brook, Smith & Reynolds, P.C.

(57) ABSTRACT

Provided are methods for producing levulinic acid from hemp hurds. In some embodiments, the methods include dissolving hemp hurds in an ionic liquid medium to produce a cellulose-rich product; hydrolyzing cellulose present in the cellulose-rich product to produce a glucose-rich product; dehydrating glucose present in the glucose-rich product, and/or fructose resulting from isomerization of the glucose, to produce 5-hydroxymethyl furfural (HMF); and hydrolyzing the HMF to levulinic acid. Also provided are methods for producing levulinic acid from sugar sources generally, which can include providing a sugar source, wherein the sugar source is a hydrolysis product produced by hydrolyzing a cellulose-rich product generated from hemp hurds and/or a cellulase digestion product of softwood pre-treated with phosphoric acid ($H_3PO_4$) or another acid; dehydrating the glucose present in the sugar source, and/or fructose resulting from isomerization of glucose present in the sugar source, to produce 5-hydroxymethyl furfural (HMF); and hydrolyzing the HMF to produce levulinic acid.

15 Claims, 18 Drawing Sheets

(56) References Cited

OTHER PUBLICATIONS

Rana, D.; et al. "Producing high sugar concentrations from loblolly pine using wet explosion pretreatment" 2012, Bioresource Technology, vol. 121, pp. 61-67 (Year: 2012).*

Qin, L.; et al. "Process analysis and optimization of simultaneous saccharification and co-fermentation of ethylenediamine-pretreated corn stover" 2018. Biotechnology for Biofuels and Bioproducts, vol. 11, article No. 118. (Year: 2018).*

Moxley, G.; et al. "Efficient Sugar Release by the Cellulose Solvent-Based Lignocellulose Fractionation Technology and Enzymatic Cellulose Hydrolysis" 2008, Journal of Agricultural and Food Chemistry, vol. 56, pp. 7885-7890. (Year: 2008).*

Gandolfi, S.; et al. "Fractionation of Hemp Hurds by Organosolv Pretreatment and its Effect on Production of Lignin and Sugars" 2014, ChemSusChem, vol. 7, pp. 1991-1999. (Year: 2014).*

International Search Report and Written Opinion corresponding to International Patent Application Serial No. PCT/US2020/028553 dated Jul. 22, 2020.

Paul et al. (2018) "Microwave-Assisted Ionic Liquid-Mediated Rapid Catalytic Conversion of Non-Edible Lignocellulosic Sunn Hemp Fibres to Biofuels," Bioresource Technology, vol. 253, pp. 85-93.

Funaoka. M. et al., "Condensation of lignin during heating of wood," Wood Science and Technology, vol. 24, 1990, pp. 277-288.

Abels. C. et al., "Simple purification of ionic liquid solvents by nanofiltration in biorefining of lignocellulosic substrates," Journal of Membrane Science, vol. 405, 2012, pp. 1-10.

Ahn. Y. et al., "Physical state of cellulose in BmimCI: dependence of molar mass on viscoelasticity and sol-gel transition," Physical Chemistry Chemical Physics, vol. 18, Issue 3, 2016, pp. 1460-1469.

Alonso. DM. et al, "Increasing the revenue from lignocellulosic biomass: Maximizing feedstock utilization," Science advances, vol. 3, Issue 5, 2017, e1603301, 7 pages.

Alvarez-Vasco. C. et al., "Alkaline hydrogen peroxide pretreatment of softwood: hemicellulose degradation pathways," Bioresource technology, vol. 150, 2013, pp. 321-327.

Alvarez. C. et al., "Enzymatic hydrolysis of biomass from wood," Microbial biotechnology, vol. 9, Issue 2, 2016, pp. 149-156.

Amarasekara. AS. et al., "Degradation of cellulose in dilute aqueous solutions of acidic ionic liquid 1-(1-propylsulfonic)-3-methylimidazolium chloride, and p-toluenesulfonic acid at moderate temperatures and pressures," Industrial & engineering chemistry research, vol. 50, Issue 21, 2011, pp. 12276-12280.

Amin. MI. et al., "Recovery of high grade phosphoric acid from wet process acid by solvent extraction with aliphatic alcohols," Hydrometallurgy, vol. 105, Issue 1-2, 2010, pp. 115-119.

Andre. CM. et al., "Cannabis sativa: The Plant of the Thousand and One Molecules," Frontiers in plant science, vol. 7, 2016, 17 pages.

Anwar. Z. et al., "Agro-industrial lignocellulosic biomass a key to unlock the future bio-energy: a brief review," Journal of radiation research and applied sciences, vol. 7, Issue 2, 2014, pp. 163-173.

Asdrubali., "Survey on the acoustical properties of new sustainable materials for noise control," Proceedings of Euronoise, vol. 30, 2006, 10 pages.

Ash. AL., "Hemp—production and utilization," Economic Botany, vol. 2, 1948, pp. 158-169.

Assuncao. MC. et al., "Phosphoric acid recovery from concentrated aqueous feeds by a mixture of di-isopropyl ether (DiPE) and tri-n-butylphosphate (TBP): extraction data and modelling," RSC Advances, vol. 7, Issue 12, 2017, pp. 6922-6930.

Barbera. L. et al., "Upgrading of hemp core for papermaking purposes by means of organosolv process," Industrial Crops and Products, vol. 34, Issue 1, 2011, pp. 865-872.

Barta. Z. et al., "Refining hemp hurds into fermentable sugars or ethanol," Chemical and biochemical engineering quarterly, vol. 24, Issue 3, 2010, pp. 331-339.

Binder. JB. et al., "Simple chemical transformation of lignocellulosic biomass into furans for fuels and chemicals," Journal of the American Chemical Society, vol. 131, Issue 5, 2009, pp. 1979-1985.

Biswas. R. et al., "Pretreatment of forest residues of Douglas fir by wet explosion for enhanced enzymatic saccharification," Bioresource technology, vol. 192, 2015, pp. 46-53.

Blanchard. LA. et al., "Recovery of organic products from ionic liquids using supercritical carbon dioxide," Industrial & engineering chemistry research, vol. 40, Issue 1, 2001, pp. 287-292.

Bozell. JJ. et al., "Production of levulinic acid and use as a platform chemical for derived products," Resources, conservation and recycling, vol. 28, Issue 3-4, 2000, pp. 227-239.

Braden. DJ. et al., "Production of liquid hydrocarbon fuels by catalytic conversion of biomass-derived levulinic acid," Green Chemistry, vol. 13, Issue 7, 2011, pp. 1755-1765.

Brandt. A. et al., "Structural changes in lignins isolated using an acidic ionic liquid water mixture," Green Chemistry, vol. 17, Issue 11, 2015, pp. 5019-5034.

Brouwer. T. et al., "Reactive extraction and recovery of levulinic acid, formic acid and furfural from aqueous solutions containing sulphuric acid," Separation and purification technology, vol. 185, 2017, pp. 186-195.

Brownleader, M. D., "Carbohydrate metabolism: primary metabolism of monosaccharides," Plant Phytochemistry, 1997, pp. 111-140.

Cao. Q et al., "Catalytic synthesis of 2, 5-bis-methoxymethylfuran: A promising cetane No. improver for diesel," Applied Catalysis A: General, vol. 481, 2014, pp. 49-53.

Cao. Y. et al., "Structure and properties of novel regenerated cellulose films prepared from cornhusk cellulose in room temperature ionic liquids," Journal of Applied Polymer Science, vol. 116, Issue 1, 2010, pp. 547-554.

Chakar. FS. et al., "Review of current and future softwood kraft lignin process chemistry," Industrial crops and products, vol. 20, Issue 2, 2004, pp. 131-141.

Chang. C. et al., "Levulinic acid production from wheat straw," Bioresource technology, vol. 98, Issue 7, 2007, pp. 1448-1453.

Chen. HZ. et al., "Regenerated cellulose membrane prepared with ionic liquid 1-butyl-3-methylimidazolium chloride as solvent using wheat straw," Journal of Chemical Technology & Biotechnology, vol. 87, Issue 12, 2012, pp. 1634-1640.

Chen. T. et al., "Enhanced hydrolysis of cellulose in ionic liquid using mesoporous ZSM-5," Molecules, vol. 23, Issue 3, 2018, 10 pages.

Cheng. K. et al., "Solution-state 2D NMR spectroscopy of plant cell walls enabled by a dimethylsulfoxide-d 6/1-ethyl-3-methylimidazolium acetate solvent," Analytical chemistry, vol. 85, Issue 6, 2013, pp. 3213-3221.

Chio. C. et al., "Lignin utilization: A review of lignin depolymerization from various aspects," Renewable and sustainable energy reviews, vol. 107, 2019, pp. 232-249.

Choudhary. V. et al., "Insights into the interplay of Lewis and Brønsted acid catalysts in glucose and fructose conversion to 5-(hydroxymethyl) furfural and levulinic acid in aqueous media," Journal of the American Chemical Society, vol. 135, Issue 10, 2013, pp. 3997-4006.

Christensen. E. et al., "Properties and performance of levulinate esters as diesel blend components," Energy & fuels, vol. 25, Issue 11, 2011, pp. 5422-5428.

Cleveland et al., "Climate Change. In Handbook of Energy," C. Section 45—Cleveland & Morris (eds), Elsevier: Boston, Massachusetts, United States of America. 2014, pp. 805-820.

Colom. X. et al., "Structural analysis of photodegraded wood by means of FTIR spectroscopy," Polymer degradation and stability, vol. 80, Issue 3, 2003, pp. 543-549.

Constant. S. et al., "New insights into the structure and composition of technical lignins: a comparative characterisation study," Green Chemistry, vol. 18, Issue 9, 2016, pp. 2651-2665.

Davison. B.H. et al., "Variation of S/G ratio and lignin content in a Populus family influences the release of xylose by dilute acid hydrolysis," Applied biochemistry and biotechnology, vol. 130 2006, pp. 427-435.

Dee. SJ. et al., "A study of the acid-catalyzed hydrolysis of cellulose dissolved in ionic liquids and the factors influencing the dehydration of glucose and the formation of humins," ChemSusChem, vol. 4, Issue 8, 2011, pp. 1166-1173.

(56) References Cited

OTHER PUBLICATIONS

Devinsky. O. et al., "Cannabidiol: pharmacology and potential therapeutic role in epilepsy and other neuropsychiatric disorders," Epilepsia, vol. 55, Issue 6, 2014, pp. 791-802.

Duchemin. BJC. et al., "All-cellulose composites by partial dissolution in the ionic liquid 1-butyl-3-methylimidazolium chloride," Composites Part A: Applied Science and Manufacturing, vol. 40, Issue 12, 2009, pp. 2031-2037.

Dumitriu. S., "Polysaccharides: structural diversity and functional versatility," CRC press, 2004, 542 pages.

Dutta. T. et al., "Characterization of lignin streams during bionic liquid-based pretreatment from grass, hardwood, and softwood," ACS sustainable chemistry & engineering, vol. 6, Issue 3, 2018, pp. 3079-3090.

Edenhofer. O., "Climate change 2014: mitigation of climate change," vol. 3. Cambridge University Press, 2015, 35 pages.

Ehrensing. D., "Feasibility of industrial hemp production in the United States Pacific Northwest," 1998, 46 pages.

Enslow. KR. et al., "SnCl 4-catalyzed isomerization/dehydration of xylose and glucose to furanics in water," Catalysis Science & Technology, vol. 5, Issue 5, 2015, pp. 2839-2847.

Ewanick. SM. et al., "Acid-catalyzed steam pretreatment of lodgepole pine and subsequent enzymatic hydrolysis and fermentation to ethanol," Biotechnology and bioengineering, vol. 98, Issue 4, 2007, pp. 737-746.

Faix. O., "Fourier transform infrared spectroscopy," Methods in lignin chemistry. Berlin, Heidelberg: Springer Berlin Heidelberg, 1992, pp. 83-109.

Fan. M. et al., "Fourier transform infrared spectroscopy for natural fibres," Fourier transform-materials analysis, vol. 3, 2012, pp. 45-68.

Fang. Q. et al., "Experimental studies for levulinic acid production from whole kernel grain sorghum," Bioresource technology, vol. 81, Issue 3, 2002, pp. 187-192.

Ferrer. JL. et al., "Structure and function of enzymes involved in the biosynthesis of phenylpropanoids," Plant Physiology and Biochemistry, vol. 46, Issue 3, 2008, pp. 356-370.

Fujii. T. et al., "Enzymatic hydrolyzing performance of Acremonium cellulolyticus and Trichoderma reesei against three lignocellulosic materials," Biotechnology for Biofuels, vol. 2 2009, pp. 1-8.

Mes-Hartree. M. et al., "The nature of inhibitory materials present in pretreated lignocellulosic substrates which inhibit the enzymatic hydrolysis of cellulose," Biotechnology Letters, vol. 5, 1983, pp. 531-536.

Miyata. A. et al., "Reaction behavior of cellulose in various pyridinium-based ionic liquids," Journal of wood science, vol. 60 2014, pp. 438-445.

Morone. A. et al., "Levulinic acid production from renewable waste resources: Bottlenecks, potential remedies, advancements and applications," Renewable and Sustainable Energy Reviews, vol. 51, 2015, pp. 548-565.

Motagamwala. AH. et al., "Solvent system for effective near-term production of hydroxymethylfurfural (HMF) with potential for long-term process improvement," Energy & Environmental Science, vol. 12, Issue 7, 2019, pp. 2212-2222.

Muranaka. Y. et al., "Effective production of levulinic acid from biomass through pretreatment using phosphoric acid, hydrochloric acid, or ionic liquid," Industrial & Engineering Chemistry Research, vol. 53, Issue 29, 2014, pp. 11611-11621.

Nair. RB. et al., "Optimizing dilute phosphoric acid pretreatment of wheat straw in the laboratory and in a demonstration plant for ethanol and edible fungal biomass production using Neurospora intermedia," Journal of Chemical Technology & Biotechnology, vol. 92, Issue 6, 2017, pp. 1256-1265.

Nakagame. S. et al., "The isolation, characterization and effect of lignin isolated from steam pretreated Douglas-fir on the enzymatic hydrolysis of cellulose," Bioresource technology, vol. 102, Issue 6, 2011, pp. 4507-4517.

Nelson. ML. et al., "Relation of certain infrared bands to cellulose crystallinity and crystal latticed type. Part I. Spectra of lattice types I, II, III and of amorphous cellulose," Journal of applied polymer science, vol. 8, Issue 3, 1964, pp. 1311-1324.

Nguyen. QA. et al., "Two-stage dilute-acid pretreatment of softwoods," Applied Biochemistry and Biotechnology, vol. 84-86, 2000, pp. 561-576.

Nhien. LC. et al., "Design and assessment of hybrid purification processes through a systematic solvent screening for the production of levulinic acid from lignocellulosic biomass," Industrial & Engineering Chemistry Research, vol. 55, Issue 18, 2016, pp. 5180-5189.

Nitsos. C. et al., "Optimization of hydrothermal pretreatment of hardwood and softwood lignocellulosic residues for selective hemicellulose recovery and improved cellulose enzymatic hydrolysis," ACS Sustainable Chemistry & Engineering, vol. 4, Issue 9, 2016, pp. 4529-4544.

Nitsos. C. et al., "Organosolv fractionation of softwood biomass for biofuel and biorefinery applications," Energies, vol. 11, Issue 1, 2018, 23 pages.

Normark. M. et al., "Analysis, pretreatment and enzymatic saccharification of different fractions of Scots pine," BMC biotechnology, vol. 14, 2014, pp. 1-12.

Ohno. E. et al., "Reaction behavior of cellulose in an ionic liquid, 1-ethyl-3-methylimidazolium chloride," Journal of wood science, vol. 59, 2013, pp. 221-228.

Overend. RP. et al., "Fractionation of lignocellulosics by steam-aqueous pretreatments," Philosophical Transactions of the Royal Society of London. Series A, Mathematical and Physical Sciences, vol. 321, Issue 1561, 1987, pp. 523-536.

Pan. X. et al., "Enhanced enzymatic hydrolysis of steam-exploded Douglas fir wood by alkali-oxygen post-treatment," Applied Biochemistry and Biotechnology, vol. 113-116, 2004, pp. 1103-1114.

Pang. Z. et al., "High selective delignification using oxidative ionic liquid pretreatment at mild conditions for efficient enzymatic hydrolysis of lignocellulose," Bioresource Technology, vol. 214, 2016, pp. 96-101.

Park. S. et al., "Cellulose crystallinity index: measurement techniques and their impact on interpreting cellulase performance," Biotechnology for biofuels, vol. 3, 2010, pp. 1-10.

Park. S. et al., "Measuring the crystallinity index of cellulose by solid state 13 C nuclear magnetic resonance," Cellulose, vol. 16, 2009, pp. 641-647.

Parthasarathi. R. et al., "Theoretical study of the remarkably diverse linkages in lignin," The Journal of Physical Chemistry Letters, vol. 2, Issue 20, 2011, pp. 2660-2666.

Patil. SKR. et al., "Comparison of structural features of humins formed catalytically from glucose, fructose, and 5-hydroxymethylfurfuraldehyde," Energy & Fuels, vol. 26, Issue 8, 2012, pp. 5281-5293.

Perlack. RD., "Biomass as feedstock for a bioenergy and bioproducts industry: the technical feasibility of a billion-ton annual supply," Oak Ridge National Laboratory, 2005, 78 pages.

Pielhop. T. et al., "Steam explosion pretreatment of softwood: the effect of the explosive decompression on enzymatic digestibility," Biotechnology for Biofuels, vol. 9, 2016, pp. 1-13.

Pileidis. FD. et al., "Levulinic acid biorefineries: new challenges for efficient utilization of biomass," ChemSusChem, vol. 9, Issue 6, 2016, pp. 562-582.

Puls. J., "Chemistry and biochemistry of hemicelluloses: Relationship between hemicellulose structure and enzymes required for hydrolysis," Macromolecular symposia. vol. 120. No. 1. Basel: Hüthig & Wepf Verlag, vol. 120, 1997, pp. 183-196.

Rabideau. BD. et al., "The role of the cation in the solvation of cellulose by imidazolium-based ionic liquids," The Journal of Physical Chemistry B, vol. 118, Issue 6, 2014, pp. 1621-1629.

Rackermann. DW. et al., "The conversion of lignocellulosics to levulinic acid," Biofuels, Bioproducts and Biorefining, vol. 5, Issue 2, 2011, pp. 198-214.

Rackley. SA., "Carbon capture from power generation," Carbon capture and storage, 2017, pp. 75-101.

Rajan. K. et al., "Effect of dilute acid pretreatment conditions and washing on the production of inhibitors and on recovery of sugars during wheat straw enzymatic hydrolysis," Biomass and Bioenergy, vol. 62 2014, pp. 222-227.

(56) References Cited

OTHER PUBLICATIONS

Ranalli. P. et al., "Hemp as a raw material for industrial applications," Euphytica, vol. 140, Issue 1, 2004, pp. 1-6.

Remsing. RC. et al., "Mechanism of cellulose dissolution in the ionic liquid 1-n-butyl-3-methylimidazolium chloride: a 13 C and 35/37 CI NMR relaxation study on model systems," Chemical communications, vol. 12, 2006, pp. 1271-1273.

Rinaldi. R. et al., "Acid hydrolysis of cellulose as the entry point into biorefinery schemes," ChemSusChem: Chemistry & Sustainability Energy & Materials, vol. 2, Issue 12, 2009, pp. 1096-1107.

Rinaldi. R. et al., "Paving the way for lignin valorisation: recent advances in bioengineering, biorefining and catalysis," Angewandte Chemie International Edition, vol. 55, Issue 29, 2016, pp. 8164-8215.

Rollin. JA. et al., "Increasing cellulose accessibility is more important than removing lignin: A comparison of cellulose solvent-based lignocellulose fractionation and soaking in aqueous ammonia," Biotechnology and bioengineering, vol. 108, Issue 1, 2011, pp. 22-30.

Runge. T. et al., "Two-stage acid-catalyzed conversion of carbohydrates into levulinic acid," Industrial & engineering chemistry research, vol. 51, Issue 8, 2012, pp. 3265-3270.

Samuel. R. et al., "Structural changes in switchgrass lignin and hemicelluloses during pretreatments by NMR analysis," Polymer Degradation and Stability, vol. 96, Issue 11, 2011, pp. 2002-2009.

Sannigrahi. P. et al., "Effects of organosolv pretreatment and enzymatic hydrolysis on cellulose structure and crystallinity in Loblolly pine," Carbohydrate research, vol. 345, Issue 7, 2010, pp. 965-970.

Satari. B. et al., "Cellulose solvent-based pretreatment for enhanced second-generation biofuel production: a review," Sustain Energy Fuels, vol. 3, 2019, pp. 11-62.

Sathitsuksanoh. N. et al., "Cellulose solvent-and organic solvent-based lignocellulose fractionation enabled efficient sugar release from a variety of lignocellulosic feedstocks," Bioresource technology, vol. 117, 2012, pp. 228-233.

Sathitsuksanoh. N. et al., "Cellulose solvent-based biomass pretreatment breaks highly ordered hydrogen bonds in cellulose fibers of switchgrass," Biotechnology and Bioengineering, vol. 108, Issue 3, 2011, pp. 521-529.

Sathitsuksanoh. N. et al., "Cellulose solvent-based pretreatment for corn stover and avicel: concentrated phosphoric acid versus ionic liquid [BMIM] CI," Cellulose, vol. 19, 2012, pp. 1161-1172.

Sathitsuksanoh. N. et al., "Characterization Methods and Techniques," Introduction to Renewable Biomaterials: First Principles and Concepts, 2017, pp. 107-140.

Sathitsuksanoh. N. et al., "How alkyl chain length of alcohols affects lignin fractionation and ionic liquid recycle during lignocellulose pretreatment," BioEnergy Research, vol. 8, 2015, pp. 973-981.

Sathitsuksanoh. N. et al., "Lignin fate and characterization during ionic liquid biomass pretreatment for renewable chemicals and fuels production," Green Chemistry, vol. 16, Issue 3, 2014, pp. 1236-1247.

Sathitsuksanoh. N. et al., "New lignocellulose pretreatments using cellulose solvents: a review," Journal of Chemical Technology & Biotechnology, vol. 88, Issue 2, 2013, pp. 169-180.

Schafer. T. et al., "Selective recovery of solutes from ionic liquids by pervaporation—a novel approach for purification and green processing," Chemical Communications, vol. 17, 2001, pp. 1622-1623.

Schultz. TP. et al., "Quantitative structural analysis of lignin by diffuse reflectance Fourier transform infrared spectrometry," Holzforschung, vol. 40, 1986, pp. 37-44.

Schutyser. W. et al., "Chemicals from lignin: an interplay of lignocellulose fractionation, depolymerisation, and upgrading," Chemical society reviews, vol. 47, Issue 3, 2018, pp. 852-908.

Segal. L. et al., "An empirical method for estimating the degree of crystallinity of native cellulose using the X-ray diffractometer," Textile research journal, vol. 29, Issue 10, 1959, pp. 786-794.

Serrano-Ruiz. JC. et al., "Catalytic upgrading of levulinic acid to 5-nonanone," Green Chemistry, vol. 12, Issue 4, 2010, pp. 574-577.

Wu, W., et al., "Phosphoric acid based pretreatment of switchgrass and fermentation of entire slurry to ethanol using a simplified process.", Bioresource technology, vol. 251, 2018, pp. 171-180.

Xin, H., et al., "Dehydration of glucose to 5-hydroxymethylfurfural and 5-ethoxymethylfurfural by combining Lewis and Brønsted acid.", RSC advances, vol. 7, No. 66, 2017, pp. 41546-41551.

Xu, A., et al., "Effects of anionic structure and lithium salts addition on the dissolution of cellulose in 1-butyl-3-methylimidazolium-based ionic liquid solvent systems.", Green chemistry, vol. 12, No. 2, 2010, pp. 268-275.

Xu, C., et al., "Conversion of lignin into bio-based chemicals and materials.", Springer, 2017.

Xu. H. et al., "Solvent Tuning the Selective Hydrogenation of Levulinic Acid into Biofuels over Ni-Metal Organic Framework-Derived Catalyst," ACS Appl. Energy Mater, vol. 2, 2019, pp. 6979-6983.

Yang, B., et al., "Fast and efficient alkaline peroxide treatment to enhance the enzymatic digestibility of steam-exploded softwood substrates.", Biotechnology and bioengineering, vol. 77, No. 6, 2002, pp. 678-684.

Yang, B., et al., "Pretreatment: the key to unlocking low-cost cellulosic ethanol.", Biofuels, Bioproducts and Biorefining: Innovation for a sustainable economy, vol. 2, No. 1, 2008, pp. 26-40.

Yelle, D. J., et al., "Characterization of nonderivatized plant cell walls using high-resolution solution-state NMR spectroscopy.", Magnetic Resonance in Chemistry, vol. 46, No. 6, 2008, pp. 508-517.

Yi. Z. et al., "Metal regulating the highly selective synthesis of gamma-valerolactone and valeric biofuels from biomass-derived levulinic acid," Fuel, vol. 259, 2020, 4 pages.

Yoon, S-Y., et al., "The effect of hemicelluloses and lignin on acid hydrolysis of cellulose.", Energy, vol. 77, 2014, pp. 19-24.

Yu, H., et al., "Characterization of mechanical pulverization/phosphoric acid pretreatment of corn stover for enzymatic hydrolysis.", Bioresource technology, vol. 282, 2019, pp. 69-74.

Zhang, J., et al., "Dissolution of microcrystalline cellulose in phosphoric acid—molecular changes and kinetics.", Molecules, vol. 14, No. 12, 2009, pp. 5027-5041.

Zhang, L., et al., "Revealing the molecular structural transformation of hardwood and softwood in dilute acid flowthrough pretreatment.", ACS Sustainable Chemistry & Engineering, vol. 4, No. 12, 2016, pp. 6618-6628.

Zhang, X., et al., "Extraction and characterization of lignin from corncob residue after acid-catalyzed steam explosion pretreatment.", Industrial Crops and Products, vol. 133, 2019, pp. 241-249.

Zhang, Y-H. P., et al., "A transition from cellulose swelling to cellulose dissolution by o-phosphoric acid: evidence from enzymatic hydrolysis and supramolecular structure.", Biomacromolecules, vol. 7, No. 2, 2006, pp. 644-648.

Zhang, Y.-H. P., et al., "Toward an aggregated understanding of enzymatic hydrolysis of cellulose: noncomplexed cellulase systems.", Biotechnology and bioengineering, vol. 88, No. 7, 2004, pp. 797-824.

Zhao, H., et al., "Metal chlorides in ionic liquid solvents convert sugars to 5-hydroxymethylfurfural.", Science, vol. 316, No. 5831, 2007, pp. 1597-1600.

Zhao, H., et al., "Regenerating cellulose from ionic liquids for an accelerated enzymatic hydrolysis.", Journal of biotechnology, vol. 139, No. 1, 2009, pp. 47-54.

Zheng, J., et al., "Experimental and mathematical simulation of noncompetitive and competitive adsorption dynamic of formic acid-Levulinic acid-5-Hydroxymethylfurfural from single, binary, and ternary systems in a fixed-bed column of SY-01 resin.", Industrial & Engineering Chemistry Research, vol. 57, No. 25, 2018, pp. 8518-8528.

Zhu, J. Y., et al., "High titer ethanol production from simultaneous enzymatic saccharification and fermentation of aspen at high solids: a comparison between SPORL and dilute acid pretreatments.", Bioresource technology, vol. 102, No. 19, 2011, pp. 8921-8929.

(56)          References Cited

OTHER PUBLICATIONS

Zhu, Z., et al., "Comparative study of corn stover pretreated by dilute acid and cellulose solvent-based lignocellulose fractionation: Enzymatic hydrolysis, supramolecular structure, and substrate accessibility.", Biotechnology and bioengineering, vol. 103, No. 4, 2009, pp. 715-724.

Ziebell, A., et al., "Increase in 4-coumaryl alcohol units during lignification in alfalfa (Medicago sativa) alters the extractability and molecular weight of lignin.", Journal of Biological Chemistry, vol. 285, No. 50, 2010, p. 38961-38968.

Gao. S. et at., "New insights into enzymatic hydrolysis of heterogeneous cellulose by using carbohydrate-binding module 3 containing GFP and carbohydrate-binding module 17 containing CFP," Biotechnology for biofuels, vol. 7, 2014, pp. 1-11.

Girisuta. B. et al., "Experimental and kinetic modelling studies on the acid-catalysed hydrolysis of the water hyacinth plant to levulinic acid," Bioresource technology, vol. 99, Issue 17, 2008, pp. 8367-8375.

Girisuta. B. et al., "Green chemicals: A kinetic study on the conversion of glucose to levulinic acid," Chemical Engineering Research and Design, vol. 84, Issue 5, 2006, pp. 339-349.

Gschwend. FJV. et al., "Quantitative glucose release from softwood after pretreatment with low-cost ionic liquids," Green Chemistry, vol. 21, Issue 3, 2019, pp. 692-703.

Gupta. K. et al., "Cellulose dissolution and regeneration in ionic liquids: A computational perspective," Chemical Engineering Science, vol. 121, 2015, pp. 180-189.

Ha. SH. et al., "Microwave-assisted separation of ionic liquids from aqueous solution of ionic liquids," Journal of Chromatography A, vol. 1217, Issue 49, 2010, pp. 7638-7641.

Hall. M. et al., "Cellulose crystallinity—a key predictor of the enzymatic hydrolysis rate," The FEBS journal, vol. 277, Issue 6, 2010, pp. 1571-1582.

Hausfather, Z., "State of the climate: 2018 set to be fourth warmest year despite cooler start.", Carbon Brief, Clear on Climate, Aug. 1, 2018, 13 pages.

Hayes. DJ. et al., "The biofine process-production of levulinic acid, furfural, and formic acid from lignocellulosic feedstocks," Biorefineries—Industrial Processes and Product, vol. 1, 2006, pp. 139-164.

Heikkinen. S. et al., "Quantitative 2D HSQC (Q-HSQC) via suppression of J-dependence of polarization transfer in NMR spectroscopy: application to wood lignin," Journal of the American Chemical Society, vol. 125, Issue 14, 2003, pp. 4362-4367.

Heinze. T. et al., "Ionic liquids as reaction medium in cellulose functionalization," Macromolecular bioscience, vol. 5, Issue 6, 2005, pp. 520-525.

Hewetson. BB. et al., "Enhanced acid-catalyzed biomass conversion to hydroxymethylfurfural following cellulose solvent-and organic solvent-based lignocellulosic fractionation pretreatment," Energy & Fuels, vol. 30, Issue 11, 2016, pp. 9975-9977.

Hong. J. et al., "Bioseparation of recombinant cellulose-binding module-proteins by affinity adsorption on an ultra-high-capacity cellulosic adsorbent," Analytica chimica acta, vol. 621, Issue 2, 2008, pp. 193-199.

Hong. J. et al., "Quantitative determination of cellulose accessibility to cellulase based on adsorption of a nonhydrolytic fusion protein containing CBM and GFP with its applications," Langmuir, vol. 23, Issue 25, 2007, pp. 12535-12540.

Horvat. J. et al., "Mechanism of levulinic acid formation," Tetrahedron letters, vol. 26, Issue 17, 1985, pp. 2111-2114.

Hossain. MA. et al., "Catalytic cleavage of the β-O-4 aryl ether bonds of lignin model compounds by Ru/C catalyst," Applied Catalysis A: General, vol. 582, 2019, 30 pages.

Hsu. PH. et al., "Formation of X-ray amorphous and crystalline aluminium hydroxides1," Mineralogical magazine and journal of the Mineralogical Society, vol. 33, Issue 264, 1964, pp. 749-768.

Hu. X. et al., "One-pot conversion of biomass-derived xylose and furfural into levulinate esters via acid catalysis," Chemical Communications, vol. 53, Issue 20, 2017, pp. 2938-2941.

Jia. X. et al., "Preparation and characterization of cellulose regenerated from phosphoric acid," Journal of Agricultural and Food Chemistry, vol. 61, Issue 50, 2013, pp. 12405-12414.

Jin. M. et al., "Toward high solids loading process for lignocellulosic biofuel production at a low cost," Biotechnology and Bioengineering, vol. 114, Issue 5, 2017, pp. 980-989.

Kaldstrom. M. et al., "Deciphering 'water-soluble lignocellulose' obtained by mechanocatalysis: new insights into the chemical processes leading to deep depolymerization," Green Chemistry, vol. 16, Issue 7, 2014, pp. 3528-3538.

Kang. P. et al., "Theoretical study on the mechanisms of cellulose dissolution and precipitation in the phosphoric acid-acetone process," Carbohydrate polymers, vol. 90, Issue 4, 2012, pp. 1771-1778.

Kang. S. et al., "Concentrated levulinic acid production from sugar cane molasses," Energy & Fuels, vol. 32, Issue 3, 2018, pp. 3526-3531.

Khan. BA. et al., "Antibacterial properties of hemp hurd powder against E. coli," Journal of Applied Polymer Science, vol. 132, Issue 10, 2015, pp. 1-6.

Kim. H. et al., "A gel-state 2D-NMR method for plant cell wall profiling and analysis: a model study with the amorphous cellulose and xylan from ball-milled cotton linters," Rsc Advances, vol. 4, Issue 15, 2014, pp. 7549-7560.

Kim. H. et al., "Solution-state 2D NMR of ball-milled plant cell wall gels in DMSO-d 6," BioEnergy Research, vol. 1, 2008, pp. 56-66.

Kim. H. et al., "Solution-state 2D NMR of ball-milled plant cell wall gels in DMSO-d6/pyridine-d5," Organic & biomolecular chemistry, vol. 8, Issue 3, 2010, pp. 576-591.

Kim. JY. et al "Recovery of phosphoric acid from mixed waste acids of semiconductor industry by diffusion dialysis and vacuum distillation," Separation and purification technology, vol. 90, 2012, pp. 64-68.

Kim. KH. et al., "Recent efforts to prevent undesirable reactions from fractionation to depolymerization of lignin: toward maximizing the value from lignin," Frontiers in Energy Research, vol. 6, 2018, 7 pages.

Kishimoto. T. et al., "Influence of syringyl to guaiacyl ratio on the structure of natural and synthetic lignins," Journal of agricultural and food chemistry, vol. 58, Issue 2, 2010, pp. 895-901.

Klein-Marcuschamer. D. et al., "Techno-economic analysis of a lignocellulosic ethanol biorefinery with ionic liquid pre-treatment," Biofuels, Bioproducts and Biorefining, vol. 5, Issue 5, 2011, pp. 562-569.

Klein-Marcuschamer. D. et al., "Technoeconomic analysis of biofuels: A wiki-based platform for lignocellulosic biorefineries," biomass and bioenergy, vol. 34, Issue 12, 2010, pp. 1914-1921.

Kobayashi. SU. et al., "Development of novel Lewis acid catalysts for selective organic reactions in aqueous media," Accounts of chemical research, vol. 35, Issue 4, 2002, pp. 209-217.

Kreuger. E. et al., "Bioconversion of industrial hemp to ethanol and methane: the benefits of steam pretreatment and co-production," Bioresource technology, vol. 102, Issue 3, 2011, pp. 3457-3465.

Leizer. C. et al., "The composition of hemp seed oil and its potential as an important source of nutrition," Journal of Nutraceuticals, functional & medical foods, vol. 2, Issue 4, 2000, pp. 35-53.

Li. G. et al., "A density functional theory study of the mechanism of direct glucose dehydration to 5-hydroxymethylfurfural on anatase titania," ChemCatChem, vol. 10, Issue 18, 2018, pp. 4084-4089.

Li. H. et al., "Simultaneous saccharification and fermentation of lignocellulosic residues pretreated with phosphoric acid-acetone for bioethanol production," Bioresource technology, vol. 100, Issue 13, 2009, pp. 3245-3251.

Li. J. et al., "Lignin depolymerization/repolymerization and its critical role for delignification of aspen wood by steam explosion," Bioresource technology, vol. 98, Issue 16, 2007, pp. 3061-3068.

Li. N. et al., "An uncondensed lignin depolymerized in the solid state and isolated from lignocellulosic biomass: a mechanistic study," Green Chemistry, vol. 20, Issue 18, 2018, pp. 4224-4235.

(56)                    References Cited

OTHER PUBLICATIONS

Li. Y. et al., "Towards a molecular understanding of cellulose dissolution in ionic liquids: Anion/cation effect, synergistic mechanism and physicochemical aspects," Chemical science, vol. 9, Issue 17, 2018, pp. 4027-4043.

Licursi. D. et al., "A novel approach to biphasic strategy for intensification of the hydrothermal process to give levulinic acid: use of an organic non-solvent," Bioresource Technology, vol. 264, 2018, pp. 180-189.

Liimatainen. H. et al., "Characterization of highly accessible cellulose microfibers generated by wet stirred media milling," Carbohydrate Polymers, vol. 83, Issue 4, 2011, pp. 2005-2010.

Liu. LY. et al., "Uniform chemical functionality of technical lignin using ethylene carbonate for hydroxyethylation and subsequent greener esterification," ACS Sustainable Chemistry & Engineering, vol. 6, Issue 9, 2018, pp. 12251-12260.

Liu. Y. et al., "Phosphorus Cycle," In Encyclopedia of Ecology. Jorgensen & Fath (eds.) Academic Press: Oxford, 2008, pp. 2715-2724.

Lu. Y. et al., "Influence of high solid concentration on enzymatic hydrolysis and fermentation of steam-exploded corn stover biomass," Applied biochemistry and biotechnology, vol. 160, 2010, pp. 360-369.

Mabee. WE. et al., "Updates on softwood-to-ethanol process development," Twenty-seventh symposium on biotechnology for fuels and chemicals, Humana Press, vol. 129, 2006, pp. 55-70.

Mansfield. SD. et al., "Whole plant cell wall characterization using solution-state 2D NMR," Nature protocols, vol. 7, Issue 9, 2012, pp. 1579-1589.

Marchessault. RH. et al., "Application of infra-red spectroscopy to cellulose and wood polysaccharides," Pure and Applied Chemistry, vol. 5, Issue 1-2, 1962, pp. 107-130.

Marchessault. RH. et al., "The infrared spectra of crystalline polysaccharides. VIII. Xylans," Journal of Polymer Science, vol. 59, Issue 168, 1962, pp. 357-378.

Sette. M. et al., "Elucidation of lignin structure by quantitative 2D NMR," Chemistry—A European Journal, vol. 17, Issue 34, 2011, pp. 9529-9535.

Sette. M. et al., "Quantitative HSQC analyses of lignin: a practical comparison," Computational and structural biotechnology journal, vol. 6, Issue 7, 2013, pp. 1-7.

Sheldon RA., "The E factor: fifteen years on," Green Chemistry, vol. 9, Issue 12, 2007, pp. 1273-1283.

Sheldon. RA. et al., "Toward concise metrics for the production of chemicals from renewable biomass," Catalysis today, vol. 239, 2015, pp. 3-6.

Sheldon. RA., "The E factor 25 years on: the rise of green chemistry and sustainability," Green Chemistry, vol. 19, Issue 1, 2017, pp. 18-43.

Shen. J. et al., "Hydrochloric acid-catalyzed levulinic acid formation from cellulose: data and kinetic model to maximize yields," AIChE Journal, vol. 58, Issue 1, 2012, pp. 236-246.

Shuai. L. et al., "Comparative study of SPORL and dilute-acid pretreatments of spruce for cellulosic ethanol production," Bioresource Technology, vol. 101, Issue 9, 2010, pp. 3106-3114.

Sills. DL. et al., "Using FTIR to predict saccharification from enzymatic hydrolysis of alkali-pretreated biomasses," Biotechnology and bioengineering, vol. 109, Issue 2, 2012, pp. 353-362.

Sipos. B. et al., "Steam pretreatment of dry and ensiled industrial hemp for ethanol production," biomass and bioenergy, vol. 34, Issue 12, 2010, pp. 1721-1731.

Sipos. B. et al., "Sweet sorghum as feedstock for ethanol production: enzymatic hydrolysis of steam-pretreated bagasse," Applied biochemistry and biotechnology, vol. 153, 2009, pp. 151-162.

Siripong. P. et al., "Phosphoric acid pretreatment of Achyranthes aspera and Sida acuta weed biomass to improve enzymatic hydrolysis," Bioresource Technology, vol. 203, 2016, pp. 303-308.

Sluiter A, et al., "Determination of structural carbohydrates and lignin in biomass," Laboratory analytical procedure, vol. 1617, Issue 1, 2008, pp. 1-16.

Sluiter. A. et al., "Determination of Ash in Biomass," LAP, 2008, 8 pages.

Sluiter. JB. et al., "Compositional analysis of lignocellulosic feedstocks. 1. Review and description of methods," Journal of agricultural and food chemistry, vol. 58, Issue 16, 2010, pp. 9043-9053.

Soderstrom. J. et al., "Two-step steam pretreatment of softwood with SO 2 impregnation for ethanol production," Biotechnology for Fuels and Chemicals: The Twenty-Third Symposium. Humana Press, vol. 98-100, 2002, pp. 5-21.

Son. PA. et al., "Synthesis of levulinic acid from fructose using Amberlyst-15 as a solid acid catalyst," Reaction Kinetics, Mechanisms and Catalysis, vol. 106, Issue 1, 2012, pp. 185-192.

Stahlberg. T. et al., "Direct conversion of glucose to 5-(hydroxymethyl) furfural in ionic liquids with lanthanide catalysts," Green Chemistry, vol. 12, Issue 2, 2010, pp. 321-325.

Stansbury, L., "Annual Retail Sales for Hemp Products Estimated at $688 Million.", Vote Hemp, 2016, 5 pages.

Sun. N. et al., "Blending municipal solid waste with corn stover for sugar production using ionic liquid process," Bioresource technology, vol. 186, 2015, pp. 200-206.

Sun. N. et al., "Complete dissolution and partial delignification of wood in the ionic liquid 1-ethyl-3-methylimidazolium acetate," Green Chemistry, vol. 11, Issue 5, 2009, pp. 646-655.

Sun. N. et al., "Production and extraction of sugars from switchgrass hydrolyzed in ionic liquids," Biotechnology for Biofuels, vol. 6, 2013, pp. 1-15.

Sun. Z. et al., "Bright side of lignin depolymerization: toward new platform chemicals," Chemical reviews, vol. 118, Issue 2, 2018, pp. 614-678.

Swatloski. RP. et al., "Dissolution of cellose with ionic liquids," Journal of the American chemical society, vol. 124, Issue 18, 2002, pp. 4974-4975.

Swift. TD. et al. "Tandem Lewis/Brønsted homogeneous acid catalysis: conversion of glucose to 5-hydoxymethylfurfural in an aqueous chromium (III) chloride and hydrochloric acid solution," Green Chemistry, vol. 17, Issue 10, 2015, pp. 4725-4735.

Swift. TD. et al., "Tandem Lewis acid/Brønsted acid-catalyzed conversion of carbohydrates to 5-hydroxymethylfurfural using zeolite beta," Journal of catalysis, vol. 333, 2016, pp. 149-161.

Szijarto. N. et al., "Hydrolysis of amorphous and crystalline cellulose by heterologously produced cellulases of Melanocarpus albomyces," Journal of biotechnology, vol. 136, Issue 3-4, 2008, pp. 140-147.

Takada. M. et al., "The influence of lignin migration and relocation during steam pretreatment on the enzymatic hydrolysis of softwood and corn stover biomass substrates," Biotechnology and Bioengineering, vol. 116, Issue 11, 2019, pp. 2864-2873.

Tarasov D. et al., "Lignin-carbohydrate complexes: properties, applications, analyses, and methods of extraction: a review," Biotechnology for biofuels, vol. 11, 2018, pp. 1-28.

Taylor, A. W., et al., "High vacuum distillation of ionic liquids and separation of ionic liquid mixtures.", Physical Chemistry Chemical Physics, vol. 12, No. 8, 2010, pp. 1772-1783.

Torr, K. M., et al., "The impact of ionic liquid pretreatment on the chemistry and enzymatic digestibility of Pinus radiata compression wood.", Green Chemistry, vol. 14, No. 3, 2012, pp. 778-787.

Trinh, L. T. P., et al., "Characterization of ionic liquid pretreatment and the bioconversion of pretreated mixed softwood biomass.", Biomass and bioenergy, vol. 81, 2015, pp. 1-8.

Tuercke, T., et al., "Microreactor process for the optimized synthesis of 5-hydroxymethylfurfural: a promising building block obtained by catalytic dehydration of fructose.", Chemical Engineering & Technology: Industrial Chemistry-Plant Equipment-Process Engineering-Biotechnology, vol. 32, No. 11, 2009, pp. 1815-1822.

Van Der, W., et al., "The environmental impacts of the production of hemp and flax textile yarn.", industrial crops and products, vol. 27, No. 1, 2008, pp. 1-10.

Van Zandvoort, I., et al., "Formation, molecular structure, and morphology of humins in biomass conversion: influence of feedstock and processing conditions.", ChemSusChem, vol. 6, No. 9, 2013, pp. 1745-1758.

Vanoye, L., et al., "Kinetic model for the hydrolysis of lignocellulosic biomass in the ionic liquid, 1-ethyl-3-methyl-imidazolium chloride.", Green chemistry, vol. 11, No. 3, 2009, pp. 390-396.

(56)          References Cited

OTHER PUBLICATIONS

Vogl, C. R., et al., "Hemp (*Cannabis sativa* L.) as a resource for green cosmetics: Yield of seed and fatty acid compositions of 20 varieties under the growing conditions of organic farming in Austria.", Journal of Industrial Hemp, vol. 9, No. 1, 2004, pp. 51-68.

VoteHemp. U. S. Hemp Crop Report. online available at https://www.votehemp.com/u-s-hemp-crop-report. (accessed Oct. Oct. 2019). 5 pages.

Wada, M., et al., "Enzymatic hydrolysis of cellulose I is greatly accelerated via its conversion to the cellulose II hydrate form.", Polymer Degradation and Stability, vol. 95, No. 4, 2010, pp. 543-548.

Wagner, A., et al., "Syringyl lignin production in conifers: Proof of concept in a Pine tracheary element system.", Proceedings of the National Academy of Sciences, vol. 112, No. 19, 2015, pp. 6218-6223.

Wang, T., et al., "Water-compatible Lewis acid-catalyzed conversion of carbohydrates to 5-hydroxymethylfurfural in a biphasic solvent system.", Topics in Catalysis, vol. 55, 2012, pp. 657-662.

Wang, W., et al., "Synthesis of renewable diesel with 2-methylfuran and angelica lactone derived from carbohydrates.", Green Chemistry, vol. 18, No. 5, 2016, pp. 1218-1223.

Wang. C. et al., Revealing the structure and distribution changes of Eucalyptus lignin during the hydrothermal and alkaline pretreatments, Scientific reports, vol. 7, Issue 1, 2017, 10 pages.

Weingarten, R., et al., "Conversion of glucose into levulinic acid with solid metal (IV) phosphate catalysts.", Journal of Catalysis, vol. 304, 2013, pp. 123-134.

Weingarten, R., et al., "Production of levulinic acid from cellulose by hydrothermal decomposition combined with aqueous phase dehydration with a solid acid catalyst.", Energy & Environmental Science, vol. 5, No. 6, 2012, pp. 7559-7574.

Weiqi, W., et al., "Experimental and kinetic study of glucose conversion to levulinic acid catalyzed by synergy of Lewis and Brønsted acids.", Chemical engineering journal, vol. 307, 2017, pp. 389-398.

Wen, J.-L., et al., "Fractionation of bamboo culms by autohydrolysis, organosolv delignification and extended delignification: Understanding the fundamental chemistry of the lignin during the integrated process.", Bioresource technology, vol. 150, 2013, pp. 278-286.

Willfor, S., et al., "Spruce-derived mannans—A potential raw material for hydrocolloids and novel advanced natural materials.", Carbohydrate Polymers, vol. 72, No. 2, 2008, pp. 197-210.

Wiman, M., et al., "Cellulose accessibility determines the rate of enzymatic hydrolysis of steam-pretreated spruce.", Bioresource Technology, vol. 126, 2012, pp. 208-215.

Windom, B. C., et al., "Advanced distillation curve analysis on ethyl levulinate as a diesel fuel oxygenate and a hybrid biodiesel fuel.", Energy & Fuels, vol. 25, No. 4, 2011, pp. 1878-1890.

Wright, W. R., et al., "Development of heterogeneous catalysts for the conversion of levulinic acid to ?-valerolactone.", ChemSusChem, vol. 5, No. 9, 2012, pp. 1657-1667.

* cited by examiner

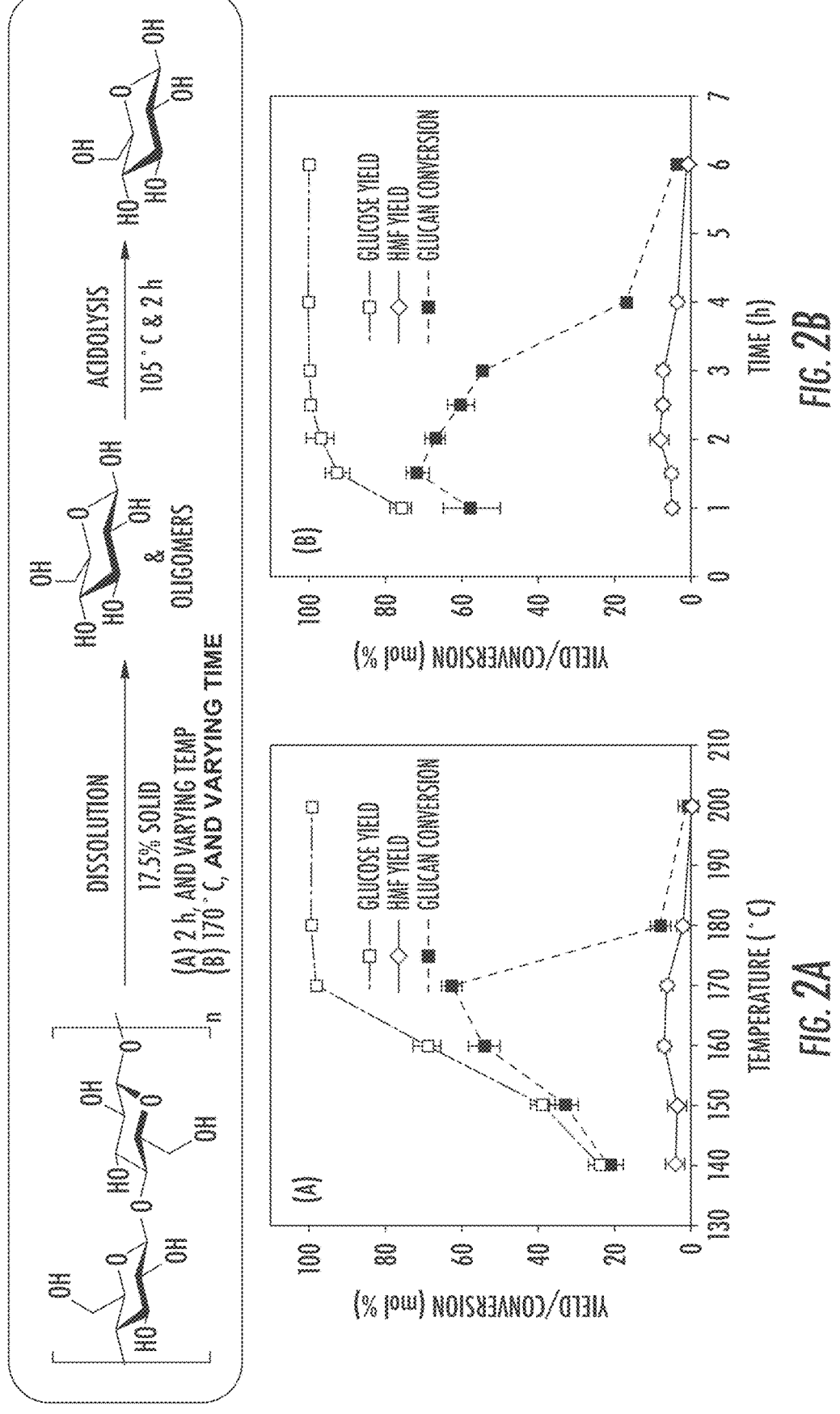

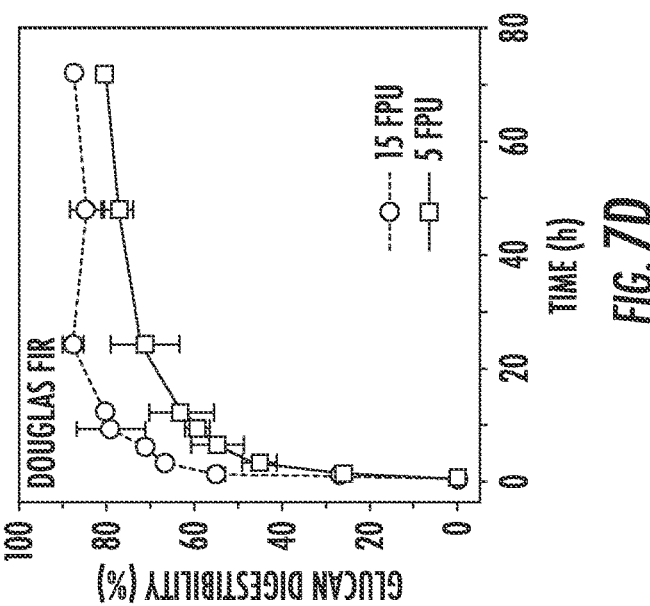
*FIG. 7D*
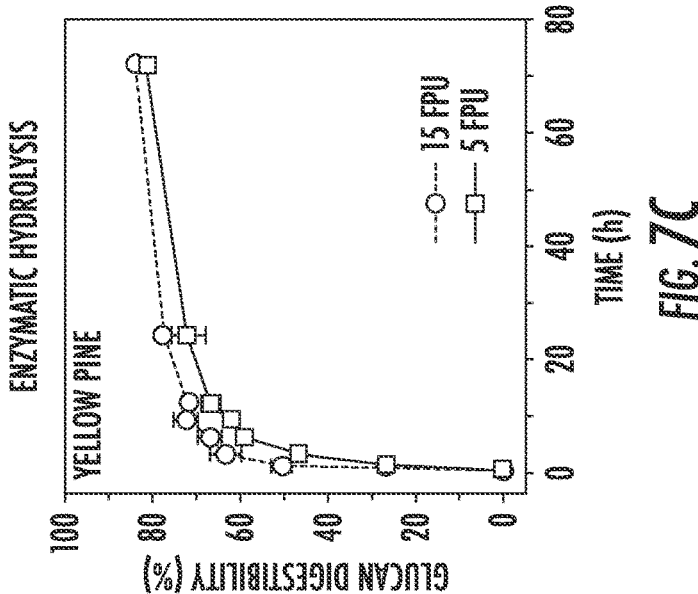
*FIG. 7C*
PRETREATED
SOFTWOOD
50 °C, 72h,
ENZYME
ENZYMATIC
HYDROLYSIS
*FIG. 7B*

ONE-POT ACID-CATALYZED LEVULINIC ACID PRODUCTION FROM LIGNOCELLULOSIC BIOMASS

CROSS-REFERENCE TO RELATED APPLICATIONS

This application is a United States National Phase Entry of PCT International Patent Application No. PCT/US2020/028553, filed Apr. 16, 2020, incorporated herein by reference in its entirety and which claims the benefit of U.S. Provisional Patent Application Ser. No. 62/834,775, filed Apr. 16, 2019, the disclosure of which is incorporated herein by reference in its entirety.

This application claims the benefit of U.S. Provisional Patent Application Ser. No. 62/834,775, filed Apr. 16, 2019, the disclosure of which is incorporated herein by reference in its entirety.

GOVERNMENT INTEREST

This invention was made with government support under Cooperative Agreement 1355438 awarded by the National Science Foundation. The government has certain rights in the invention.

TECHNICAL FIELD

The presently disclosed subject matter relates in some embodiments to methods for producing levulinic acid from hemp hurds and other sugar sources. In some embodiments, the presently disclosed subject matter relates to a method comprising dissolving hemp hurds in an ionic liquid medium to produce a cellulose-rich product; hydrolyzing cellulose present in the cellulose-rich product to produce a glucose-rich product; dehydrating glucose present in the glucose-rich product, and/or fructose resulting from isomerization of the glucose, to produce 5-hydroxymethyl furfural (HMF); and hydrolyzing the HMF to levulinic acid.

BACKGROUND

Increasing demand for transportation fuels and decreasing petroleum supplies have led to growing interest in using lignocellulose as a renewable feedstock for production of biofuels and chemicals. Cellulose-derived biofuels could supplement current transportation fuels, reduce air pollution, create jobs, and lessen the effects of petroleum-based fuels on climate. Industrial hemp, a variety of the *Cannabis sativa* L. and the same plant species as marijuana, has been of great interest because this fast-growing plant is a rich source of phytochemicals, fibers, and woody products (Ash, 1948; Ehrensing, 1998; Brady, 2003; Deitch, 2003; Ranalli & Venturi, 2004; Andre et al., 2016). For example, its outer shell (bast) can be used to make fibers for textiles (van der Werf & Turunen, 2008). Its flowering materials (e.g., flowers and leaves) are good sources for high-valued cannabidiol (CBD) oil (Leizer et al., 2000), which is used for pharmaceutical applications (Devinsky et al., 2014). Hemp oil can be extracted from seeds for cooking and cosmetics (Vogl et al., 2004). The by-product, hemp hurds (the soft inner core of the stalks and stems) is rich in cellulose and currently used in low-valued applications including garden mulch, lightweight paperboard, and acoustical ceiling (Asdrubali, 2006; Barberà et al., 2011). Although every part of the industrial hemp plant can be used to produce a variety of products, research on industrial hemp has been controversial in numerous parts of the world. This controversy is attributable to the misconception that hemp and marijuana are the same plant. This misunderstanding has significantly hindered hemp research. The Vote Hemp has estimated the retail hemp products sold in the United States in 2016 to be greater than $688 M, a ~25% increase from 2015 that is projected to continue (VoteHemp, 2016). With the projected expansion of industrial hemp production, a large amount of under-utilized hemp hurds will become available.

Previous methods to produce levulinic acid from plant biomass involved multi-step processes that employed expensive precious metal catalysts and harsh conditions (e.g., high pressure and temperature; see e.g. U.S. Patent Application Publication Nos. 2017/0190682, 2017/0183322, and 2015/0052806, and U.S. Pat. No. 9,346,730; each of which is incorporated by reference herein in its entirety). Furthermore, one of the major challenges in production of levulinic acid is the separation of intermediate products: glucose and HMF. Separation is one of the costly steps that hampers commercialization of the process. Thus, an integrated process that eliminates the separation of intermediate products would be desirable. The presently disclosed subject matter thus relates to successfully converted cellulosic biomass into levulinic acid in one pot with high yield and selectivity. Among other advantages, the presently disclosed one-pot strategy eliminates the costly separation steps.

SUMMARY

This Summary lists several embodiments of the presently disclosed subject matter, and in many cases lists variations and permutations of these embodiments of the presently disclosed subject matter. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

The presently disclosed subject matter relates in some embodiments to methods for producing levulinic acid from hemp hurds. In some embodiments, the methods comprise dissolving hemp hurds in an ionic liquid medium to produce a cellulose-rich product; hydrolyzing cellulose present in the cellulose-rich product to produce a glucose-rich product; dehydrating glucose present in the glucose-rich product, and/or fructose resulting from isomerization of the glucose, to produce 5-hydroxymethyl furfural (HMF); and hydrolyzing the HMF to levulinic acid. In some embodiments, the ionic liquid medium comprises 1-ethyl-3-methylimidazolium chloride ($[C_2C_1im]Cl$) and hydrochloric acid at about a 0.1 HCl/Biomass weight ratio. In some embodiments, the dissolving step occurs at a temperature of about 140° C. to about 200° C. and/or for time of between about 60 and about 360 minutes. In some embodiments, the hydrolyzing step occurs at a temperature of between about 95° C. and 125° C. for about two hours or occurs at about 95° C. for about 1 to about 6 hours and provides a yield of at least 25% glucose. In some embodiments, the hydrolyzing step occurs at a temperature of between about 95° C. and 120° C. for about two hours or occurs at about 95° C. for at least 2 hours and provides a yield of at least 40%, optionally at least 50%, further optionally at least 60%, 70%, or 80% glucose. In some embodiments, the hydrolyzing step is performed in the presence of an acid catalyst, optionally wherein the Lewis acid catalyst is selected from the group consisting of $CrCl_3.6H_2O$, $AlCl_3.6H_2O$, $ZrCl_4$, and $SnCl_4.5H_2O$. In some embodiments, the presently disclosed methods produce a levulinic acid yield of at least about 40 mol %, optionally at least about 45 mol %, optionally at least about 50 mol %, optionally at least about 55 mol %, and optionally at least about 60 mol %.

The presently disclosed subject matter also relates in some embodiments to methods for producing levulinic acid from a sugar source, In some embodiments, the methods comprise providing a sugar source, wherein the sugar source comprises a hydrolysis product produced by hydrolyzing a cellulose-rich product generated from hemp hurds and/or comprises a cellulase digestion product of softwood pre-treated with phosphoric acid ($H_3PO_4$); dehydrating glucose present in the sugar source, and/or fructose resulting from isomerization of glucose present in the sugar source, to produce 5-hydroxymethyl furfural (HMF); and hydrolyzing the HMF to levulinic acid. In some embodiments, the cellulose-rich product is produced by dissolving hemp hurds in an ionic liquid medium. In some embodiments, the ionic liquid medium comprises a first component selected from the group consisting of 1-ethyl-3-methylimidazolium chloride ($[C_2C_1im]Cl$), 1-butyl-3-methylimidazolium chloride, 1-butyl-3-methylimidazolium hexafluorophosphate, 1-butyl-3-methylimidazolium acetate, 1-butyl-1-methylpyr-rolidinium chloride, 1-butyl-3-methylimidazolium methyl-sulfate, N,N-dimethylethanolamonium hydrogen sulfate, N,N-dimethylethanolamonium acetate, N,N-dimethyletha-nolamonium glycolate, N,N-dimethylethanolammonium succinate, 1-ethyl-3-methylimidazolium acetate, 1-ethyl-3-methylimidazolium diethyl phosphate, 1-ethyl-3-methylimi-dazolium chloride, 1,3-dimethylimidazolium dimethyl phosphate, cholinium glycinate, and cholinium lysinate. In some embodiments, the ionic liquid medium optionally comprises a second component comprising an acid selected from the group consisting of hydrochloric acid, sulfuric acid, nitric acid, trifluoroacetic acid, and phosphoric acid. In some embodiments, the second component is present in the ionic liquid medium at about a 0.1 acid/biomass weight ratio.

In some embodiments, the dissolving step occurs at a temperature of about 140° C. to about 200° C. and/or for time of between about 60 and about 360 minutes.

In some embodiments, the hydrolyzing step occurs at a temperature of between about 95° C. and 125° C. for about two hours or occurs at about 95° C. for about 1 to about 6 hours and provides a yield of at least 25% glucose. In some embodiments, the hydrolyzing step occurs at a temperature of between about 95° C. and 120° C. for about two hours or occurs at about 95° C. for at least 2 hours and provides a yield of at least 40% glucose. In some embodiments, the hydrolyzing step is performed in the presence of an acid catalyst.

In some embodiments, the acid catalyst is a Lewis acid catalyst, optionally a Lewis acid catalyst selected from the group consisting of $CrCl_3.6H_2O$, $AlCl_3.6H_2O$, $ZrCl_4$, $SnCl_2$, $HfCl_4$, and $SnCl_4.5H_2O$.

In some embodiments, the cellulase digestion product is produced by pre-treating a softwood with an acid, optionally wherein the acid is selected from the group consisting of phosphoric acid ($H_3PO_4$), sulfuric acid, nitric acid, hydro-chloric acid, polyphosphoric acid, and trifluoroacetic acid, or any combination thereof, at a temperature and for a time sufficient to produce a pre-treated solid; adding a single or mixture of one or more anti-solvents, wherein the one or more anti-solvents are optionally selected from the group consisting of water, an alcohol, or a combination thereof, wherein the alcohol is optionally selected from the group consisting of ethanol, methanol, propanol, butanol, pentanol, hexanol, heptanol, octanol, or any combination thereof, in an amount sufficient to stop the treatment reaction; and recov-ering the pre-treated solid from the reaction, optionally wherein the recovering comprises centrifugation followed by removal of supernatant from the centrifuged reaction. In some embodiments, the acid is present at a concentration of from 10-100% (v/v).

In some embodiments, the pre-treating step is performed at a temperature of from about 20 to about 180° C. In some embodiments, the pre-treating step is performed for 24 hours or less.

In some embodiments, the presently disclosed methods further comprise washing the pre-treated solid one or more times with ethanol followed by one or more times with water.

In some embodiments, the presently disclosed methods further comprise neutralizing the pre-treated solids, option-ally with sodium carbonate.

In some embodiments, the temperature and the time sufficient to produce the pre-treated solid is calculated by the following equation:

$$\log R_o = \left[ t \cdot \exp\left(\frac{T - 100}{14.75}\right) \right]$$

where $R_o$ is the combined reaction temperature and time, and t and T are the pretreatment time in minutes and the temperature in ° C., respectively. The pretreatment tempera-ture and time can in some embodiments range from 50-180° C. and 0.1-24 hours, respectively. Varying pretreatment conditions affect the pretreatment efficiency, structure of the pretreated solids, and the resulting sugar yield.

In some embodiments of the presently disclosed methods, the hydrolysis comprises resuspending the pre-treated solids in 50 mM sodium citrate buffer at a pH of about 4.8, optionally at a concentration of 10 grams of glucan per liter (up to 100 g solid/L), and digesting the pre-treated solids with cellulase, hemicellulase, β-glucosidase, or a combina-tion thereof for a time and at a temperature sufficient to hydrolyze the glucan present in the pre-treated solids.

In some embodiments, the digesting step employs a mixture of cellulase and hemicellulase, optionally at a ratio of about 9:1 by weight. In some embodiments, the digesting step employs about 5 FPUs of cellulase and 10 units of β-glucosidase per gram of glucan or comprises about 15 FPUs of cellulase and 30 units of β-glucosidase per gram of glucan. In some embodiments, the digesting is at about 20-80° C. for at least 0.1 hours.

In some embodiments, after the digesting step, residual solids are removed by centrifugation followed by collecting centrifugation supernatant, optionally wherein the collected centrifugation supernatant is incubated about room tempera-ture for at least about 30 minutes to permit cellobiose present in the collected centrifugation supernatant to be converted to glucose by any enzyme remaining therein.

In some embodiments, the presently disclosed methods further comprise acidifying the collected centrifugation supernatant with an acid and freezing overnight to precipi-tate any remaining solids.

In some embodiments, the presently disclosed methods further comprise removing any precipitated solids by precipitation and recovering the supernatant, wherein the recovered supernatant is a sugar source.

In some embodiments, the presently disclosed methods produce a levulinic acid yield of at least about 40 mol %. In some embodiments, the levulinic acid yield is at least about 60 mol %.

Thus, it is an object of the presently disclosed subject matter to provide methods for preparing levulinic acid from various sugar sources in high yield.

An object of the presently disclosed subject matter having been stated hereinabove, and which is achieved in whole or in part by the presently disclosed subject matter, other objects will become evident as the description proceeds when taken in connection with the accompanying drawings as best described herein below.

BRIEF DESCRIPTION OF THE FIGURES

FIGS. 2A-2D show the effects of dissolution conditions on glucan conversion and glucose yield, including temperature (FIG. 2A) and time (FIG. 2B). The effects of acid hydrolysis conditions on glucan conversion and glucose yield with respect to temperature (FIG. 2C) and time (FIG. 2D) are also shown.

FIGS. 7A-7D depicts an exemplary process for treating a softwood with H$_3$PO$_4$. FIG. 7A is a schematic representation a process of the presently disclosed subject matter. FIG. 7B depicts the enzymatic hydrolysis of the pretreated softwood, and FIGS. 7C and 7D are graphs showing hydrolysis profiles of H$_3$PO$_4$-pretreated yellow pine samples (FIG. 7C) and Douglas fir (FIG. 7D) at 5 (squares) and 15 (circles) FPU/g glucan.

6

(wider light gray bars overlaying each pair of light and dark gray bars) after 72 hours with 5 FPU of cellulase and 10 units of β-glucosidase per gram of glucan.

Figure 11:
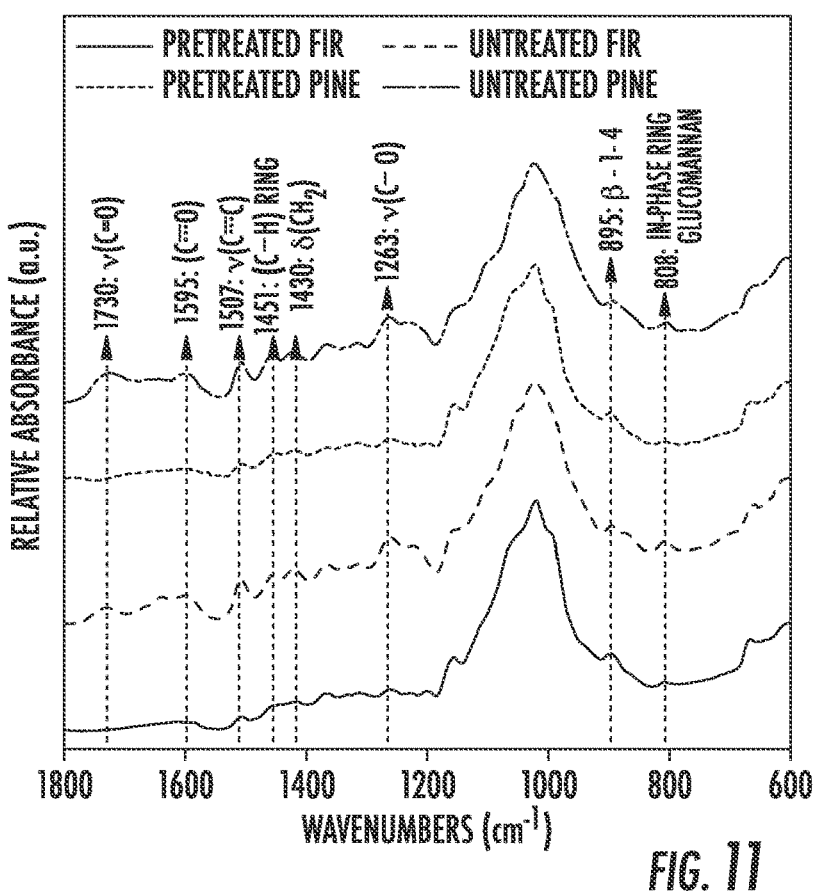

FIG. 11 is a series of FTIR spectra of yellow pine and Douglas fir before and after H$_3$PO$_4$ pretreatment. The top spectrum is the untreated pine, the one below that is the pretreated pine, below that is untreated fir, and the bottom spectrum is pretreated fir.

Figure 12:
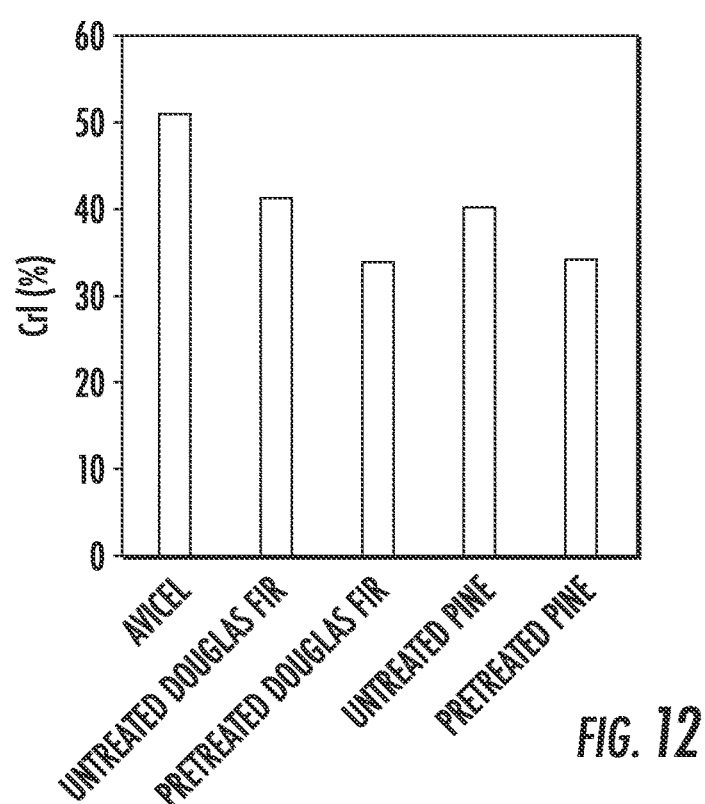

FIG. 12 is a bar graph of crystallinity index (CrI) of Avicel, untreated softwoods, and pretreated softwoods.

Figure 13:
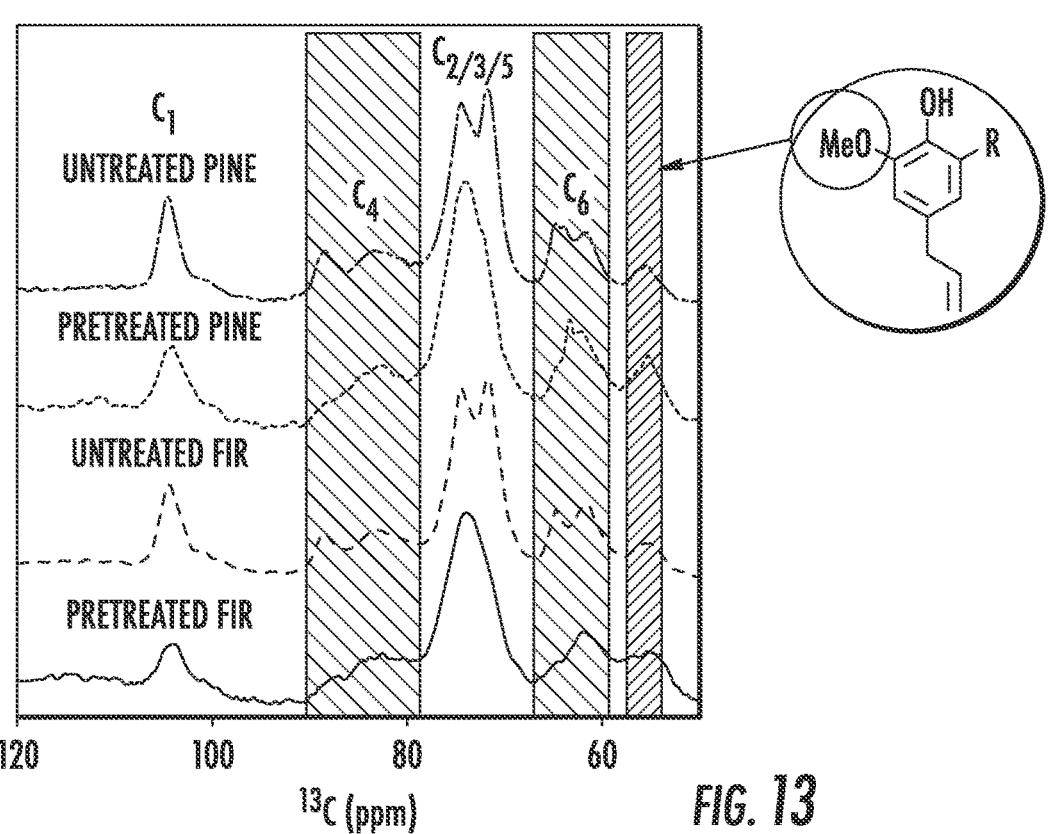

FIG. 13 is a series of CP/MAS $^{13}$C NMR spectra of yellow pine and Douglas fir samples before and after H$_3$PO$_4$ pretreatment.

Figure 14:
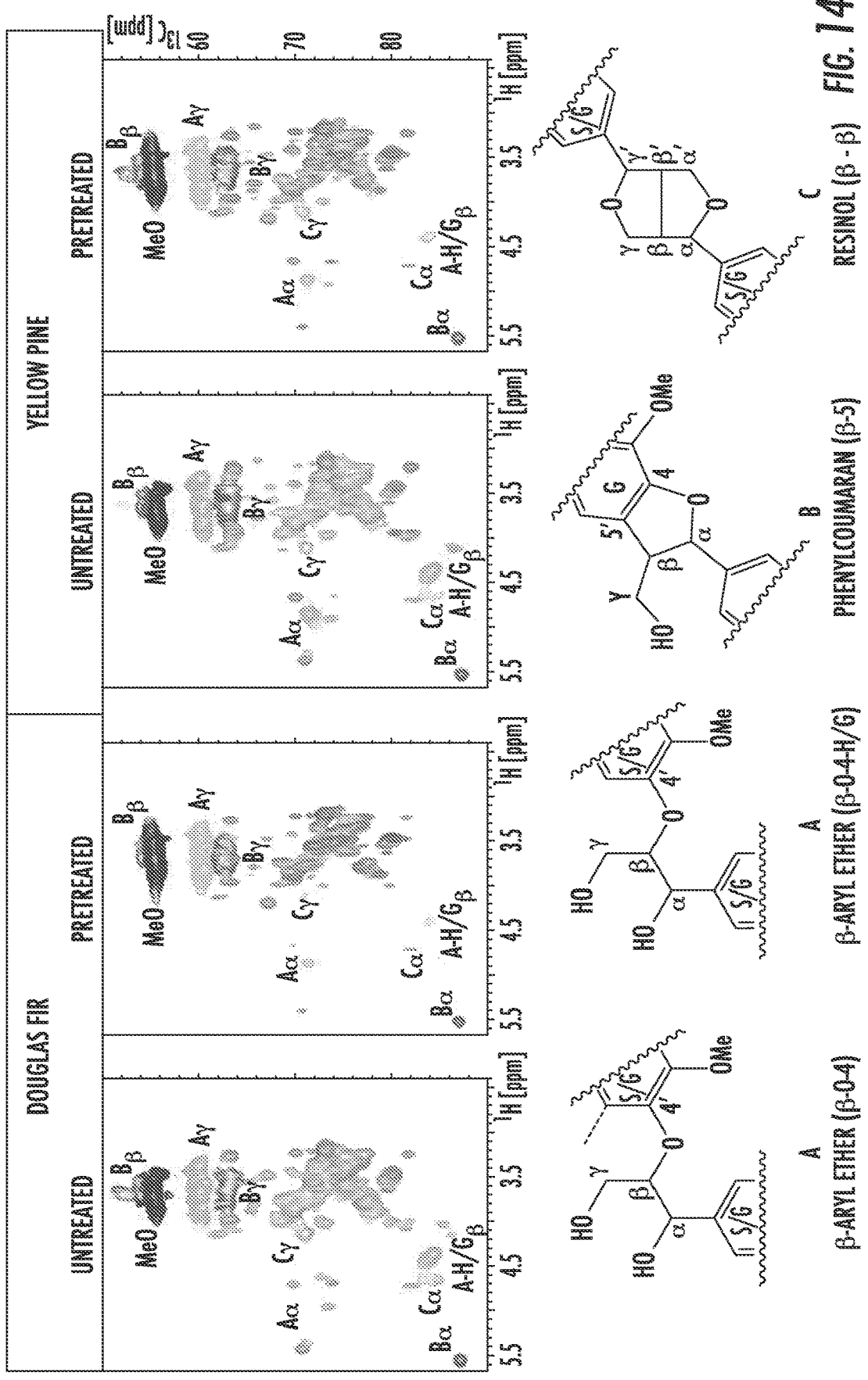

FIG. 14 is a series of 2D $^{13}$C-$^1$H HSQC NMR spectra in aliphatic region of Douglas fir and yellow pine before and after H$_3$PO$_4$ pretreatment.

Figure 15:
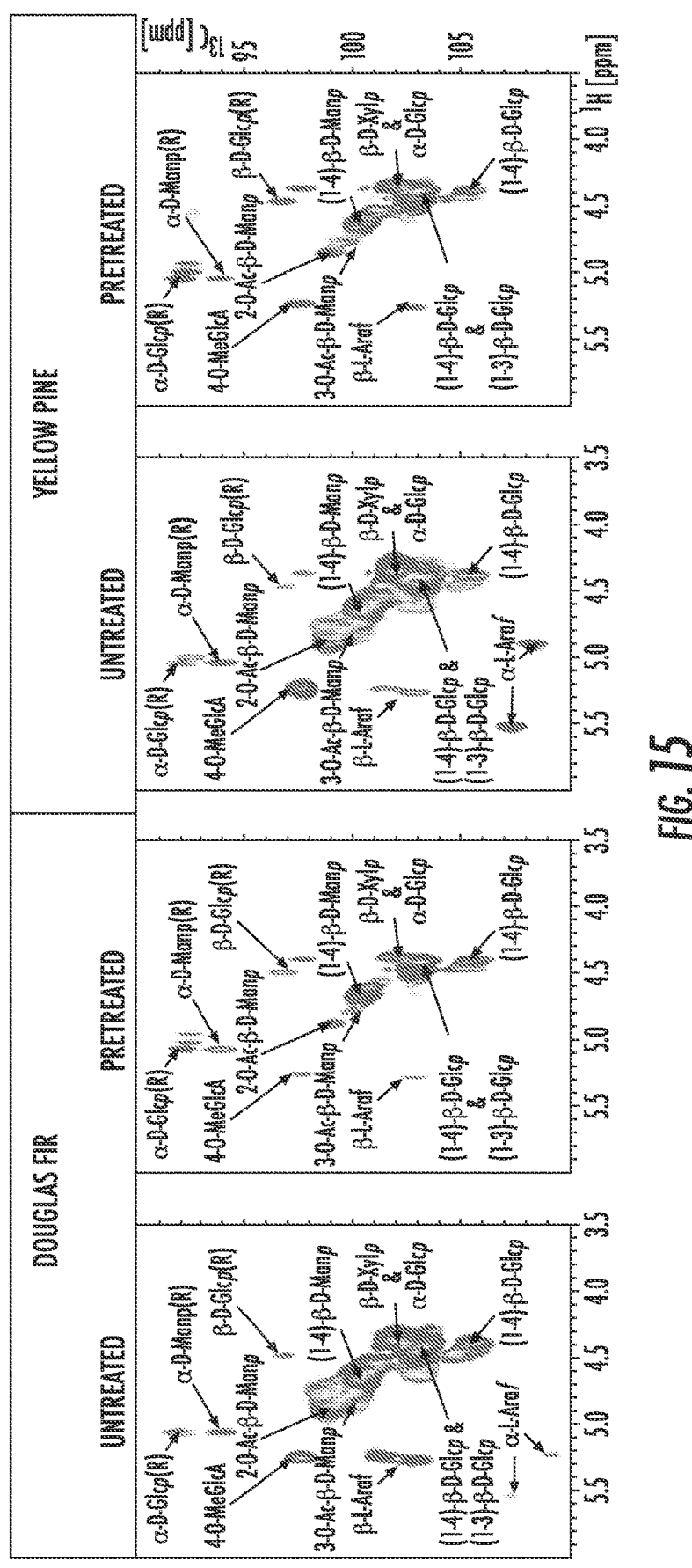

FIG. 15 is a series of 2D $^{13}$C-$^1$H HSQC NMR spectra in anomeric region of Douglas fir and yellow pine before and after H$_3$PO$_4$ pretreatment.

Figure 16:
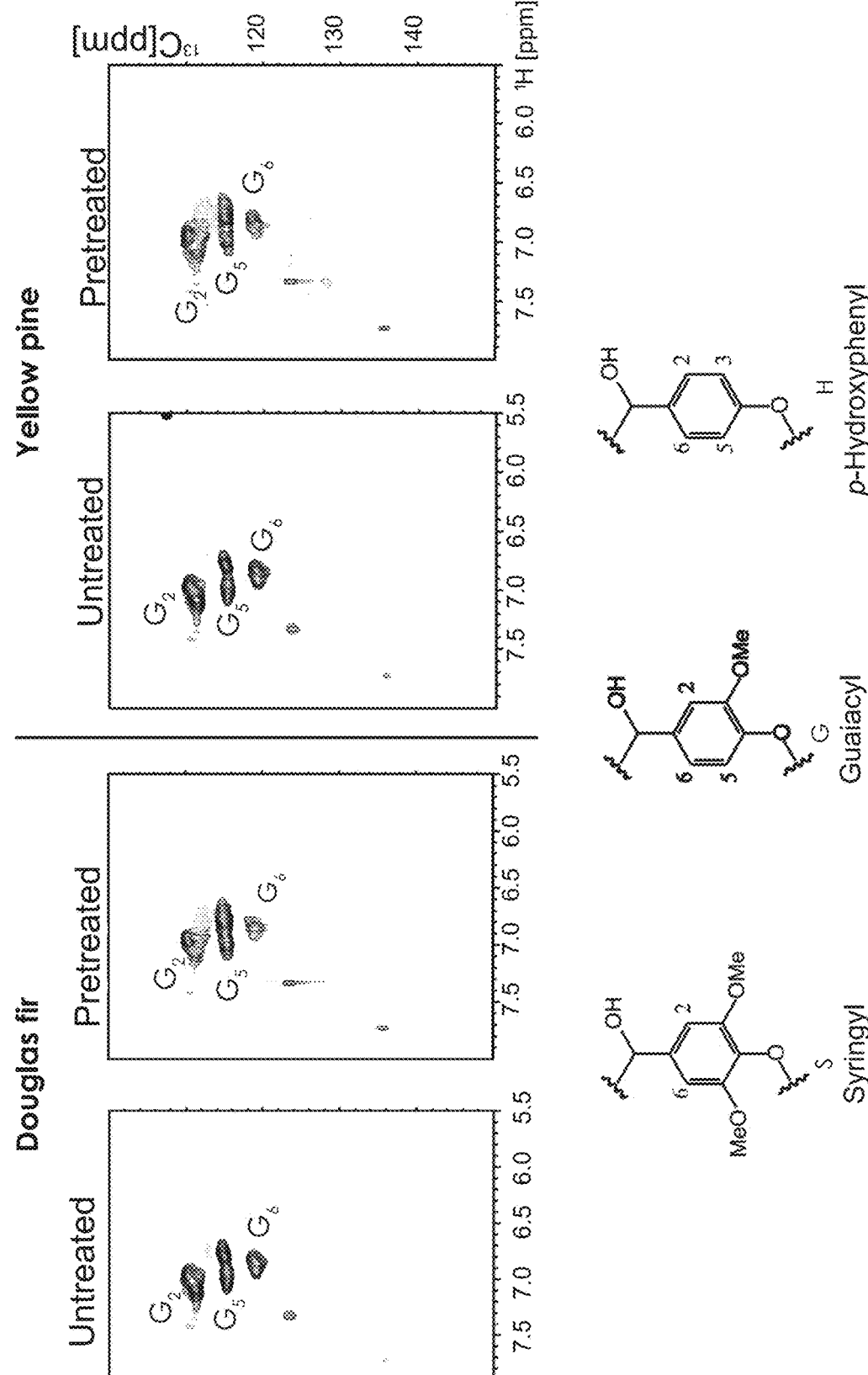

FIG. 16 is a series of 2D $^{13}$C-$^1$H HSQC NMR spectra in aromatic region of Douglas fir and yellow pine before and after H$_3$PO$_4$ pretreatment.

Figure 17:
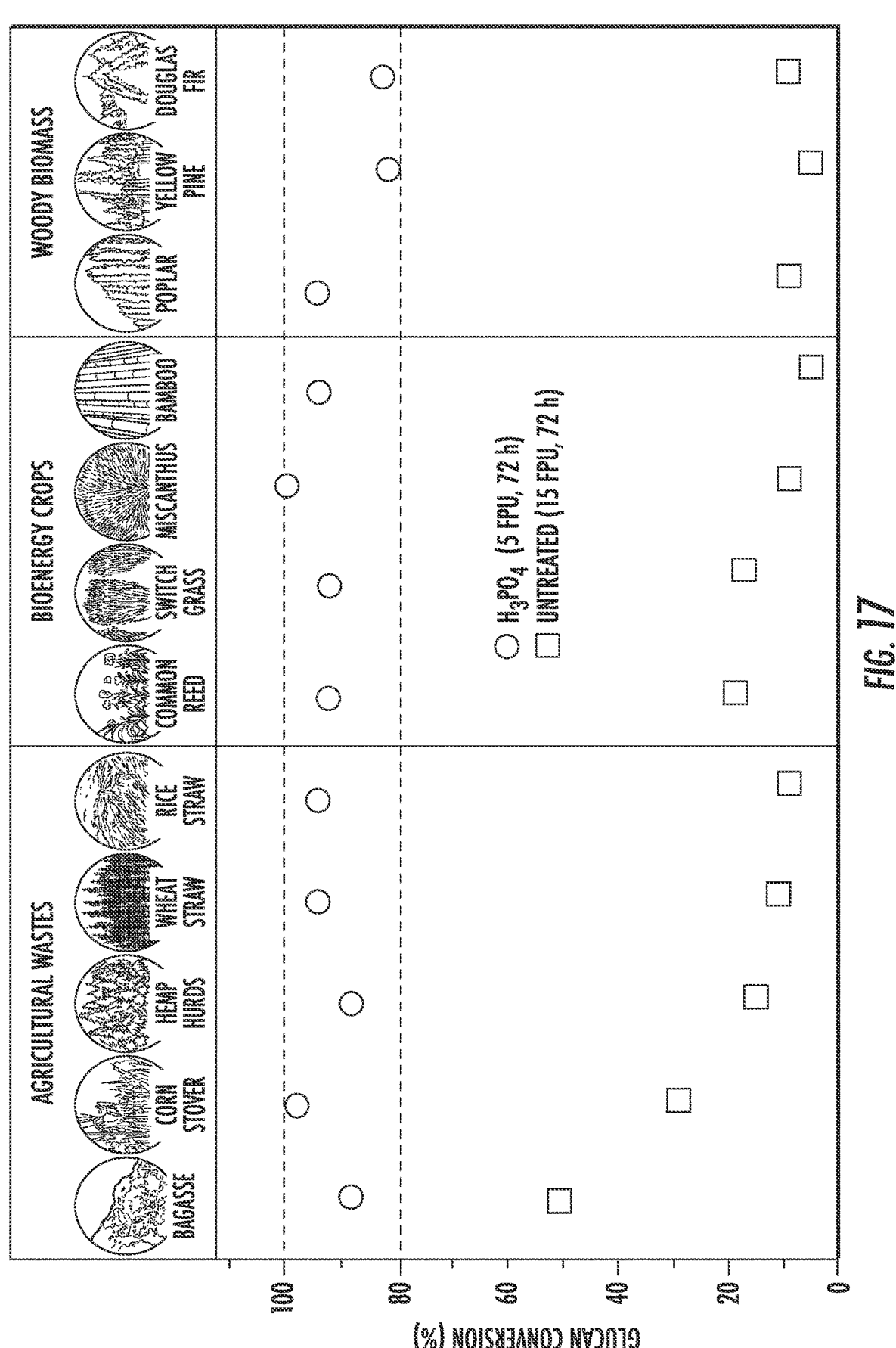

FIG. 17 is a plot showing that H$_3$PO$_4$ pretreatment accommodated many types of feedstocks—agricultural wastes, bioenergy crops, and woody biomass—as determined by glucan conversion percentages.

Figure 18:
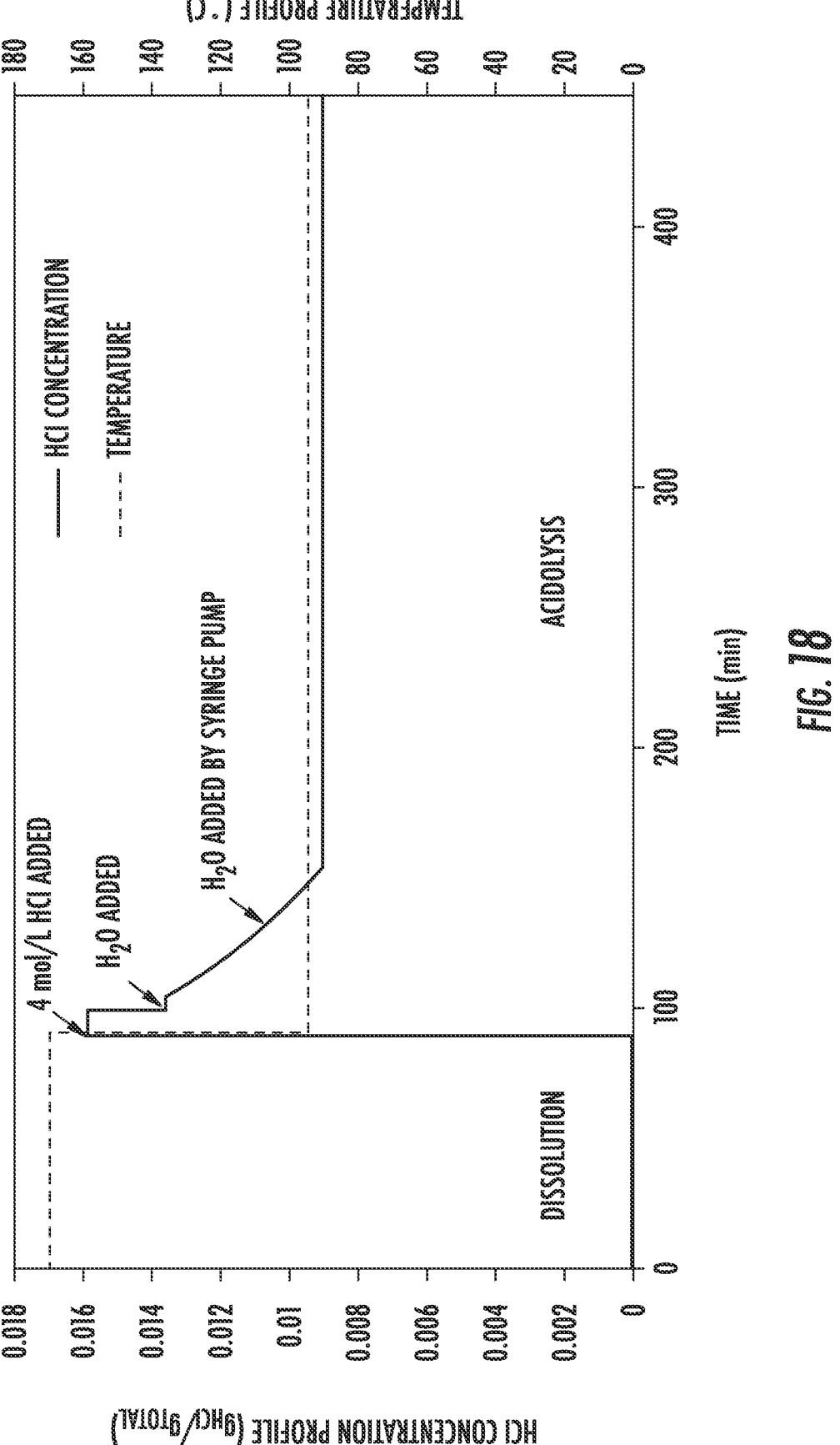

FIG. 18 is a graph of exemplary acid concentrations and temperature profiles used in the acid hydrolysis of hemp hurds in IL [C$_2$C$_1$im]Cl disclosed herein.

DETAILED DESCRIPTION

I. Definitions

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Furthermore, the terms first, second, third, and the like as used herein are employed for distinguishing between similar elements and not necessarily for describing a sequential or chronological order. It is to be understood that the terms so used are interchangeable under appropriate circumstances and that the subject matter described herein is capable of operation in other sequences than described or illustrated herein.

Following long-standing patent law convention, the articles "a", "an", and "the" refer to "one or more" when used in this application, including in the claims. For example, the phrase "a cell" refers to one or more cells. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to whole number values between 1 and 100 and greater than 100.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, term "comprising", which is synonymous with "including," "containing", or "characterized by", is inclusive or open-ended and does not exclude additional, unrecited elements and/or method steps. "Comprising" is a term of art used in claim language which means that the named elements are present, but other elements can be added and still form a composition or method within the scope of the presently disclosed subject matter.

As used herein, the phrase "consisting of" excludes any element, step, or ingredient that is not particularly recited in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting essentially of", and "consisting of", where one of these three terms is used herein, the presently disclosed and claimed subject matter encompasses the use of either of the other two terms. For example, "comprising" is a transitional term that is broader than both "consisting essentially of" and "consisting of", and thus the term "comprising" implicitly encompasses both "consisting essentially of" and "consisting of". Likewise, the transitional phrase "consisting essentially of" is broader than "consisting of", and thus the phrase "consisting essentially of" implicitly encompasses "consisting of".

II. Methods of the Presently Disclosed Subject Matter

Figure 1:
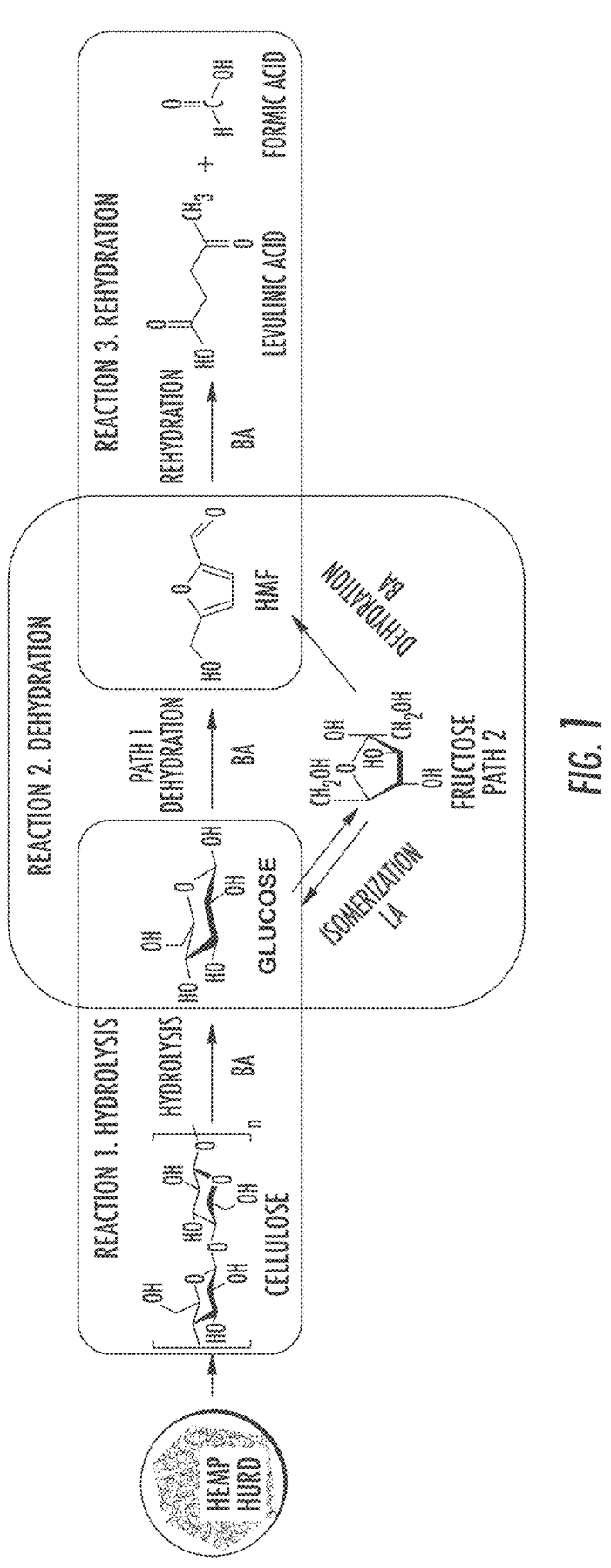
FIG. 1 is a schematic of a reaction cascade for the formation of levulinic acid from lignocellulose. Cellulose undergoes hydrolysis to glucose (reaction 1), glucose dehydration to HMF (reaction 2), and HMF rehydration to levulinic acid (reaction 3). BA=Brønsted acid; LA=Lewis acid.

Levulinic acid, a versatile platform chemical, can be produced chemically from renewable cellulosic biomass. The presence of carboxylic and carbonyl functional groups makes it easy to derivatize levulinic acid into forms for production of fuels, fuel additives, pharmaceuticals, plasticizers, solvents, flavoring agents, and cosmetics (Serrano-Ruiz et al., 2010; Braden et al., 2011; Christensen et al., 2011; Windom et al., 2011; Wright et al., 2012; Cao et al., 2014; Morone et al., 2015; Pileidis & Titirici, 2016; Wang et al., 2016; Hu et al., 2017). Levulinic acid is produced from cellulosic biomass by three sequential reactions (see FIG. 1): (Reaction 1) cellulose hydrolysis to glucose; (Reaction 2) glucose dehydration to 5-hydroxymethyl furfural (HMF); and (Reaction 3) HMF hydrolysis to levulinic acid with formic acid as a by-product (Horvat et al., 1985; Girisuta et al., 2006; Son et al., 2012). These reactions are typically catalyzed by Brönsted acids.

The major challenge in the conversion of cellulosic biomass comes from the poor solubility of the biomass in any reaction medium due to the abundant hydrogen bonding networks within its structure (Rinaldi & Schüth, 2009; Binder & Raines, 2010). This condition hinders reactant accessibility to active sites. Thus, a harsh reaction condition is normally used to promote the limited biomass-catalyst interaction. We have shown that dissolution of cellulose in 1-butyl-3-methylimidazolium chloride ([$C_4C_1$im]Cl) enhances its accessibility to HCl. The dissolved cellulose can be hydrolyzed to produce sugars under a mild reaction condition (120-160° C. and atmospheric pressure; Sun et al., 2013; Sun et al., 2015). The additional Lewis acid catalysts show the synergistic effect, enabling conversion of resulting glucose from corn stover in [$C_2C_1$im]Cl to HMF and levulinic acid (Binder & Raines, 2009).

As such, in some embodiments the presently disclosed subject matter provides methods for producing levulinic acid from a sugar source that comprise providing a sugar source, wherein the sugar source comprises a hydrolysis product produced by hydrolyzing a cellulose-rich product generated from hemp hurds and/or comprises a cellulase digestion product of softwood pre-treated with phosphoric acid ($H_3PO_4$); dehydrating glucose present in the sugar source, and/or fructose resulting from isomerization of glucose present in the sugar source, to produce 5-hydroxymethyl furfural (HMF); and hydrolyzing the HMF to levulinic acid. Any sugar source can be employed, as exemplified herein by hemp hurds and acid-treated softwoods.

II.A. Preparation of Levulinic Acid from Hemp Hurds

Provided herein is a one-pot acid-catalyzed levulinic acid production from lignocellulosic biomass includes (1) cellulose dissolution in ionic liquid enhances acid hydrolysis of dissolved cellulose to glucose (2) levulinic acid production from glucose-rich hydrolysate. In some embodiments, under optimum conditions of temperature and time, at least 40%, 50%, 60%, 70%, 80%, or more of glucose is obtained. The glucose-rich hydrolysate is then subject to second step to convert glucose to levulinic acid. During these steps, the process is operated in one-pot without separation intermediates.

More particularly, in some embodiments the presently disclosed subject matter relates to methods for producing levulinic acid from hemp hurds, wherein the methods comprise dissolving hemp hurds in an ionic liquid medium to produce a cellulose-rich product; hydrolyzing cellulose present in the cellulose-rich product to produce a glucose-rich product; dehydrating glucose present in the glucose-rich product, and/or fructose resulting from isomerization of the glucose, to produce 5-hydroxymethyl furfural (HMF); and hydrolyzing the HMF to levulinic acid. Various ionic liquid media can be employed for the presently disclosed method. In some embodiments, the ionic liquid medium comprises 1-ethyl-3-methylimidazolium chloride ([$C_2C_1$im]Cl) and hydrochloric acid at about a 0.1 HCl/Biomass weight ratio. However, other ionic liquid media can also be employed, including but not limited to 1-ethyl-3-methylimidazolium chloride ([$C_2C_1$im]Cl), 1-butyl-3-methylimidazolium chloride, 1-butyl-3-methylimidazolium hexafluorophosphate, 1-butyl-3-methylimidazolium acetate, 1-butyl-1-methylpyrrolidinium chloride, 1-butyl-3-methylimidazolium methylsulfate, N,N-dimethylethanolamonium hydrogen sulfate, N,N-dimethylethanolamonium acetate, N,N-dimethylethanolamonium glycolate, N,N-dimethylethanolammonium succinate, 1-ethyl-3-methylimidazolium acetate, 1-ethyl-3-methylimidazolium diethyl phosphate, 1-ethyl-3-methylimidazolium chloride, 1,3-dimethylimidazolium dimethyl phosphate, Cholinium glycinate, and Cholinium lysinate. Similarly, other acids besides HCl can be employed, including but not limited to sulfuric acid, nitric acid, trifluoroacetic acid, and phosphoric acid.

The parameters that can be employed with respect to the ionic liquid medium, the reaction time, and the reaction temperature can be modified based on the desired degree to which the hemp hurds should be treated. For example, in some embodiments the dissolving step occurs at a temperature of about 140° C. to about 200° C. and/or for time of between about 60 and about 360 minutes. Other temperatures and times can also be employed, such as but not limited to hydrolysis at a temperature of between about 95° C. and 125° C. for about two hours, or at about 95° C. for about 1 to about 6 hours, or any other temperature and time frame that provides an acceptable degree of release of sugar from the hemp hurds. By way of example and not limitation, the time, temperature, and ionic liquid medium components can be adjusted as necessary such that a yield of at least 20%, 25%, 3%, 35%, 40%, 45%, 50%, 60%, 70%, 80%, or greater than 80% glucose is produced.

In some embodiments, the hydrolyzing step is performed in the presence of an acid catalyst. Any acid catalyst can be employed. By way of example and not limitation, a Lewis acid can be employed as an acid catalyst. Lewis acids are known to those of skill in the art, examples of which include but are not limited to $CrCl_3.6H_2O$, $AlCl_3.6H_2O$, $ZrCl_4$, and $SnCl_4.5H_2O$.

The presently disclosed methods can produce levulinic acid yields of in some embodiments at least about 40 mol %, in some embodiments at least about 45 mol %, in some embodiments at least about 50 mol %, in some embodiments at least about 55 mol %, and in some embodiments at least about 60 mol %.

II.B. Acid Treatment of Softwoods

Figure 6:
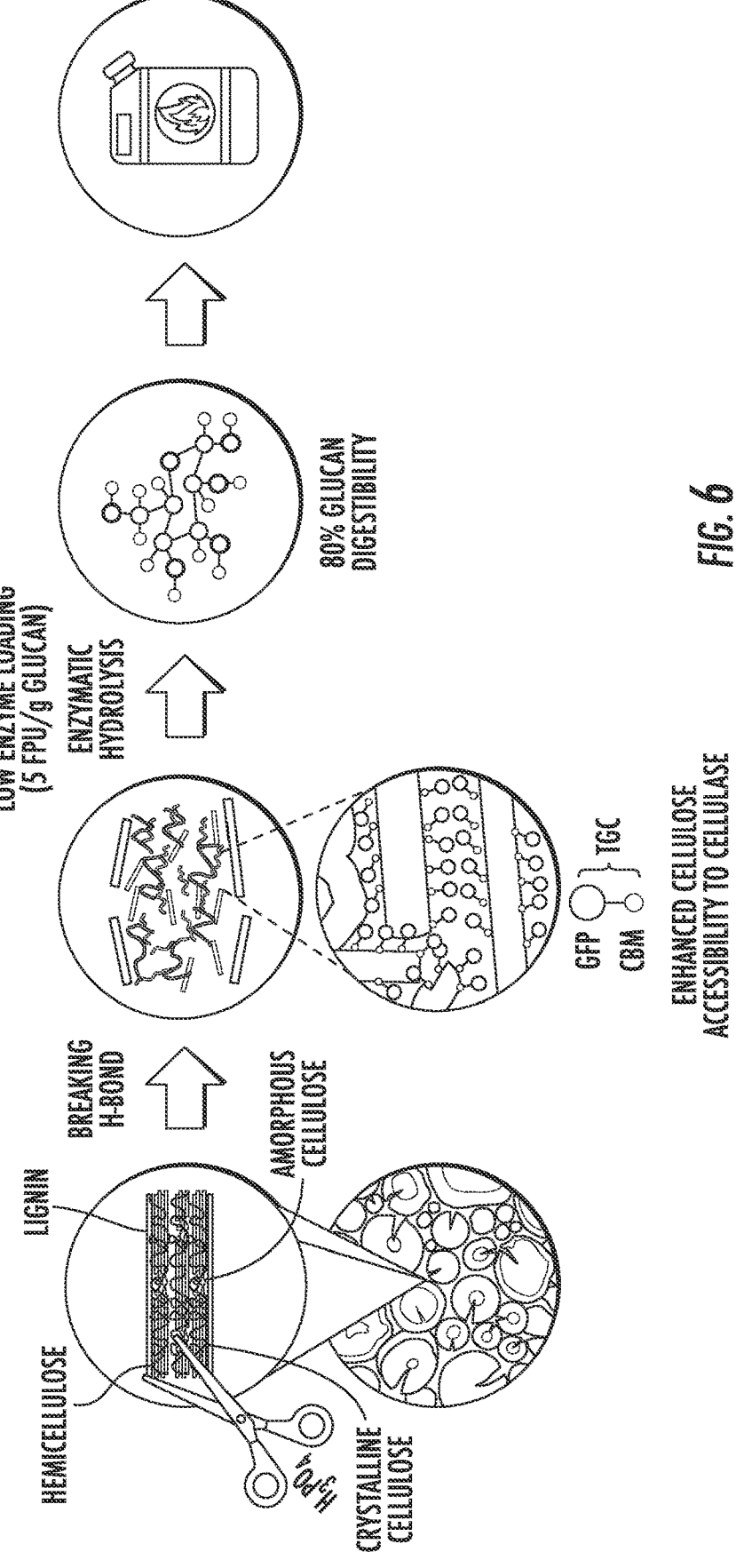
FIG. 6 is a schematic representation of a process for producing a high sugar product from softwood.
Figure 7A:
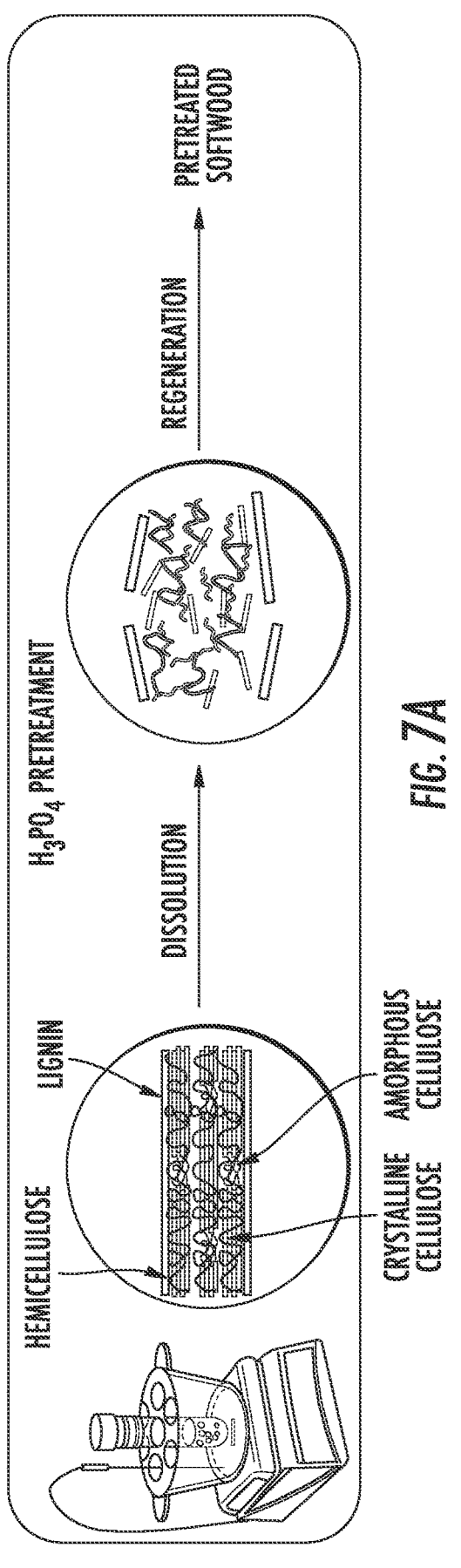

In some embodiments, the sugar that is employed to produce the levulinic acid is from a source other than hemp hurds. Any source that comprises or can be modified to comprise hydrolysable sugar (e.g., glucose and/or fructose) can be employed. In some embodiments, the sugar source is produced by acid treatment of a softwood. An exemplary process for producing a sugar source from a softwood is shown in FIG. 6.

The guaiacyl (G)-type lignin monomer is the main lignin monomer in softwoods (Stevanovic, 2016). The G-type lignin monomer has a $C_4$ atom available to form a bond with other G-type lignin monomer units, creating highly cross-linked lignin. The crosslinked lignin is a strong glue that seals the cellulose from enzymes and catalysts during upgrading (Kishimoto et al., 2010; Alvarez-Vasco & Zhang, 2013; Anwar et al., 2014; Wagner et al., 2015; Nitsos et al., 2016; Alvarez et al., 2016; Nitsos et al., 2018). Thus, typically, some types of pretreatment are required to provide cellulose accessibility to enzymes (Mes-Hartree & Saddler, 1983; Rajan & Carrier, 2014) to unlock sugars from lignocellulosic biomass (Yang & Wyman, 2008). For softwoods, severe pretreatment (e.g., 180-280° C.) conditions are needed to expose cellulose to enzymes. These conditions present three challenges: (1) sugar degradation, (2) a requirement for high enzyme loadings due to the generation of inhibitors (furfural, 5-hydroxymethylfurfural (IMF), acetic acid, levulinic acid, and formic acid; see e.g., Mes-Hartree & Saddler, 1983; Soderstrom et al., 2002; Sipos et al., 2009; Hall et al., 2010; Shuai, 2010; Anwar et al., 2014; Normark et al., 2014; Rajan & Carrier, 2014; Zhang et al., 2016), and (3) difficulty in further lignin utilization due to lignin condensation (Nguyen et al., 2000; Sun et al., 2018). Solving these challenges is important for the economics of softwood biorefineries.

Cellulose solvents, including $H_3PO_4$ and various types of ionic liquids, are effective at lignocellulose dissolution/pretreatment. The dissolution of lignocellulose unglues the lignocellulose components by disrupting the lignin-carbohydrate complex (LCC) linkages, and it decrystallizes the highly ordered cellulose structure by disrupting the intra/intermolecular hydrogen bonds between cellulose chains. Decrystallization of cellulose enhances its accessibility to acid/enzymes, enabling high glucan digestibility and fast hydrolysis rates with low enzyme loading (Szijártó et al., 2008; Hall et al., 2010). In particular, pretreatment with the cellulose solvent $H_3PO_4$ (85%) breaks inter/intramolecular hydrogen bonds within lignocellulose and between cellulose chains under a mild condition (<60° C. and atmospheric pressure; Sathitsuksanoh et al., 2011; Satari et al., 2019). Thus, $H_3PO_4$ pretreatment has been explored recently for agricultural wastes, bioenergy crops, and hardwoods (Hewetson et al., 2016; Siripong et al., 2016; Nair et al., 2017; Wu et al., 2018; Yu et al., 2019). The pretreated lignocellulose samples had high glucan digestibilities of >73% with a low enzyme loading of 5 filter paper units (FPU) of enzyme/g glucan (Moxley et al., 2008; Li et al., 2009; Sathitsuksanoh et al., 2011). Various strategies have been developed to recycle these cellulose solvents (Sathitsuksanoh et al., 2015; McDonald et al., 2017). Although $H_3PO_4$ pretreatment is effective at pretreating lignocellulose, its impact on softwoods and residual lignin after has not been assessed adequately.

As disclosed herein, in some embodiments $H_3PO_4$ (e.g., 85%) pretreatment at 50° C. and atmospheric pressure for <2 hours on southern yellow pine and Douglas fir, followed by enzymatic hydrolysis is described. Pretreated pine and Douglas fir had high glucan digestibility of ~80% with a low cellulase loading (5 FPUs/g glucan). We used a fusion protein to mimic and quantitate adsorption of cellulase enzymes onto the lignocellulose, cross-polarization/magic angle spin (CP/MAS) 13C-nuclear magnetic resonance (NMR), and Fourier-transform infrared (FTIR) spectroscopy to characterize changes in the degree of crystallinity, and 2D $^{13}C$-$^1H$ heteronuclear single quantum coherence (HSQC) NMR spectroscopy to elucidate changes in chemical structure of lignin after $H_3PO_4$ pretreatment. $H_3PO_4$ pretreatment enhanced cellulose accessibility to cellulase. The process disrupted LCC linkages and the highly ordered hydrogen bonds of cellulose, thereby reducing the degree of crystallinity. The pretreated materials became more amorphous compared with the untreated biomass. Moreover, this process did not modify lignin, enabling its potential profitable use in biorefineries.

Thus, in some embodiments the presently disclosed methods employ cellulase-digested softwoods as a sugar source. In some embodiments, the cellulase digestion product is produced by pre-treating a softwood with an acid, optionally wherein the acid is selected from the group consisting of phosphoric acid ($H_3PO_4$), sulfuric acid, nitric acid, hydrochloric acid, polyphosphoric acid, and trifluoroacetic acid, or any combination thereof, at a temperature and for a time sufficient to produce a pre-treated solid; adding a single or mixture of one or more anti-solvents, wherein the one or more anti-solvents are optionally selected from the group consisting of water, an alcohol, or a combination thereof, wherein the alcohol is optionally selected from the group consisting of ethanol, methanol, propanol, butanol, pentanol, hexanol, heptanol, octanol, or any combination thereof, in an amount sufficient to stop the treatment reaction; and recovering the pre-treated solid from the reaction, optionally wherein the recovering comprises centrifugation followed by removal of supernatant from the centrifuged reaction.

As with the methods described herein above, the reaction conditions under which the softwoods are pre-treated can be adjusted with respect to acid concentration, time, and temperature in order generate acceptable high levels of access of the cellulose present in the softwood to digestive enzymes. By way of example and not limitation, in some embodiments the acid is present at a concentration of from 10-100% (v/v). Similarly, in some embodiments the pre-treating step is performed at a temperature of from about 20 to about 180° C., and/or the pre-treating step is performed for 24 hours or less. In some embodiments, the pretreatment temperature selected is between 50-180° C. and the time is between 0.1 and 24 hours. Varying pretreatment conditions affect the pretreatment efficiency, structure of the pretreated solids, and the resulting sugar yield.

Once the softwood has been pre-treated, the presently disclosed methods can further comprise washing the pre-treated solids that result in order to remove unwanted impurities and/or to change the solution in which the pre-treated solids are present. Exemplary washing steps include one or more washes with ethanol followed by one or more washes with water. If desired, the pre-treated solids can be neutralized, optionally with a solution of sodium carbonate.

In some embodiments, the temperature and the time sufficient to produce the pre-treated solid is calculated using the following equation:

$$\log R_o = \left[ t \cdot \exp\left( \frac{T - 100}{14.75} \right) \right]$$

where $R_o$ is the combined reaction temperature and time, and t and Tare the pretreatment time in minutes and the temperature in ° C., respectively. By way of example and not limitation, in some embodiments the hydrolysis comprises resuspending the pre-treated solids in 50 mM sodium citrate buffer at a pH of about 4.8, optionally at a concentration of 10 grams of glucan per liter (up to 100 g solid/L), and digesting the pre-treated solids with cellulase, hemicellulase, β-glucosidase, or a combination thereof for a time and at a temperature sufficient to hydrolyze the glucan present in the pre-treated solids.

While not wishing to be bound by any particular theory of operation, one goal of the pre-treatment step is to enhance access to cellulose present in the softwood to enzymes that can break down the cellulose. By way of example and not limitation, in some embodiments a mixture of cellulase and hemicellulase, optionally at a ratio of about 9:1 by weight, can be employed. These enzymes are commercially available, including the CELLIC® brand CTec2 and HTec2 enzymes sold by Novozymes (Franklinton, North Carolina, United States of America).

Alternatively, cellulase and β-glucosidase can be employed for the enzymatic digestion of pre-treated softwoods. By way of example and not limitation, the digesting can employ about 5-15 filter paper units (FPUs) of cellulase and 10-30 units of 3-glucosidase per gram of glucan (see e.g., U.S. Pat. No. 5,916,780, incorporated herein by reference in its entirety). In some embodiments, the digesting is at about 20-80° C. for at least 0.1 hours.

After the digesting step, residual solids can be removed so that further processing of the pre-treated softwoods can be performed. By way of example and not limitation, residual solids can be removed by centrifugation. After centrifugation, the centrifugation supernatant, which contains the digestion products of the cellulose. In some embodiments, cellobiose can be present in the collected centrifugation supernatant, and incubating the collected centrifugation supernatant for at least about 30 minutes at room temperature can permit the cellobiose present to be converted to glucose by action of digestive enzymes action that also remain in the collected centrifugation supernatant.

If desired, the collected centrifugation supernatant can be acidified with an acid, and any additional remaining solids can be removed by freezing the acidified collected centrifugation supernatant (e.g., overnight at −20° C.), which results in the precipitation of some or all of the remaining solids. These precipitated solids can also be removed, for example, by centrifugation followed by recovery of the new centrifugation supernatant. This new centrifugation supernatant can then be employed as a sugar source for conversion to 5-hydroxymethyl furfural (HMF) by dehydration followed by hydrolysis of the HMF to levulinic acid as disclosed herein.

EXAMPLES

The following EXAMPLES provide illustrative embodiments. In light of the present disclosure and the general level of skill in the art, those of skill will appreciate that the following EXAMPLES are intended to be exemplary only and that numerous changes, modifications, and alterations can be employed without departing from the scope of the presently disclosed subject matter.

Materials and Methods for Examples 1-3

Materials. Hemp stalks and stems were provided by Green Remedy, Inc. (Louisville, Kentucky, USA). They were processed by a Vitamix blender (Cleveland, Ohio, USA). Processed hemp hurds were sieved to ~1-2 mm (18-10 mesh), separated, designated as 2 mm-hemp hurd, and used for all experiments. The 1-ethyl-3-methylimidazolium chloride ([$C_2C_1$im]Cl), hydrochloric acid (HCl), sulfuric acid ($H_2SO_4$), and Beechwood xylan were purchased from Sigma-Aldrich (St. Louis, Missouri, USA). AVICEL® PH 101 brand cellulose powder was a gift from FMC Biopolymers (Philadelphia, Pennsylvania, USA) and was used as received. All chemicals were analytical grade, unless otherwise noted. Kraft lignin (INDULIN AT® brand) was donated by Meadwestvaco Corp. (Richmond, Virginia, USA). Regenerated amorphous cellulose (RAC) was synthesized from AVICEL® by a published procedure (Zhang et al., 2006). RAC represents amorphous cellulose. Beechwood xylan and kraft lignin represented hemicelluloses and lignin in untreated hemp hurds and were used as controls for characterizations.

Compositional Analysis of Hemp Hurd and Reaction Product Determination. Hemp hurd, a type of lignocellulosic biomass, contains glucans (mostly cellulose), hemicelluloses, and lignin. The compositions of untreated hemp hurd, regenerated hemp hurd, and residual solids after dissolution-enhanced acid hydrolysis were determined by the laboratory analytical procedures (LAPs) offered by the National Renewable Energy Laboratory (NREL) as described elsewhere (references 32,33). All resulting monomeric sugars were analyzed by high-performance liquid chromatography (HPLC, Agilent Technology, Santa Clara, California, USA) equipped with a refractive index detector (RID) and diode array detector (DAD). The Aminex HPX-87H column (300× 7.8 mm², Bio-Rad, Hercules, California, USA) was used to separate monomeric sugars at 60° C. with 0.6 mL/min of 4 mmol/L $H_2SO_4$ as a mobile phase. Monomeric sugars were calibrated against certified standards (Absolute Standards Inc., Hamden, Connecticut, USA). Concentrations of monomeric sugars were determined by the peak area from the RID signals (HMF and furfural were determined by DAD signals at 280 nm). Concentrations of resulting monomeric sugars (glucose, xylose, and arabinose) to polymeric sugars (glucan, xylan, and arabinan) were expressed using an anhydro correction factor of 0.88 (from 132 to 150) for C-5 sugars (xylose and arabinose) and 0.90 (from 162 to 180) for C-6 sugars (glucose) (reference 32).

Acid hydrolysis of Hem Hurd in IL $[C_2C_1im]Cl$ and Reaction Product Determination. Hemp hurds dissolution was performed by mixing—mm-hemp hurds (17.5 wt. %) with $[C_2C_1im]Cl$ in a pressure tube (Ace Glass Inc., Vineland, New Jersey, USA). The reaction mixture was investigated at various dissolution temperatures (140-200° C.) and times (1-6 hours). To understand the effect of dissolution temperature on glucan conversion and glucose yield, the dissolution time was kept constant at two hours, unless otherwise noted. After the dissolution of hemp hurd, the slurries were cooled to the desired temperature of acid hydrolysis and equilibrated for 15 minutes prior to acid hydrolysis.

Acid hydrolysis of hemp hurd slurries was performed as described with some modifications (Binder & Raines, 2010; Sun et al., 2013). FIG. 18 shows the acid concentration and temperature profiles of the dissolution-enhanced acid hydrolysis process. In short, the hemp hurd slurries were hydrolyzed by 4M HCl at various temperatures (95-125° C.) and times (1-6 hours). HCl was selected as the acid catalyst to avoid anion exchange with the IL $[C_2C_1im]Cl$. In all experiments, the ratio of acid to feedstock (HCl to lignocellulose) was 0.10, g HCl/g lignocellulose. After dissolution and 15 minutes equilibration, HCl was added to the slurry to initiate acid hydrolysis of the cellulose. After 10 minutes, deionized water was added to obtain a final water concentration of 1.06 g $H_2O$/g biomass. After 15 minutes, a syringe pump was used to progressively add water to dilute the acid concentration during the course of 45 minutes (final water concentration=4.48 g $H_2O$/g biomass) to minimize sugar degradation. This progressive addition of water also slowed the formation of HMF and minimized the formation of undesirable humin polymers. (Dee & Bell, 2011). Water interacts with acidic protons more strongly than it interacts with the 2-OH of glucose, thereby slowing the formation of HMF. The formation of humin proceeds by the condensation of HMF with glucose. With less HMF formation from the progressive addition of water, the humin formation is minimized. Acid hydrolysis slurry continued to react for various hydrolysis times (1-6 hours) and was quenched in an ice bath. The slurry was centrifuged and filtered to separate the liquid and residual solid material. The liquid sample was analyzed by the High-Performance Liquid Chromatography (HPLC, Agilent Technology, Santa Clara, California, USA) to quantify the yield of glucan (glucose equivalent) and other reaction products (e.g., 5-hydroxymethylfurfural (HMF) and levulinic acid).

The residual solid was washed with 50 mL deionized water to remove soluble sugars and residual IL $[C_2C_1im]Cl$ prior to freeze-drying overnight. The composition of the residual solid was then analyzed to construct the mass balance. The concentrations of reaction products were determined by HPLC equipped with RID and DAD. The peak areas from the RID and DAD signals were used to determine concentrations of corresponding monomeric sugars and reaction products. All experiments and analyses were performed in triplicate and the standard deviation was less than 15%. Glucan conversion and product yields (% of theoretical maximum) were calculated based on the basis of initial glucan content in hemp hurd as follows:

$$\text{glucan conversion (\%)} = \frac{\text{mole of glucan converted}}{\text{mole of } glucan_{initial}} \times 100\%$$

$$\text{product yield (\%)} = \frac{\text{mole of product generated}}{\text{mole of } glucan_{initial}} \times 100\%$$

Mass Balance of the Acid-Catalyzed Conversion of Hemp Hurd to Levulinic Acid in IL $[C_2C_1im]Cl$. The optimal condition for acid-catalyzed conversion of hemp hurd to levulinic acid was used to construct the mass balance of this proposed process to elucidate changes in reaction products from different processing streams. This process consisted of (1) acid hydrolysis of hemp hurd in IL $[C_2C_1im]Cl$ and (2) glucose dehydration and HMF rehydration. The mass balance was constructed on the basis of 100 kg dried hemp hurd in all liquids and solid streams. The detailed procedure was shown as follows:

The acid-catalyzed conversion of hemp hurd to levulinic acid in $[C_2C_1im]Cl$ had two sequential steps: (1) acid hydrolysis of hemp hurd in IL $[C_2C_1im]Cl$, and (2) glucose dehydration and HMF rehydration. Our optimal reaction conditions were 17.5 wt % biomass loading, 170° C. and 1.5 hours for acid hydrolysis of hemp hurd in IL $[C_2C_1im]Cl$ and 95° C. for 6 hours for dehydration and rehydration of the resulting glucose to levulinic acid. The mass balance on the basis of 100 kg dried hemp hurd in five streams (FIG. 5) as follows:

Stream 1: Hemp hurd consisted of 34 wt % glucan, 15.4 wt % xylan, 0.6 wt % arabinan, 21.1 wt % lignin and 28.9 wt % others (e.g., protein, wax, and extractives).

$$\text{Initial glucan (kg)} = 100 \text{ kg hemp hurds} \times \frac{34 \text{ kg glucan}}{100 \text{ kg hemp hurds}} = 34.0 \text{ kg}$$

$$\text{Initial xylan (kg)} = 100 \text{ kg hemp hurds} \times \frac{15.4 \text{ kg xylan}}{100 \text{ kg hemp hurds}} = 15.4 \text{ kg}$$

Initial arabinan (kg) =

$$100 \text{ kg hemp hurds} \times \frac{0.6 \text{ kg arabinan}}{100 \text{ kg hemp hurds}} = 0.6 \text{ kg}$$

$$\text{Initial lignin (kg)} = 100 \text{ g hemp hurds} \times \frac{15.4 \text{ g lignin}}{100 \text{ g hemp hurds}} = 15.4 \text{ kg}$$

We used 17.5 wt % hemp hurd loading (in IL $[C_2C_1im]Cl$):

Initial $[C_2C_1im]Cl$ (kg) =

$$\frac{100 \text{ kg hemp hurd} \times 82.5 \text{ kg } [C_2C_1im]Cl}{17.5 \text{ kg hemp hurds}} = 471 \text{ kg}$$

Stream 2: After hemp hurd dissolution, we added dilute HCl (4 mol/L) and water to hydrolyze dissolved hemp hurd to glucose. The final concentration of HCl and water were 0.10 kg HCl/kg biomass and 4.48 kg $H_2O$/kg biomass.

$$\text{Added water (kg)} = 100 \text{ kg hemp hurds} \times \frac{4.48 \text{ kg } H_2O}{1 \text{ kg hemp hurds}} = 448 \text{ kg}$$

$$\text{Added HCl (kg)} = 100 \text{ kg hemp hurds} \times \frac{0.1 \text{ kg HCl}}{1 \text{ kg hemp hurds}} = 10 \text{ kg}$$

Stream 3: After acid hydrolysis of hemp hurd in IL [$C_2C_1$im]Cl, the residual solid was separated from the hydrolysate soup (stream 4). This solid contained carbohydrates and lignin.

$$\text{Residual glucan (kg)} = 34.0 \text{ kg initial glucan} -$$
$$\left( 30.3 \text{ kg glucose yield} \times \frac{162 \text{ kg glucan}}{180 \text{ kg glucose}} \right) = 6.7 \text{ kg}$$

$$\text{Residual xylan (kg)} = 15.4 \text{ kg initial xylan} -$$
$$\left( 12.7 \text{ kg xylose yield} \times \frac{132 \text{ kg xylan}}{150 \text{ kg xylose}} \right) = 4.2 \text{ kg}$$

$$\text{Residual arabinan (kg)} = 0.6 \text{ kg initial arabinan} -$$
$$\left( 0.3 \text{ kg arabinose yield} \times \frac{132 \text{ kg arabinan}}{150 \text{ kg arabinose}} \right) = 0.3 \text{ kg}$$

Stream 4: After acid hydrolysis of hemp hurd in IL [$C_2C_1$im]Cl, the resulting hydrolysate soup contained 80.15 mol % glucose, 72.39 mol % xylose, and 50.61 mol % arabinose.

$$\text{Glucose yield (kg)} = 34 \text{ kg glucan} \times \frac{1 \text{ kmol glucan}}{162 \text{ kg glucan}} \times$$
$$\frac{1 \text{ kmol glucose}}{1 \text{ kmol glucan}} \times \frac{160 \text{ kg glucose}}{1 \text{ kmol glucose}} \times 0.8015 = 30.3 \text{ kg}$$

$$\text{Xylose yield (kg)} = 15.4 \text{ kg xylan} \times \frac{1 \text{ kmol xylan}}{132 \text{ kg xylan}} \times$$
$$\frac{1 \text{ kmol xylose}}{1 \text{ kmol xylan}} \times \frac{150 \text{ kg xylose}}{1 \text{ kmol xylose}} \times 0.7239 = 12.7 \text{ kg}$$

$$\text{Arabinan yield (kg)} = 0.6 \text{ kg arabinan} \times \frac{1 \text{ kmol arabinan}}{132 \text{ kg arabinan}} \times$$
$$\frac{1 \text{ kmol arabinose}}{1 \text{ kmol arabinan}} \times \frac{150 \text{ kg arabinose}}{1 \text{ kmol arabinose}} \times 0.5061 = 0.3 \text{ kg}$$

Stream 5: Levulinic acid, formic acid, and furfural were products of this process. We obtained 59 mol % levulinic acid, 59 mol % formic acid, and 10.5 mol % furfural.

$$\text{Levulinic acid yield (kg)} = 30.3 \text{ kg glucose} \times$$
$$\frac{1 \text{ kmol glucose}}{180 \text{ kg glucose}} \times \frac{59 \text{ kmol } LA}{1 \text{ kmol glucose}} \times \frac{160 \text{ kg } LA}{1 \text{ kmol } LA} = 11.5 \text{ kg}$$

$$\text{Formic acid yield (kg)} = 30.3 \text{ kg glucose} \times \frac{1 \text{ kmol glucose}}{180 \text{ kg glucose}} \times$$
$$\frac{59 \text{ kmol } FA}{100 \text{ kmol glucose}} \times \frac{46 \text{ kg } FA}{1 \text{ kmol } FA} = 4.6 \text{ kg}$$

-continued $$\text{Furfural yield (kg)} = 12.7 \text{ kg xylose} \times \frac{1 \text{ kmol xylose}}{150 \text{ kg xylose}} \times$$
$$\frac{10.5 \text{ kmol furfural}}{100 \text{ kmol xylose}} \times \frac{96 \text{ kg furfural}}{1 \text{ kmol furfural}} = 0.8 \text{ kg}$$

Calculation of levulinic acid titers. The levulinic acid titer is the final concentration of levulinic acid in the reaction stream. A high levulinic acid titer is desirable because it reflects the low energy consumption and purification cost. The levulinic acid titer from various processes was calculated as follows:

$$\text{Levulinic acid concentration} \left( \frac{g}{L} \right) = \frac{\text{mass of levulin acid (g)}}{\text{total volumn (L)}}$$

Example 1

Effect of Temperature/Time on Sugar Release

During Acid Hydrolysis of Hemp Hurd in IL [$C_2C_1$im]Cl

We first performed acid hydrolysis of hemp hurd in IL [$C_2C_1$im]Cl and varied the temperature and time to study the effects of reaction conditions on glucose yield in the hydrolysis soup. The IL [$C_2C_1$im]Cl was chosen because its Cl anions form hydrogen bonds with hydrogen atoms of hydroxyl groups, enhancing the cellulose dissolution (Li et al., 2018c). The resulting glucose in the hydrolysis soup underwent dehydration and rehydration to form levulinic acid. The amounts of resulting glucose, HMF, levulinic acid, and lignin were used to construct the mass balance to understand how acid hydrolysis in IL affected sugar yield, levulinic acid formation, and lignin.

To examine the effect of IL dissolution and acid hydrolysis conditions on glucose yield, we systematically varied the reaction temperature and time for IL dissolution and acid hydrolysis, while maintaining 17.5 wt % solid loading of hemp hurd.

First, the effect of IL dissolution was tested. By increasing the dissolution temperature and time, we found a maximum glucose yield at 170° C. and 1.5 h (FIGS. 2A and 2B). A further increase in the dissolution temperature or time caused the glucose yield to drop to 0%, indicating that glucose was degraded to undesired humins. An increase in the dissolution temperature and/or time promotes the interaction of the chloride anions and [$C_2C_1$im]$^+$ cations (in IL [$C_2C_1$im]Cl) with the inter-/intramolecular hydrogen-bonding networks of cellulose chains (Mostofian et al., 2014 Li et al., 2018c). These interactions disrupt the hydrogen-bonding networks of cellulose, resulting in a low degree of polymerization (DP) compounds, including cellobiose, cellobiosan, glucose, levoglucosan, and 5-hydroxymethylfurfural (HMF; Zhao et al., 2009; Gupta & Jiang, 2015; Pang et al., 2016). These sugar oligomers are more accessible to acidic protons during acid hydrolysis, resulting in the cleavage of β-1,4-glycosidic bonds and high sugar yields (Remsing et al., 2006; Cao et al., 2010; Xu et al., 2010; Chen et al., 2012). However, increasing dissolution temperature or time promoted side reactions, resulting in over-hydrolysis of glucose oligomers to undesired humin (Remsing et al., 2006; Cao et al., 2010). These behaviors were consistent with previous studies that showed decreased cellulose DP with increasing dissolution time in chloride-based ILs, such as 1-ethylpyridinium chloride ([$C_2$Py]Cl), 1-butyl-3-meth-ylpyridinium chloride, 1-butyl-3-methylimidazolium chloride ([$C_4C_1$im]Cl), and 1-ethyl-3-methylimidazolium chloride ([$C_2C_1$im]Cl). See e.g., Heinze et al., 2005; Duchemin et al., 2009; Rinaldi & Schuth, 2009; Vanoye et al., 2009; Cao et al., 2010; Chen et al., 2012; Ohno & Miyafuji, 2013; Miyata & Miyafuji, 2014; Ahn et al., 2016. These TLs dissolve cellulose and simultaneously depolymerize the dissolved cellulose to low degree of polymerization (DP) compounds (Heinze et al., 2005; Ohno & Miyafuji, 2013; Miyata & Miyafuji, 2014; Ahn et al., 2016). Ohno & Miyafuji, 2013 found that dissolving cellulose in IL [$C_2C_1$im]Cl at elevated temperatures and/or longer dissolution times caused these low-DP compounds to polymerize with IL. Miyata & Miyafuji also found that cellulose was dissolved at 120° C. and depolymerized in [$C_2$Py]Cl at a prolonged reaction time, but not in [$C_2$Py]Br and [$C_2$Py]I. They also observed the polymerization between IL and low-DP compounds. These results suggested the importance of the IL with chloride anions in dissolution and the depolymerization of dissolved cellulose.

Figures 2C, 2D:
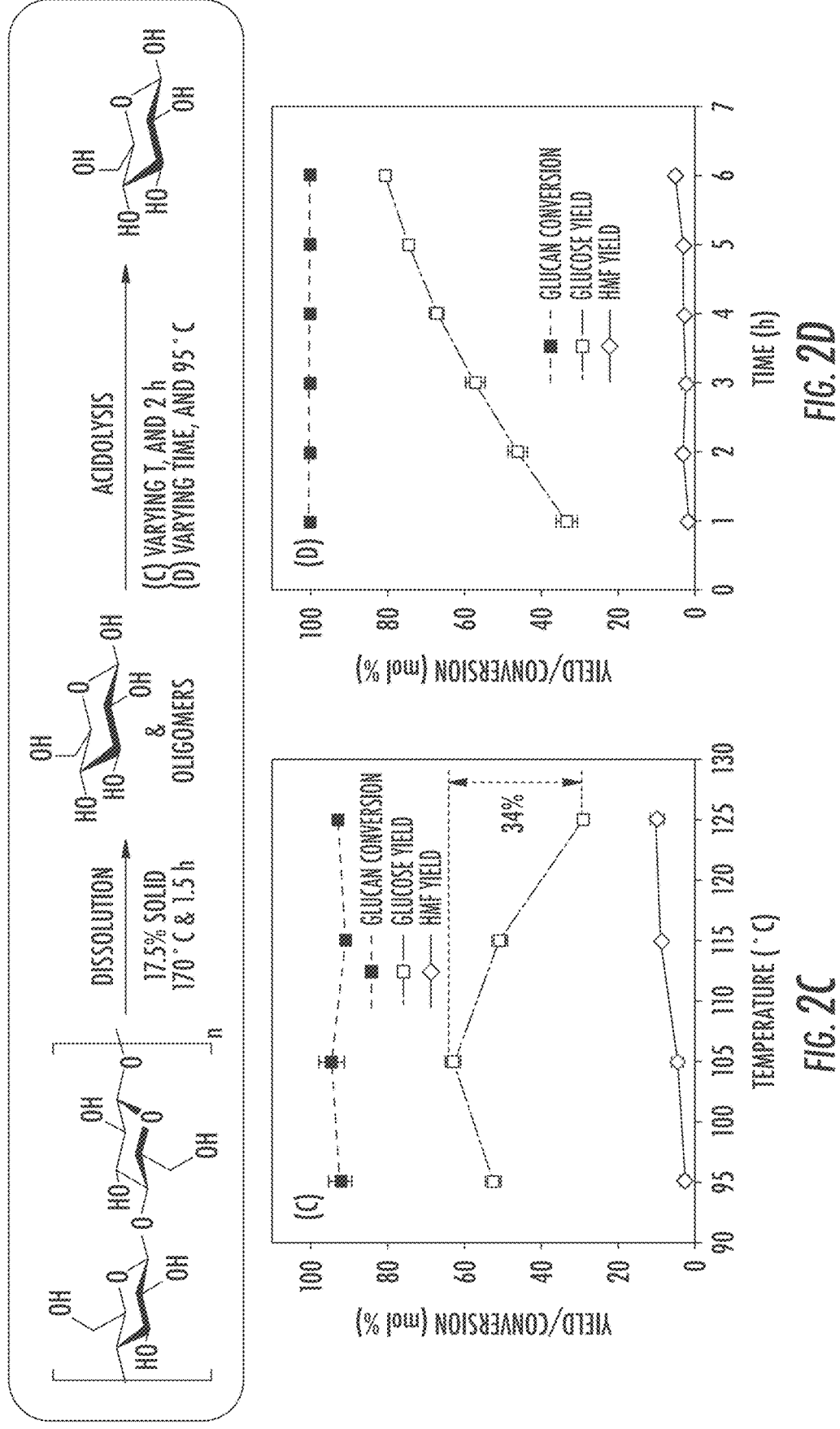

The effect of acid hydrolysis was then tested. The effects of temperature or time during acid hydrolysis were less pronounced compared with their effects during IL dissolution under our experimental condition. We observed a maximal glucose yield of 64% at the acid hydrolysis temperature of 105° C. The progressive increase in reaction temperature resulted in a 34% decrease in glucose at 125° C., but the HMF yield never exceeded 10% (FIGS. 2C and 2D). These results suggested the formation of humin at the acid hydrolysis temperature. An increase in the acid hydrolysis time increased the glucose yield to a maximum of 80% after 6 hours. The experimental condition at 95° C. resulted in a complete glucan conversion. The progressive increase in glucose yield during 6 hours of acid hydrolysis suggested that dissolved cellulose was hydrolyzed to glucose oligomers during IL dissolution. The resulting glucose oligomers were hydrolyzed to glucose during acid hydrolysis. These results suggested that (1) glucan polymers of hemp hurd were weakly hydrolyzed to glucose oligomers during dissolution in IL [$C_2C_1$im]Cl and (2) the resulting glucose oligomers were hydrolyzed to glucose during acid hydrolysis. The sugar yields were more sensitive to changes in dissolution temperature and time compared with changes in acid hydrolysis conditions. As described next, the resulting glucose in the hydrolysis soup was converted to levulinic acid.

Example 2

Levulinic Acid Formation from the Resulting Hydrolysis Soup

To produce levulinic acid, the resulting glucose in the hydrolysis soup underwent dehydration to HMF, and HMF was subsequently rehydrated to levulinic acid. Typically, both Lewis and Brønsted acid sites are needed to maximize the selectivity of levulinic acid. It is commonly accepted that Lewis acid sites are used for glucose isomerization. Brønsted acid sites are needed for glucose dehydration to HMF and HMF rehydration to levulinic acid (Choudhary et al., 2013; Weingarten et al., 2013; Weiqi & Shubin, 2017). Previous studies have shown that the combination of Lewis acid and Brønsted acid catalysts enables the glucose conversion to levulinic acid in one pot. Because our hydrolysis soup contained dilute HCl (0.25 mol/L, 0.9 wt %), we speculated that adding Lewis acids in the hydrolysis soup would enable efficient levulinic acid formation in one pot by promoting glucose isomerization to fructose. The resulting fructose would undergo dehydration to HMF and rehydration to levulinic acid.

Figure 3:
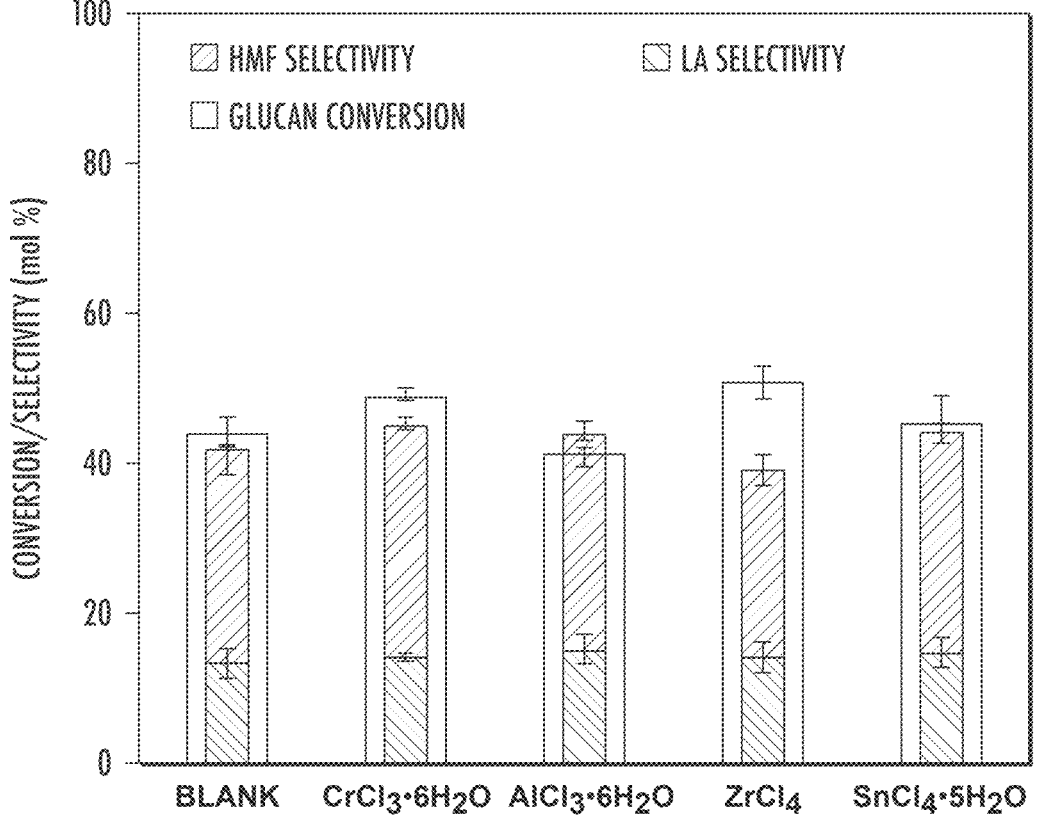
FIG. 3 is a bar graph showing the effect of Lewis and/or Brønsted acid on levulinic acid selectivity of the hydrolysis soup. Reaction condition: 10% catalyst loading at 120° C. for 2 hours. The lighter gray areas correspond to glucan conversion, the diagonally hatched bars correspond to HMF selectivity, and the darker gray areas correspond to LA selectivity.

To investigate a possible synergistic effect of Brønsted and Lewis acids for levulinic acid formation, we added selected Lewis acid catalysts, $CrCl_3$, $AlCl_3$, $ZrCl_4$, and $SnCl_4$, to our hydrolysis soup. The added Lewis acid catalysts were chosen based on their high performance in glucose dehydration (Kobayashi & Manabe, 2002; Wang et al., 2012; Enslow & Bell, 2015; Swift et al., 2015; Weiqi & Shubin, 2017). The dilute HCl in the hydrolysis soup acted as a Brønsted acid catalyst. Heating our hydrolysis soup at 120° C. for 2 hours resulted in 28% HMF and 13% levulinic acid selectivities at 44% glucan conversion (FIG. 3). We did not observe fructose as a product. Moreover, added Lewis acid catalysts had little to no effect on glucan conversion and selectivities toward HMF and levulinic acid. These results suggested that the HCl catalyzed both glucose dehydration and HMF rehydration and that Lewis acid catalysts were not necessary for levulinic acid formation. Consistent with our observation, other investigators have found that the presence of inorganic acid alone (i.e., $H_2SO_4$) at elevated temperatures (170-220° C.) in aqueous media was sufficient to catalyze both glucose dehydration and HMF rehydration (Hanna, 2002; Chang et al., 2007; Fang & Girisuta et al., 2008; Runge & Zhang, 2012; Muranaka et al., 2014). The inactivity of Lewis acid catalysts to catalyze glucose isomerization in our hydrolysis soup may have been due to water and inhibitors in the hydrolysate. Previous studies achieved a high levulinic acid yield of 46% at 140° C. after 6 hours (Choudhary et al., 2013). However, one must strike a balance between Brønsted-to-Lewis acid sites to provide the synergistic effects between glucose isomerization, fructose dehydration, and HMF rehydration because excess Lewis acid catalysts can also promote undesired side reactions (e.g., humin formation). See Weingarten et al., 2013; Weiqi & Shubin, 2017.

The humin formation is common in processing lignocellulose under acidic conditions. Humins occur from various reaction pathways, including condensation of furan and lignin-derived compounds (van Zandvoort et al., 2013; Yoon et al., 2014), polymerization of furans from sugar dehydration (HMF and furfural; Tuercke et al., 2009), acid-catalyzed conversion of glucose, fructose, and furans (Patil et al., 2012). van Zandvoort et al., 2013 studied sugar conversion to furans and levulinic acid in dilute $H_2SO_4$ (0.01-0.1 mol/L) at 140-220° C. The structure of humins varied, depending on the type of sugars. Consistent with our findings, they revealed that the yields of levulinic acid and humin were strongly dependent on the acid concentration, reaction conditions, and type of feedstock (van Zandvoort et al., 2013). Hence, the acid concentration and reaction conditions in our process should be optimized to minimize the humin formation, thereby increasing the levulinic acid yield.

Figure 4:
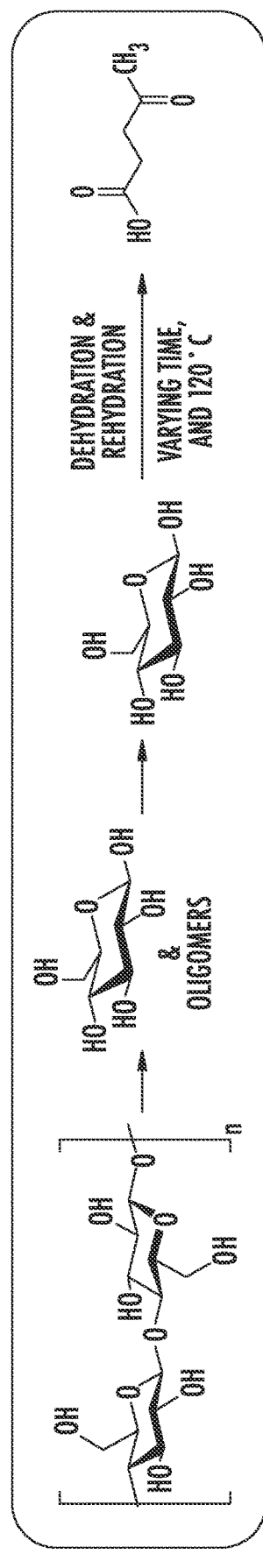
FIG. 4 shows the evolution of levulinic acid as a function of reaction time at 120° C. The hydrolysis soup was obtained from acid hydrolysis of hemp hurd in IL [C$_2$C$_1$im]Cl using the IL dissolution at 170° C. and 1.5 hours and the acid hydrolysis at 95° C. for 6 hours. In the bottom panel, squares: glucan conversion; triangles, LA yield; circles: HMF yield.
Figure 4:
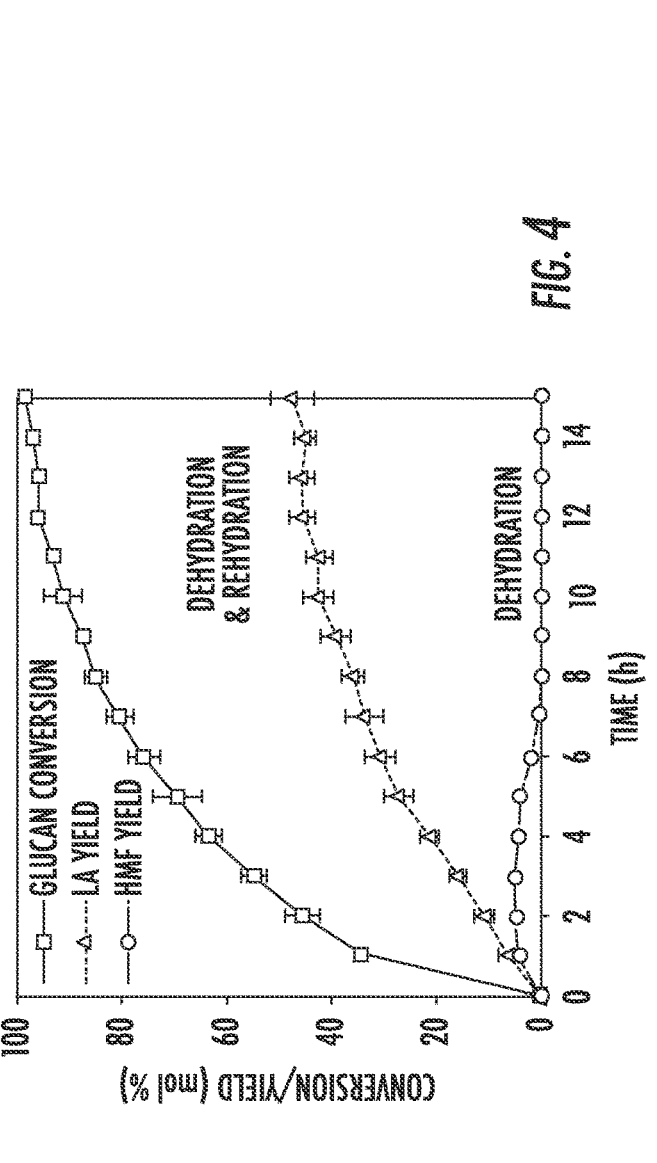

Further tests of heating the hydrolysis soup over time showed increasing glucan conversion and levulinic acid yield. We reached a complete glucan conversion and the maximum levulinic acid yield of 47% (59% levulinic acid yield based on the resulting glucose after acid hydrolysis of hemp hurd in TL [$C_2C_1$im]Cl) at 120° C. after 12 hours (FIG. 4). The change in HMF yield was low (<10%). To the best of our knowledge, we are the first to achieve a high 47% yield of levulinic acid from hemp hurd with a mild reaction condition (120° C. after 12 h). Moreover, we have elucidated the advantage of IL dissolution in the formation of levulinic acid in a mild condition.

Example 3

Mass Balance of the One-Pot, Two-Step Process to Produce Levulinic Acid from Hemp Hurd in IL [C$_2$C$_1$Im]Cl Wide interest in using industrial hemp for various applications has led to the realization of using hemp hurd as a co-product. As a result, several processes have been developed to release sugars from hemp hurd because resulting sugars are building blocks for the production of biofuels and bioproducts. To assess the economic feasibility of levulinic acid formation from acid hydrolysis of hemp hurd in IL [C$_2$C$_1$im]Cl, we constructed and calculated its mass balance based on the optimal process condition. Acid hydrolysis in IL [C$_2$C$_1$im]Cl produced ~43.4 kg reducing sugars (78% reducing sugar yield), corresponding to 30.3 kg glucose (81% glucose yield), 12.7 kg xylose (72% xylose yield), and 0.3 kg arabinose (43% arabinose yield) on the basis of 100 kg hemp hurd (stream 4, FIG. 5). Moreover, the residual solid after acid hydrolysis was lignin-rich (66 wt % lignin; stream 3, FIG. 5). The resulting hydrolysis soup underwent dehydration/rehydration and formed 11.5 kg levulinic acid (stream 5, FIG. 5), corresponding to 47% levulinic acid yield. Hence, we compared our results with levulinic acid formation processes that used other feedstock types.

The Biofine process, the commercial process for levulinic acid production, uses two-staged dilute sulfuric acid (1.5-3.0 wt %). 66 This process gives a high levulinic acid yield (69%) in short reaction time. However, the Biofine process requires costly high reaction temperature and pressure (stage 1: 210-220° C., 25 bar and stage 2: 190-200° C., 14 bar), and it uses a low loading of lignocellulose (~1.5-2.0 wt %), which yields a low titer of product (Weingarten et al., 2012; Licursi et al., 2018). Similarly, other investigators have reported hydrothermal conversion processes using dilute HCl and H$_2$SO$_4$ and produced relatively high yields of levulinic acid (~46-69%) from lignocellulose. Although these processes gave attractive yields, they used high temperatures (175-220° C.), high acid concentrations (3.5-10 wt %), and low lignocellulose loading (6-10 wt %), contributing to the capital expenditure (CAPEX) and operational expenditure (OPEX) of the process. Consistent with our results (FIG. 3), these studies confirmed that the addition of Lewis acid catalysts did not improve the yield of levulinic acid.

Figure 5:
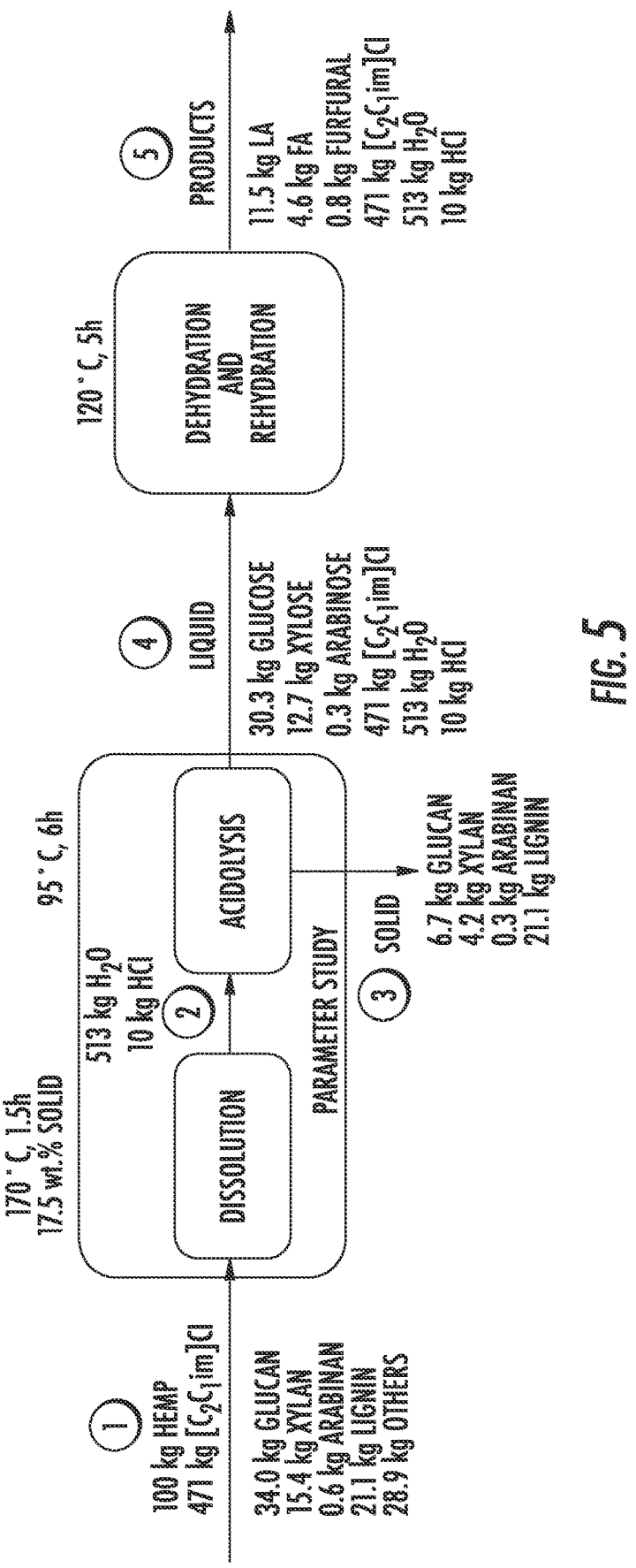
FIG. 5 depicts mass balance of levulinic acid formation from hemp hurd in IL [C$_2$C$_1$im]Cl, which showed 47% levulinic acid yield. Basis: 100 kg hemp hurd.

Our one-pot, two-step levulinic acid formation system that used acid hydrolysis of hemp hurd in IL [C$_2$C$_1$im]Cl gave 59% levulinic acid yield (based on the resulting glucan content after acid hydrolysis of hemp hurd in IL [C$_2$C$_1$im] Cl). This yield should be improved to make it competitive with other processes (Hayes et al., 2006; U.S. Pat. No. 5,608,105; each of which is incorporated herein by reference in its entirety). However, our process has three key advantages that already make it competitive. First, the IL dissolution step enabled the use of a low acid concentration (0.9 wt % HCl) and a mild reaction condition (step 1: 120-170° C., 1.5 hours, atmospheric pressure and step 2: 120° C., 15 hours; FIG. 5), which makes our process less energy-intensive compared with other processes. Second, we used a high lignocellulose loading of 17.5 wt %. As indicated earlier, most levulinic acid production processes use a low solid loading (<10 wt %) to facilitate the rate of the reaction and increase the yield of desired products. However, low biomass loading leads to a low titer and high production cost of desired products (e.g., levulinic acid; Jin et al., 2017). High biomass loading (>15 wt %) is desired to ensure the economic viability of the biorefinery, but it causes high viscosity during processing, requiring additional power for mixing (Lu et al., 2010). Moreover, at a high biomass loading, severe processing conditions (high temperature, pressure, and longtime) are required, leading to undesired side reactions, high processing cost, and low product yields (Lu et al., 2010). Third, we performed acid hydrolysis in IL and dehydration/rehydration in one pot, eliminating extra unit operations to separate glucose and HMF intermediates. The ability of our process to operate at high biomass loading of 17.5 wt % and with a mild reaction condition, while maintaining the high yield of levulinic acid, shows a great potential to reduce capital and operational expenditures.

The levulinic acid titer is an important scaling indicator and economic factor of the process because the high titer makes downstream product purification less complex (Zhu et al., 2011). The levulinic acid titer ranged from 3.6 to 24.1 g/L. Although the acid-catalyzed conversion of poplar, cedar, and starch result in the high levulinic acid titer of 17.5-24.1 g/L, the tradeoff is that they use harsh reaction conditions as shown at a high temperature (190-220° C.; Fang & Hanna, 2002; Runge & Zhang, 2012; Muranaka et al., 2014). The Biofine process gave a low levulinic acid titer of 3.6 g/L because of a low solid loading in the process (U.S. Pat. No. 5,608,105). Our one-pot, two-step levulinic acid formation system gave a relatively high titer of ~12.1 g/L. Although our process performed at a high solid loading of 17.5 wt %, hemp hurd had ~34% glucan content, resulting in a slightly lower levulinic acid titer compared with other processes.

Our process produced levulinic acid and formic acid in IL [C$_2$C$_1$im]Cl. The separation of levulinic and formic acids from the product stream and the recycle of ionic liquids should be considered to make this process economical. Several technologies show potential in separating levulinic acid and formic acid from the product stream, such as liquid-liquid extraction (Nhien et al., 2016; Brouwer et al., 2017), solid-liquid extraction (Zheng et al., 2018), gas stripping, and distillation (U.S. Patent Application Publication No. 2015/0052806, which is incorporated herein by reference in its entirety). For example, Nhien et al., 2016 used methyl isobutyl ketone (MIBK) to selectively extract levulinic acid from other products in the process. Several techniques, such as distillation (Ha et al., 2010; Taylor et al. 2010), extraction (Blanchard & Brennecke, 2001; Sun et al., 2013), and membrane-based methods (Schafer et al., 2001; Abels et al., 2012), show potential in recycling ionic liquids. Sathitsuksanoh et al. used octanol to purify and reused the IL [C$_2$C$_1$im]OAc for biomass processing (Sathitsuksanoh et al., 2015). Both IL [C$_2$C$_1$im]-OAc and octanol were reused three times without a drop in biomass processing efficiency. The development of the largescale recycling process, techno-economic analysis (TEA) model, and life cycle analysis (LCA) of this process are underway. In sum, our one-pot, two-step levulinic acid formation system operates under a mild reaction condition and eliminates the separation of intermediate products, reducing the operating cost for biorefineries. These reasons make this system an attractive approach for practical applications.

Discussion of Examples 1-3

Levulinic acid is a versatile chemical, derived from renewable cellulosic biomass by a cascade of reactions. Poor solubility of cellulose caused by abundant hydrogen bonding networks presents a major challenge in cellulosic biomass conversion. The interaction between dilute HCl and cellulosic hemp hurds solubilized in 1-ethyl-3-methylimidazolium chloride ([C$_2$C$_1$im]Cl) for hydrolysis of cellulose to glucose and conversion of glucose to levulinic acid in one pot was assessed. The dissolution of cellulosic biomass in [C$_2$C$_1$im]Cl enhanced cellulose accessibility to acid, enabling efficient glucose release under mild dissolution (<170° C.) and acid hydrolysis conditions (<105° C.). The resulting glucose readily underwent dehydration and subsequent hydrolysis to levulinic acid without additional catalysts. 59% levulinic acid yield was achieved in this one-pot system at 120° C. Moreover, because the residual lignin was not condensed, it is a potentially useful co-product. The approach disclosed herein was simple, and it eliminated the need to separate intermediate products (glucose and 5-hydroxymethyl furfural).

We have demonstrated a one-pot, two-step acid-catalyzed conversion of hemp hurd to levulinic acid using dilute HCl in ionic liquid (IL) [C$_2$C$_1$im]Cl. Beginning with hemp hurd, we achieved 47% levulinic acid yield under mild conditions: 170° C. and 1.5 hours for hemp hurd dissolution in IL, 95° C. and 6 hours for hydrolysis of dissolved cellulose to glucose, and 120° C. and atmospheric pressure for glucose dehydration/rehydration to levulinic acid. This study revealed that glucose release was more sensitive toward changes in dissolution temperature and time than changes in the acid hydrolysis condition. The resulting glucose in the hydrolysis soup underwent dehydration and rehydration in the presence of HCl, forming levulinic acid without additional catalysts. The addition of Lewis acid catalysts (CrCl$_3$, AlCl$_3$, ZrCl$_4$, and SnCl$_4$) was not necessary. This one-pot approach accommodates high lignocellulose loading, eliminates the separation of intermediate products (glucose and HMF), and uses only a single catalyst. The use of upstream lignocellulose dissolution in ionic liquids makes this one-pot strategy applicable to other lignocellulosic biomasses.

Materials and Methods for Examples 4-9

Chemicals and Materials. All chemicals were reagent grade and purchased from Sigma-Aldrich (St. Louis, Missouri, USA) unless otherwise noted. Phosphoric acid (85% w/w) and ethanol (95% v/v) were purchased from Fisher Scientific (Houston, Texas, USA). Microcrystalline cellulose, Avicel PH105 (20 lm), was obtained from FMC Corp (Philadelphia, Pennsylvania, USA). Regenerated amorphous cellulose (RAC) was prepared as described (Sathitsuksanoh et al., 2011; Sathitsuksanoh et al., 2012b). In short, (1) Avicel was mixed with water to make a slurry; (2) ice-cold 85% H$_3$PO$_4$ (~4° C.) was added to the Avicel slurry and kept on ice for 1 hour; and (3) deionized water was added to regenerate the RAC (Rollin et al., 2011). *Trichoderma reesei* cellulase (Novozyme 50013) and β-glucosidase (Novozyme 50010) were gifted by Novozymes North America (Franklinton, North Carolina, USA). They had activities of 84 filter paper units (FPUs) of cellulase per mL and 270 units of β-glucosidase per mL. Southern yellow pine woodchips and Douglas fir were obtained from Brook Center at Virginia Tech (Blacksburg, Virginia, USA) and University of British Columbia (Vancouver, Canada), respectively. All naturally dried biomass samples were knife-milled by a Pallmann counter-rotating knife ring flaker (Clifton, New Jersey, USA). The resulting particulates with nominal sizes of 40-60 mesh (250-400 m) were collected. They are referred to as untreated Douglas fir and pine and used as controls.

H$_3$PO$_4$ Pretreatment of Softwoods. Pine and Douglas fir were pretreated with 85% H$_3$PO$_4$ as described (Sathitsuksanoh et al., 2009; Rollin et al., 2011). In short, approximately 1.05 g of natural-dried biomass (~5% moisture) was mixed with 8 mL of 85% (w/w) H$_3$PO$_4$ in a 50 mL plastic centrifuge tube and heated at 50° C. at atmospheric pressure for 105 min, unless otherwise noted. The pretreatment reaction was stopped and regenerated by adding 20 mL of 95% (v/v) ethanol. Pretreated solid was separated by a swing bucket centrifuge at 4500 rpm for 10 minutes. The supernatant was removed. The pretreated solid was washed and centrifuged in a sequence of 40 mL of 95% (v/v) ethanol and 40 mL of deionized water two times, respectively. The resulting solid was neutralized with a 2M sodium carbonate solution and stored in the presence of 0.1% (w/v) NaN$_3$ at 4° C. to prevent microbial growth prior to enzymatic hydrolysis. These resulting pretreated solids after H$_3$PO$_4$ pretreatment, regeneration, and solvent wash are referred to as pretreated pine and Douglas fir throughout this study. The severity of the H$_3$PO$_4$ pretreatment of softwoods was expressed as the severity factor (R$_0$; Overend et al., 1987). The R$_0$ combined reaction temperature and time and in the following calculation:

$$\log R_0 = \left[ t \cdot \exp\left( \frac{T - 100}{14.75} \right) \right]$$

where R$_0$ is the combined reaction temperature and time, and t and T are the pretreatment time in minutes and the temperature in ° C., respectively. This calculation did not account for an effect of pH because pH information was lacking during pretreatment processes. The R$_0$ values of other pretreatment processes were also calculated for comparison.

Enzymatic Hydrolysis. The pretreated softwood was suspended to obtain 10 g of glucan per liter in a 50 mM sodium citrate buffer (pH ~4.8) supplemented with 0.1% (w/v) NaN$_3$ (to prevent microbial growth) in a 50 mL centrifuge tube. Enzyme loadings were the following: (1) 5 FPUs of cellulase and 10 units of β-glucosidase per gram of glucan or (2) 15 FPUs of cellulase and 30 units of β-glucosidase per gram of glucan, unless otherwise noted. The cocktail (pretreated samples+buffer solution+enzyme) was suspended in an incubator shaker at 50° C. and 600 rpm; samples were collected for 72 hours. The cocktail samples were centrifuged at 13 000 rpm for 5 minutes to separate clear solution from the suspended solids. Exactly 500 μL of the supernatant was transferred to a 2 mL microcentrifuge tube maintained at room temperature for 30 minutes to allow cellobiose to be continuously converted to glucose by the residual enzyme. This step was important to ensure accurate enzymatic hydrolysis results. The supernatant was then acidified by adding 30 μL of 10% (w/w) sulfuric acid, followed by freezing overnight. The frozen sample was thawed, mixed well, and centrifuged at 13,000 rpm for 5 minutes to remove any precipitated solids. The supernatant, containing soluble sugars after enzymatic hydrolysis, was processed with an 1110 Agilent high-pressure liquid chromatography system (HPLC, Agilent Technologies, Santa Clara, California, USA). Enzymatic glucan digestibility was calculated as follows:

glucan digestibility (%)=(glucan$_{supernant}$/glucan$_{pretreated\ biomass}$)×100

After 72 hours enzymatic hydrolysis, the residual solid was washed with 20 mL of deionized water to remove soluble sugars and enzyme prior to freeze-drying overnight. All experiments were conducted in triplicate, and the standard deviations were calculated. The composition of the residual solid was then analyzed to construct the mass balance. Environmental factor (E-factor; Sheldon, 2007) was calculated to describe the sustainability aspect of the pretreatment, followed by enzymatic hydrolysis of softwoods. The inputs and outputs from the mass balance were used in the E-factor calculation. The E-factor is the ratio between the amount of waste produced (residual biomass, chemicals, and solvents/water) and the amount of desired products (glucose or glucose equivalent, in this case) produced:

$$E\text{-}factor = \frac{amount\ of\ waste}{amount\ of\ desired\ product}$$

The E-factors of the pretreatment alone and pretreatment+ enzymatic hydrolysis of the selected processes were calculated for comparison.

Compositional Analysis of Softwoods and Glucose Determination. Compositional analysis of softwoods and residual enzymatic hydrolysis solids was performed by the NREL LAP procedure (Sluiter et al., 2008; Sluiter et al., 2011). Briefly, 0.2 g of the sample was dissolved in 2 mL of 72% $H_2SO_4$ at 30° C. for 1 hour in an incubator shaker prior to dilution of the $H_2SO_4$ concentration to 4% with deionized water. The sample was autoclaved at 121° C., 15 psi for 1 hour and then filtered by a ceramic filter crucible. The filtrate was analyzed by HPLC for soluble sugars. Residual solids were dried at 105° C. overnight. The weight of the dried solids corresponded to the amount of lignin and ash in the sample. The weight loss of the dried sample and residual weight after calcination at 575° C. for 8 hours corresponded to the amount of lignin and ash, respectively, in the sample.

Soluble sugars were measured by HPLC equipped with a refractive index detector (RID) and diode array detector (DAD). A Bio-Rad Aminex HPX-87P column (Richmond, California, USA) was used to analyze soluble sugars with a rate of 0.6 mL/min of 4 mM $H_2SO_4$ as a mobile phase at 60° C. All sugars were calibrated against certified standards (Absolute Standards Inc., Hamden, Connecticut, USA).

Characterization of Softwoods before and after $H_3PO_4$ Pretreatment. The total substrate accessibility to cellulase (TSAC), cellulose accessibility to cellulase (CAC), and non-cellulose accessibility to cellulase (NCAC) were determined based on the maximum adsorption of the TGC fusion protein. This fusion protein contained thioredoxin (T), green fluorescent protein (GFP), and three cellulose-binding modules (C). The fusion protein was used in the presence and absence of bovine serum albumin (BSA; Zhu et al., 2009; Rollin et al., 2011). TSAC was calculated by the maximum adsorption of TGC in the absence of BSA, whereas CAC was calculated by the maximum adsorption of TGC in the presence of BSA. NCAC was calculated by the difference between TSAC and CAC. TGC fusion protein was produced in *Escherichia coli* BL21 (pNT02), purified by adsorption onto regenerated amorphous cellulose (RAC), and desorbed with ethylene glycol (EG; Hong et al., 2008). EG was removed by dialysis in a 50 mM sodium citrate buffer (pH 6.0) and the TGC solution was concentrated using Millipore 10 kDa molecular weight cutoff centrifugal ultrafilter columns (Spectrum Lab, Billerica, Massachusetts, USA). Confocal microscopy was performed to confirm the presence of TGC on biomass. The confocal images were recorded on the Zeiss Axio Observer Z1 inverted microscope for fluorescence or brightfield microscopy (Carl Zeiss Microscopy, LLC, Thornwood, New York, USA).

Scanning Electron Microscopy (SEM). SEM images of the biomass materials were taken with a Zeiss-DSM940 (Carl Zeiss, Okerkochen, Germany), as described in Moxley et al., 2008. All samples were sputter-coated with gold prior to SEM imaging.

Attenuated Total Reflection (ATR) Fourier-Transform Infrared (FTIR) Spectroscopy. ATR-FTIR was conducted using a Thermo Nicolet 6700 ATR/FT-IR spectrometer (Thermo Fisher Scientific Inc., Waltham, Massachusetts, USA). A total of 256 scans at a resolution of 6 cm$^{-1}$ were averaged for each sample. The samples were scanned in the spectral range between 400 and 4000 cm$^{-1}$. The absorbances of the bands were resolved using Voigt distribution function by PeakFit1 4.12 software (Systat Software Inc., Chicago, Illinois, USA).

Cross-Polarization/Magic Angle Spin (CP/MAS) $^{13}$C-Nuclear Magnetic Resonance (NMR). The CP/MAS $^{13}$C-NMR spectra of all samples were acquired with a Bruker Avance I 500-MHz NMR spectrometer operating at the resonance frequencies of 500.23 MHz for 1H and 125.80 MHz for 13C, using a double-resonance Bruker 4.0 mm broad-band CP-MAS probe spinning at 13-14 kHz. Cross-polarization for 2 ms contact time was achieved using a $^1$H 90° pulse width of 4.2 s at 60-kHz two-pulse phase-modulated proton decoupling field and 2-s recycle delay. Total accumulation time was between 1000 and 3000 transients. All spectra were collected at room temperature and referenced against the chemical shifts of adamantane at 38.48 and 29.45 ppm. According to the $C_4$ peak-deconvolution method, the degree of crystallinity was determined and expressed as the crystallinity index (CrI) (see Park et al., 2010).

2D $^{13}$C-$^1$H heteronuclear single quantum coherence (HSQC) NMR spectroscopy. Softwood samples were extracted to remove extractives and ball-milled as described in Kim & Ralph, 2010 and Mansfield et al., 2012. The ball-milled softwood sample (~20-30 mg) was mixed with DMSO-d$_6$ (600 µL) in a microcentrifuge tube. A minute amount of 1-ethyl-3-methylimidazolium acetate (~10 µL) was added as a cosolvent to help dissolve softwood samples (Cheng et al., 2013; Sathitsuksanoh et al., 2014). This solution was sonicated in a Branson 2510 table-top cleaner (Branson Ultrasonic Corporation, Danbury, Connecticut, USA) until it became a homogeneous gel. The temperature of the sonication bath was maintained below 55° C. The homogeneous gel was transferred to the NMR tube. HSQC spectra were acquired at 25° C. using a Bruker Avance-600 MHz instrument equipped with a 5 mm inverse-gradient $^1$H/$^{13}$C cryoprobe and the q_hsqcetgp pulse program (ns=200, ds=16, number of increments=256, d1=1.0 s; Heikkinen et al., 2003). Chemical shifts were referenced to the central DMSO peak ($\delta_C/\delta_H$ 39.5/2.5 ppm). Assignments of the HSQC spectra were as described in Kim & Ralph, 2010. A semiquantitative analysis of the volume integrals of the HSQC correlation peaks was performed using Bruker's Topspin 3.1 (Windows) processing software. A Gaussian apodization in $F_2$ (LB=−0.50, GB=0.001) and squared cosine-bell in $F_1$ (LB=−0.10, GB=0.001) were applied prior to 2D Fourier Transformation. The semiquantitative evaluation of the interunit linkages of lignin was expressed as (1) the relative abundance of the interunit linkages of lignin and (2) the amount of interunit linkages per 100 aromatic (Ar) units (C9 units) in lignin. The calculations were performed as follows:

the relative abundance (%) =

$$\frac{\text{volume Integral of interunit linkage}}{\text{total volume integral of all interunit linkage}} \times 100$$

amount of interunit linages (per 100 $Ar$ units) =

$$\frac{\text{volume Integral of interunit linkage}}{\text{volume Integral of correlation peak of } G_2}$$

Example 4

Effect of $H_3PO_4$ Pretreatment of Softwood on Enzymatic Hydrolysis

The pine and Douglas fir samples consisted of ~35-39 wt % glucan, 9-12 wt % mannan, 3-6 wt % xylan, and 33-34 wt % lignin. The high mannan content was a signature of softwoods. The softwood compositions determined agreed with previously reported values (Normark et al., 2014; Biswas et al., 2015). High lignin content in softwoods and its highly cross-linked G-type lignin structure are barriers for enzymes and/or catalysts to access cellulose. An exemplary strategy to circumvent this barrier was to employ $H_3PO_4$ pretreatment to disrupt the lignin-carbohydrate complex (LCC) linkages and intra/intermolecular hydrogen bonds between crystalline cellulose chains of softwoods.

Untreated pine and fir showed a low glucan digestibility of <7% after 72 hours with 15 FPUs/g glucan of enzyme loading. These results illustrated the high recalcitrance of softwoods. Conversely, pretreated pine and Douglas fir had a fast hydrolysis rate and their glucan digestibilities were >72% after 12 hours, reaching a maximum of 87% after 72 hours for Douglas fir at 15 FPU/g glucan enzyme loading. A 3-fold reduction in enzyme loading (5 FPU/g glucan) still yielded a fast hydrolysis rate and high glucan digestibilities of >63% after 12 hours and >80% after 72 hours for both softwoods (FIGS. 7A-7D). These results confirmed that $H_3PO_4$ pretreatment was efficient for softwoods; thus, a high glucan digestibility (>63%) was obtained after 12 hours at a low cellulase loading.

Pretreatment cost represents about 20% of the total cost of biomass conversion processes (Yang & Wyman, 2008). The harsh reaction conditions (high temperature: 170-200° C. and 6.5-7.2 bar) and/or high enzyme loading add significantly to capital expenditure (CAPEX) and operating expenditure (OPEX) of the overall process. Moreover, a harsh reaction condition (high temperature >120° C.) possibly cleaves β-O-4 lignin linkage and forms undesired condensed C—C linkages (Funaoka et al., 1990), limiting lignin's potential upgrading to coproducts.

To obtain a high glucan digestibility, typically, severe pretreatment conditions (high log $R_0$) are required to disrupt the highly ordered crystalline cellulose of softwoods. Previous high log $R_0$ (3.54-5.00) studies with organosolv, sulfite, and physicochemical pretreatments did demonstrate high sugar yields (Fujii et al., 2009; Sannigrahi et al., 2010; Shuai, 2010; Rana et al., 2012). The high log $R_0$ suggested that the pretreatments were energy-intensive, contributing to the high CAPEX and OPEX of the overall processes. For example, Shuai et al. studied sulfite pretreatment to overcome recalcitrance of lignocellulose (SPORL) and by dilute acid (DA) pretreatment of spruce at 180° C. for 30 minutes (log $R_0$ of 3.83) and obtained 91% and 55% glucan digestibility, respectively, with 15 FPUs/g glucan enzyme loading (Shuai, 2010). A decrease in enzyme loading from 10 to 5

FPUs/g glucan dropped the glucan digestibility of SPORL-pretreated spruce from 91% to 70% (Shuai, 2010). Nonetheless, this and similar approaches do not mitigate the high economic cost of conversion.

The green chemistry environmental factor (E-factor) is another important indicator of the sustainability of a process (Sheldon, 2007; Sheldon & Sanders, 2015). A high E-factor indicates that a process produces more waste with a negative environmental impact (Sheldon, 2017). The ideal E-factor is zero, but zero is not usually attainable because most chemical processes generate some waste. For softwood pretreatment processes, E-factors have ranged from 10.7 to 174.0. Ball milling and wet explosion pretreatments have low E-factors (10.7-12.3) because they use low amounts of chemicals. Although the ball-milling samples gave a low E-factor of 12.3, they achieve only a moderate glucan digestibility of 63% after 72 hours with a high enzyme loading of 114 FPU/g glucan (173 mg protein/g glucan).

The foregoing examples emphasize that a balance must be struck between minimizing sugar degradation and/or inhibitory compound formation (low log $R_0$) and minimizing waste (low E-factor). However, low $R_0$ and low E-factor do not necessarily go hand-in-hand. From a cost and sustainability standpoint, a mild and environmentally friendly pretreatment process would revolutionize the future biorefinery.

The $H_3PO_4$ pretreatment process disclosed herein had an E-factor of 168.9. However, several advantages of our approach offset this high E-factor. First, a high glucan digestibility of ~78-80% was achieved with a low enzyme loading (5 FPUs/g glucan) and a high reaction rate. The enzyme cost in biofuels production is ~$0.68/gal (based on theoretical sugar yields from lignocellulosic biomass) or $1.47/gal (based on saccharification and fermentation yields) of bioethanol (Klein-Marcuschamer et al., 2010; Klein-Marcuschamer et al., 2011). Hence, the reduction of enzyme loading while maximizing sugar yield is an important economic feature of the process disclosed herein. Second, the $H_3PO_4$ pretreatment was conducted at a mild reaction condition of 50° C. and atmospheric pressure, with an associated low severity factor of 0.91. More commonly, high severity pretreatments are used to achieve high glucan digestibility of softwoods, but high severity pretreatments cause sugar degradation and formation of inhibitors (furfural, 5-hydroxymethylfurfural (HMF), acetic acid, levulinic acid, and formic acid) to downstream fermentation step (Robinson, 1996; Bozell et al., 2000; Chakar & Ragauskas, 2004; Li et al., 2007; Binder & Raines, 2010; Stihlberg et al., 2010; Samuel et al., 2011; Chio et al., 2019; Zhang et al., 2019). Third, $H_3PO_4$ recycling can be considered as a means to further enhance the economic benefit of our process. Liquid extraction (Amin et al., 2010; Assuncao et al., 2017) and diffusion dialysis (Kim et al., 2012) show potential in recycling $H_3PO_4$ with high purity (80-90% acid recovery). Moreover, spent $H_3PO_4$ can be used to produce fertilizer (Liu & Chen, 2008). In sum, the $H_3PO_4$ pretreatment process can reduce energy consumption, enzyme loading, and likely the operating costs for biorefineries.

Example 5

Figure 8:
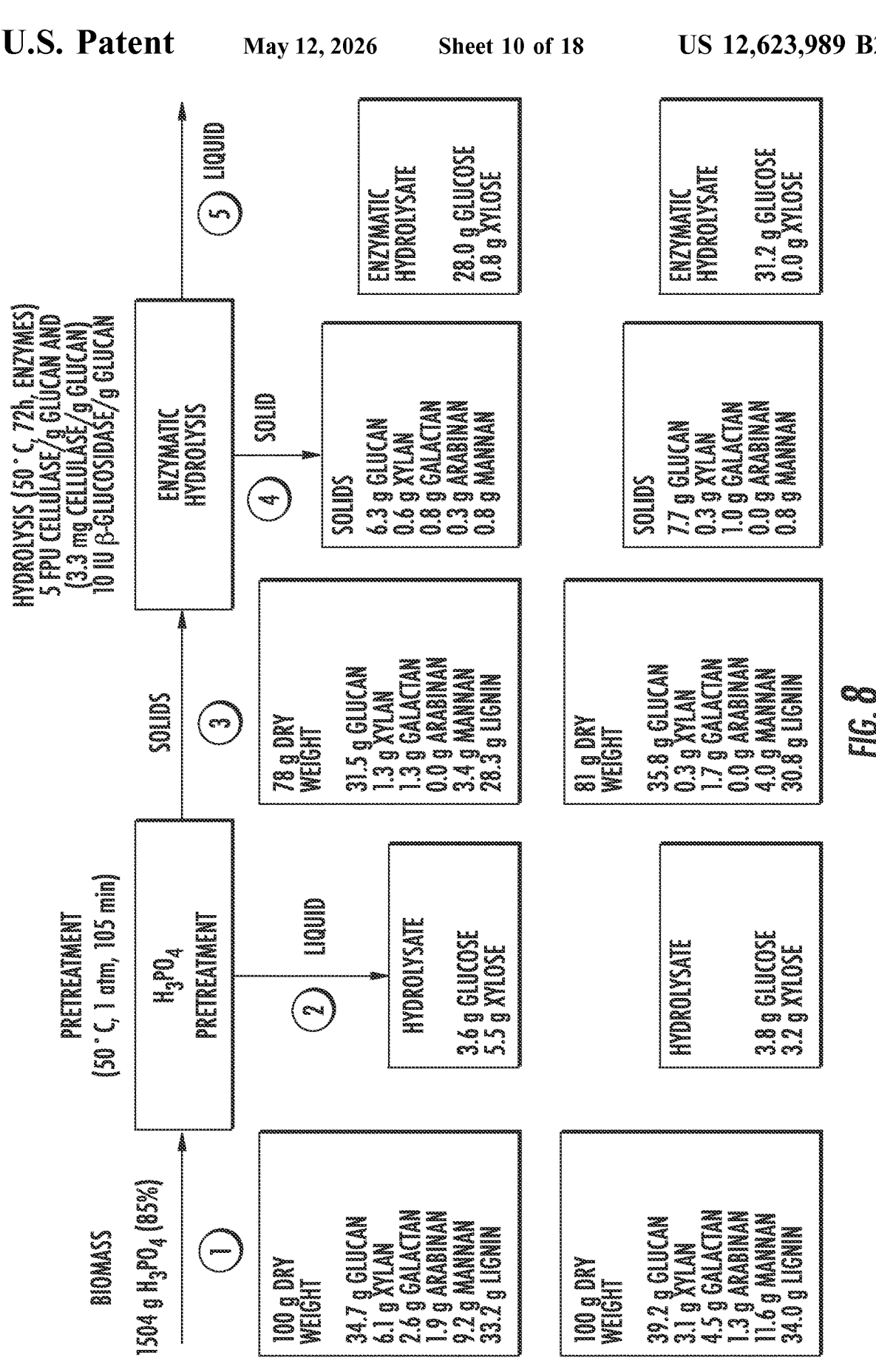
FIG. 8 is a mass balance of H$_3$PO$_4$-pretreated yellow pine (top) and H$_3$PO$_4$-pretreated Douglas fir (bottom) at 5 FPU/g glucan.

Mass Balance of the Pretreatment and Enzymatic Hydrolysis of Pine and Douglas Fir To understand the economics of the process, the mass balance was constructed on the basis of 100 g of softwood (FIG. 8). The solid recovery was 78% and 81% for pretreated pine and Douglas fir. A high glucan recovery, ~90%, was obtained from pretreated pine and Douglas fir, whereas xylan recovery was low (~10%; FIG. 8, stream 3). These results suggested that ethanol could efficiently recover most dissolved glucan and simultaneously fractionate xylan in the liquid stream. A slight decrease (~15%) in lignin content after $H_3PO_4$ pretreatment was observed (FIG. 8, stream 3), suggesting that most lignin remained in the solid. After enzymatic hydrolysis, 80% glucan digestibility was achieved for pretreated pine (28.0 g of glucose/100 g dry weight) and 79% (31.2 g of glucose/100 g dry weight) for pretreated Douglas fir (FIG. 8, stream 5). The overall glucose yields were 82% for pine and 80% for Douglas fir (FIG. 8, streams 2 and 5). Moreover, the overall xylose yield was ~90% for both pretreated softwoods. The main barriers to softwood conversion are (1) inter/intramolecular hydrogen bonding networks within cellulose chains that form highly ordered crystalline cellulose and (2) lignin-carbohydrate complex (LCC) linkages (Rollin et al., 2011; Tarasov et al., 2018).

To design and optimize the process for other types of softwood lignocellulose, a more complete understanding of the factors that contribute to high glucan digestibility would be desirable. Accordingly, as described herein below, the morphology and accessibility of cellulose, the cellulose surface functionalities, changes in cellulose crystallinity, and changes in the chemical structure of lignin of pretreated softwoods were analyzed.

Example 6

Fusion Protein Assessment of Morphology and Cellulose

Accessibility of Pretreated Softwoods

Figure 9:
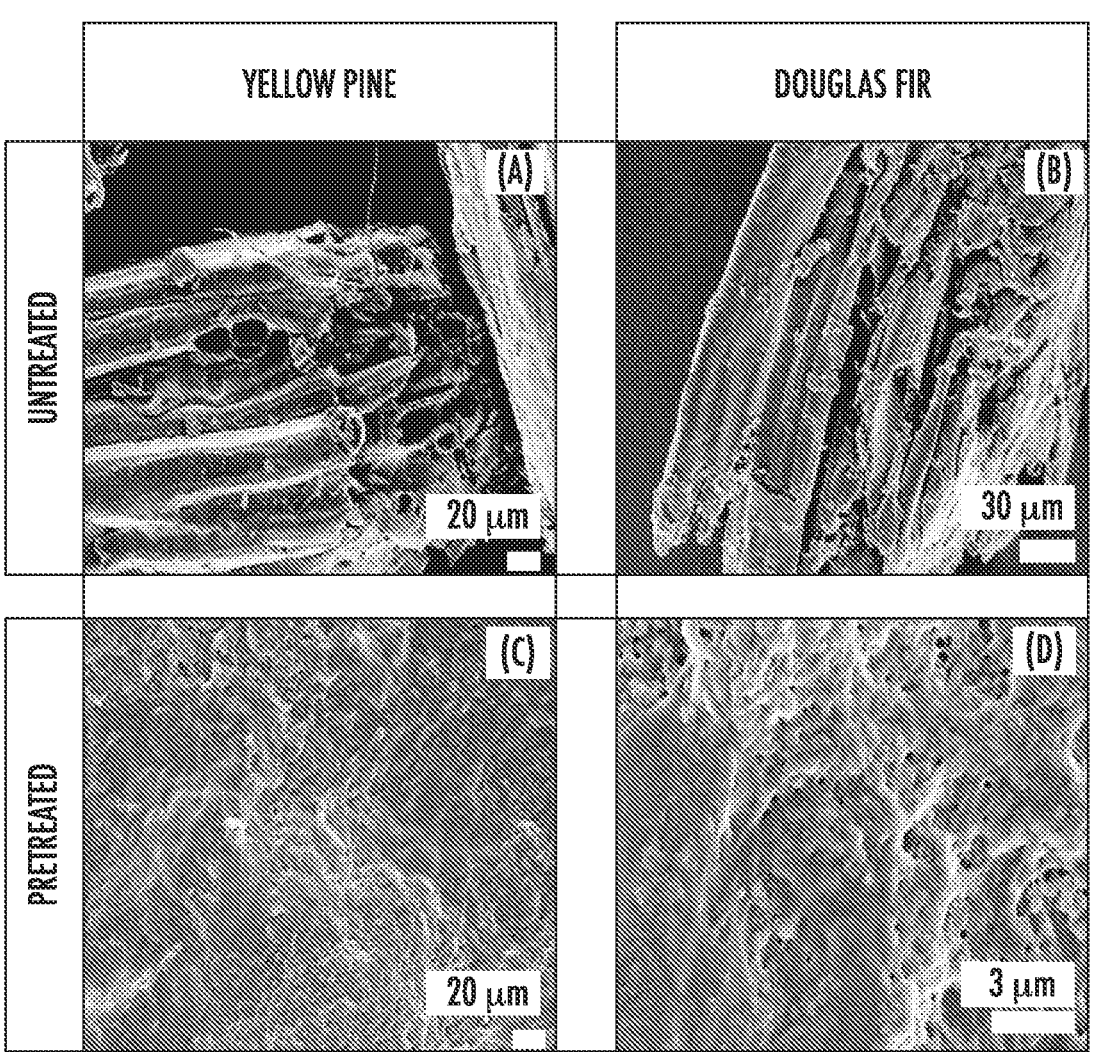
FIG. 9 are SEM micrographs of untreated and pretreated yellow pine (top left and bottom left panels, respectively) and untreated and pretreated Douglas fir (top right and bottom right panels, respectively).

The pretreatment of softwoods disrupted their fibrous structure. (FIG. 9). SEM FIG. 9, top panels shows the clear fibrous structures of untreated pine and Douglas fir, and FIG. 9, bottom panels shows disrupted structures after $H_3PO_4$ pretreatment. Disruption of the fibrous structure may have been due to swelling of the cellulose induced by phosphate ions adding to hydroxyl groups. Phosphate addition would form cellulose phosphate bridges (cellulose-O—$PO_3H_2$; Zhang et al., 2006; Zhang et al., 2009; Kang et al., 2012). These bridges stretch cellulose chains away from each other in the crystalline cellulose, resulting in swelling and disruption of the fibrous structure. The addition of antisolvent (ethanol or water) converted cellulose phosphate to free phosphate and amorphous cellulose (Zhang et al., 2006; Kang et al., 2012), which was more susceptible to enzymatic hydrolysis.

The formation of amorphous cellulose also suggested enhanced surface accessibility. A common method to determine the surface accessibility of materials is the $N_2$ adsorption-desorption technique (Liimatainen et al., 2011; Wiman et al., 2012). For the present purpose, a potential drawback of this technique is that the $N_2$ molecule is small compared with the cellulase enzyme. Hence, $N_2$ adsorption/desorption may overestimate the surface accessibility to enzymes. A more accurate quantitative assay to determine cellulose accessibility to enzymes is based on adsorption of a non-hydrolytic fusion protein (TGC) to the cellulose surface (Hong et al., 2007; Sathitsuksanoh et al., 2013). The TGC protein is 62 kDa, similar in size to *Trichoderma reesei* endo-glucanase I (Zhang & Lynd, 2004; Hong et al., 2007). Moreover, TGC had the cellulose-binding module (CBM) to mimic cellulase adsorption onto cellulose. The green fluorescent protein (GFP) moiety in TGC reports the adsorbed area under fluorescence microscopy. TGC nonspecifically adsorbs onto lignocellulosic biomass (cellulose, hemicellulose, and lignin). Thus, non-specific TGC adsorption was blocked by incubating untreated and pretreated softwoods with bovine serum albumin (BSA), which was allowed to bind onto the non-cellulosic portions of the softwoods. Then TGC could bind to the cellulosic portion. TGC adsorption followed a Langmuir adsorption isotherm and enabled the calculation of cellulose accessibility to cellulase (CAC; Hong et al., 2007). TGC adsorption onto the untreated and pretreated softwoods without BSA blocking enabled calculation of the total substrate accessibility to cellulase (TSAC). Hence, the non-cellulose accessibility to cellulase (NCAC) is calculated from the difference between TSAC and CAC.

Figure 10:
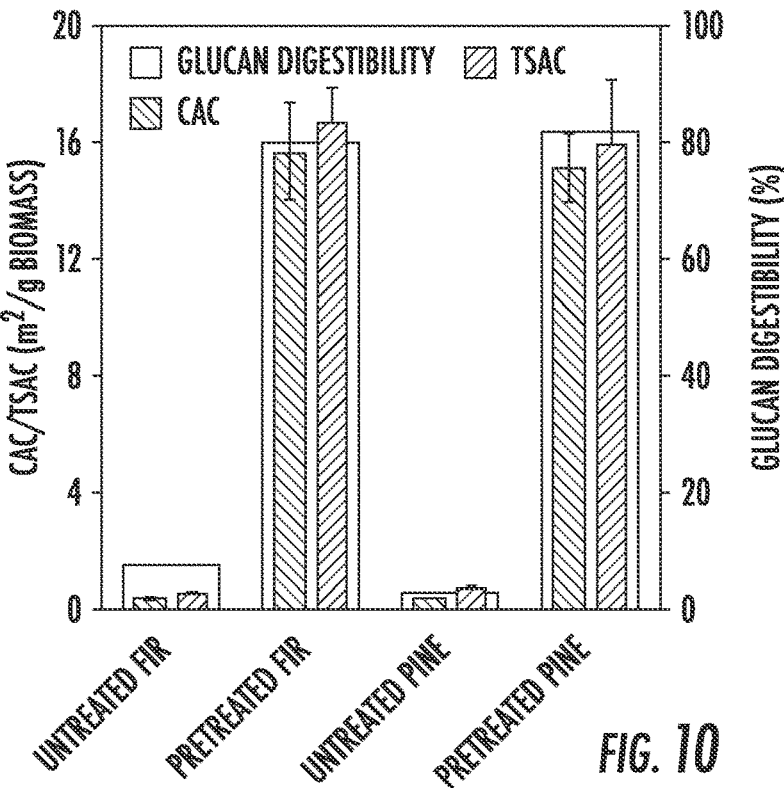
FIG. 10 is a bar graph of Total surface accessibility to cellulase (TSAC; dark gray bars), cellulose accessibility to cellulase (CAC; light gray bars), and glucan digestibility

Untreated Douglas fir had a low TSAC value of ~0.58 $m^2/g$ of biomass and untreated pine had a similarly low value of 0.75 $m^2/g$ of biomass (FIG. 10). The CAC value was 0.40 $m^2/g$ of biomass for Douglas fir and 0.43 $m^2/g$ of biomass for pine. Because TSAC measurement accounted for the non-cellulose accessibility to cellulase (NCAC), the TSAC value of untreated and pretreated softwoods was higher than CAC. After pretreatment, TSAC values increased 27-fold (from 0.6 to 16 $m^2/g$ of biomass) for Douglas fir and 20-fold (0.8 $m^2/g$ of biomass to ~16 $m^2/g$ of biomass) for pine (FIG. 10). Similarly, CAC values increased after pretreatment, ~38-fold (from ~0.4 to 15 $m^2/g$ of biomass) for both Douglas fir and pine. This 38-fold increase in CAC value explains the high susceptibility of pretreated pine and Douglas fir (>80% glucan digestibility) to enzymatic hydrolysis at a low digestibility under 15 FPUs cellulase/g of glucan). These increases in TSAC and CAC also explained the disappearance of the fibrous structure observed in the SEM micrographs after pretreatment.

A high CAC value is important to achieve high glucan digestibility. Typically, untreated biomass has a low CAC value due to the crystalline nature of cellulose, hemicellulose, and lignin (Sathitsuksanoh et al., 2011). After pretreatment, the CAC value increases because of improvement in the accessible surface area from breaking the highly ordered hydrogen bonding of crystalline celluloses and/or removal of hemicellulose/lignin. Thus, the mode of pretreatment is important. Lignin glues plant components together. It was commonly believed that lignin removal would increase the surface accessibility of enzymes to cellulose substrate. Rollin et al. compared two pretreatment techniques that either targeted lignin removal or increased cellulose accessibility (Rollin et al., 2011). They found that increasing cellulose accessibility was more important than lignin removal to achieve a high glucan digestibility. A correlation between CAC and glucan digestibility was also found. An increase in CAC >11 $m^2/g$ biomass from $H_3PO_4$ pretreatment improved glucan digestibility to >80%.

Example 7

Changes in Surface Functionalities of Softwoods after $H_3PO_4$ Pretreatment Pretreatment with $H_3PO_4$ improved cellulose accessibility by converting crystalline cellulose to amorphous cellulose and unwrapping hemicellulose and lignin from the cellulose. This finding was established by FTIR investigation of changes in surface chemical functionality. Normalized FTIR spectra of pine and Douglas fir showed similar bands at 808 (in-phase ring glucomannan), 895 (anomeric vibration at β-glycosidic linkage), 1263 (C—O stretching in guaiacyl ring), 1430 ($CH_2$ bending vibration from cellulose and lignin), 1451 (C—H deformations of lignin), 1507 (aromatic ring stretch in lignin), 1595 (aromatic skeletal vibrations and C═O stretch), and 1730 (ketone/aldehyde C═O stretching; FIG. 11). See also Marchessault & Liang, 1962; Faix, 1992; Fan et al., 2012; Sills & Gossett, 2012. Galactoglucomannan is the principal hemicellulose in softwoods (Brownleader et al., 1997). The hydroxyl groups at the C2- and C3-positions in the backbone units are partly substituted by O-acetyl groups, giving rise to the acetyl group band at 1730 $cm^{-1}$. The vibration mode related to the acetyl groups at 1730 $cm^{-1}$ (Marchessault & Liang, 1962) disappeared after pretreatment, suggesting deacetylation. The disappearance of the acetyl groups corroborated the 70% hemicellulose removal in the mass balance during pretreatment (FIG. 8). The intensity of the in-phase ring glucomannan peak at 808 $cm^{-1}$ was reduced after pretreatment, confirming the removal of hemicelluloses (Marchessault, 1962). Other absorbance regions related to lignin, including (Sannigrahi et al., 2010) in-plane C—H stretch at 1451 $cm^{-1}$ (Faix, 1992) and C—O ring stretches at 1263 $cm^{-1}$, were greatly reduced after $H_3PO_4$ pretreatment (Schultz & Glasser, 1986; Faix, 1992). The band at 1430 $cm^{-1}$ showed the dominant cellulose I region. Cellulose I is the native form of cellulose in plants (Wada et al., 2010; Jia et al., 2013). The band at 895 $cm^{-1}$ showed dominant cellulose II and amorphous cellulose regions. After $H_3PO_4$ pretreatment, the pretreated softwoods showed an intensity reduction of the 1430 $cm^{-1}$ peak and an increase in the intensity of the 895 $cm^{-1}$ peak, indicating that $H_3PO_4$ had disrupted the highly ordered hydrogen bonding in cellulose and converted cellulose I to amorphous cellulose and/or cellulose II. Amorphous cellulose and cellulose II accelerated the overall rate of enzymatic hydrolysis because they are more accessible to enzymes compared with cellulose I (Wada et al., 2010).

These findings coincided with the disappearance of the fibrous structure shown by SEM and an increase in the CAC values after pretreatment. Moreover, hemicellulose and lignin, glued around the cellulose structure, were unwrapped after $H_3PO_4$ pretreatment, corresponding with the reduction of spectral intensities in acetal groups and lignin-carbohydrate linkages. In sum, $H_3PO_4$ pretreatment converted crystalline cellulose to amorphous cellulose by removing hemicellulose and lignin, and improving cellulose accessibility.

Example 8

Changes in the Degree of Crystallinity of Softwoods after $H_3PO_4$ Pretreatment Intra/intermolecular hydrogen bonding within cellulose chains affects its chemical structure and the strength to hold the structure together. Cellulose crystallinity has an important effect on enzymatic hydrolysis. High crystallinity equals low cellulose accessibility by cellulase. Thus, CP/MAS $^{13}C$ NMR was used to determine the crystallinity index (CrI) of untreated and pretreated softwoods. Typically, changes in the $C_4$ region of cellulose are informative with respect to the CrI of cellulose (Sathitsuksanoh & Renneckar, 2017). Changes in the $C_6$ region suggested the breaking of hydrogen bonding between cellulose chains (Park et al., 2009; Park et al., 2010). To establish the baseline, used Avicel (crystalline cellulose) and RAC (amorphous cellulose) were initially used as controls. The Avicel spectrum had doublets at $C_4$ and $C_6$ regions. At the $C_4$ region of Avicel, the peak ~88.90 ppm indicated crystalline cellulose, whereas the peak at ~84.20 ppm indicated amorphous cellulose. The $C_6$ region peak at 65.35 ppm indicated strong hydrogen bonding between cellulose chains. A small shoulder peak at ~62.80 ppm was also observed, indicating disordered contained both crystalline and amorphous cellulose. The RAC spectrum showed a broad peak at the $C_4$ region, suggesting disruption of hydrogen bonding and an amorphous state (compared with Avicel; FIG. 12). The $C_6$ region of RAC showed a disappearance of the peak at 65.35 ppm, causing a peak at 62.80 ppm to become more pronounced. The disappearance of the peak at 65.35 ppm suggested the breaking of hydrogen bonding between cellulose chains and RAC becoming more amorphous. However, it was not possible to determine the CrI of RAC because a crystalline cellulose peak after $H_3PO_4$ pretreatment was not observed (Sathitsuksanoh et al., 2011; Gao et al., 2014). Comparing Avicel with RAC, the difference in the $C_4$ region agreed with the difference in the $C_6$ region, suggesting that dissolving Avicel in 85% $H_3PO_4$ disrupted inter/intramolecular hydrogen bonding within the cellulose structure.

Untreated pine and fir showed doublets at $C_4$ and $C_6$ regions (FIG. 13), suggesting that their cellulosic portion contained both crystalline and amorphous fractions. After pretreatment, the crystalline cellulose peaks at 88.90 and 65.35 ppm of both pine and Douglas fir disappeared, indicating that crystalline cellulose became amorphous. Approximately 18% and 16% decreases in CrI of pine and Douglas fir were observed after $H_3PO_4$ pretreatment. The decrease in CrI of pretreated pine and Douglas fir coincided with FTIR results that crystalline cellulose became more amorphous after $H_3PO_4$ pretreatment. Moreover, untreated pine and fir showed a peak near ~56 ppm, assigned to methoxyl groups in lignin (Sannigrahi et al., 2010), and this peak was observed after pretreatment. These results suggested that $H_3PO_4$ pretreatment did not remove much of the lignin, in agreement with the mass balance calculation that indicated 9-15% lignin removal.

Example 9

2D $^{13}C$-$^1H$ HSQC NMR Spectra of Softwood Samples Before and After Pretreatment To understand changes in the chemical structure of softwood lignins, 2D $^{13}C$-$^1H$ HSQC NMR was employed to characterize their aliphatic (lignin side-chain units; FIG. 14), anomeric (FIG. 15), and aromatic regions pre- and posttreatment (FIG. 16).

The HSQC spectra in the anomeric region of pine and Douglas fir provided information about the configuration and glycosidic linkages between sugar monomeric units (Mansfield et al., 2012). Signals in these spectra are associated with oligosaccharides from cellulose and hemicelluloses. The cellulose peaks were assigned based on previously reported values (Kim et al., 2008; Kim & Ralph, 2014). The internal cellulose unit, (1→4)-β-D-Glcp, ($\delta_C$/$\delta_H$=102.5/4.5 ppm) is the most important cellulosic component of the plant cell wall. The α- and β-anomeric reducing-end correlations of cellulose were well separated from the internal cellulose unit. For example, the α-D-Glcp(R) was at $\delta_C$/$\delta_H$ 92.7/5.2 ppm and β-D-Glcp(R) was at $\delta_C$/$\delta_H$ 97.1/4.44 ppm. In general, reducing end unit crosspeaks were observed in the anomeric region after pretreatment, but the internal cellulose peak became weaker, suggesting cleavage of glycosidic linkages by pretreatment.

In general, the higher frequency of reducing end correlations in the anomeric region suggests depolymerization of carbohydrates. Hence, it was possible to estimate the cellulose degree of polymerization (DP) by integrating the cross-peaks of reducing end units and internal anomeric cellulose (Käldström et al., 2014; Kim & Ralph, 2014). The calculated cellulose DP was ~9 for untreated pine and ~5 for untreated Douglas fir. These low DP values might have been due to the overestimation of reducing end units, and the actual cellulose DP could have been higher (Kim & Ralph, 2014).

The relative change of the cellulose DP was investigated. After pretreatment, the cellulose DP decreased by 62% for pine and by 36% for Douglas fir. These decreases in cellulose DP suggested cleavage of hydrogen bonding. These results also coincided with the pretreatment changes in $C_4$ and $C_6$ regions observed by CP/MAS $^{13}$C NMR (FIG. 13), suggesting that inter/intramolecular hydrogen bonding between cellulose chains was disrupted. The disruption of hydrogen bonding resulted in an increase in cellulase accessibility to cellulose (FIG. 10).

Hemicellulose is another component that was observed in the anomeric region. Softwood hemicellulose is present as galactoglucomannans (Puls, 1997). These galactoglucomannans contain acetyl groups on the $(1\rightarrow4)$-$\beta$-mannosyl units at $C_2$ (2-O—Ac-$\beta$-D-Manp) and $C_3$ (3-O—Ac-$\beta$-D-Manp) positions (Willfor et al., 2008; Kim & Ralph, 2010). Untreated pine and Douglas fir samples showed the cross-peak of 2-O—Ac-Manp ($M_2$), but 3-O—Ac-Manp($M_3$) peak was not observed. The disappearance of the $M_3$ peak might have occurred because it overlapped with the $\beta$-aryl ether (A$\alpha$). The $M_2$ cross-peak became weaker after pretreatment, suggesting that hemicelluloses were removed. These results corroborated the mass balance (FIG. 8), which showed that removal of ~79% of the xylan from pine and 90% from Douglas fir. ~63% mannan was also removed from pine and 66% from Douglas fir.

Lignin linkages of untreated softwoods consisted mainly of $\beta$-aryl ether ($\beta$-O-4 A) with resinol ($\beta$-$\beta$ B) and a trace amount of phenylcoumaran ($\beta$-5 C). Pretreatment weakened the $\beta$-O-4 cross-peak, suggesting that the ether bonds were cleaved and lignin fragments were released. Using semi-quantitative analysis, these cross-peaks were investigated to determine the relative abundance of these lignin linkages (per 100 aromatic units). These calculated values of softwood lignin interunit linkages agreed with previously reported values for softwoods (Sette et al., 2011; Sette et al., 2013; Dutta et al., 2018); Li et al., 2018b. The calculated values of lignin's interunit linkages revealed that $\beta$-O-4 was the most abundant, followed by $\beta$-5 and $\beta$-$\beta$. The pretreated softwoods showed ~45% reduction in $\beta$-O-4 A and a slight increase in $\beta$-5 B, whereas $\beta$-$\beta$ C remained unchanged.

The bond dissociation enthalpy (BDE) of these lignin interunit linkages are in the following order: $BDE_{\beta-O-4}$ (65 kcal/mol)<$BDE_{\beta-\beta}$ (117 kcal/mol)<$BDE_{\beta-5}$ (125 kcal/mol; Parthasarathi et al., 2011). These BDE values agree with the results disclosed herein, showing that the $\beta$-O-4 was easier to be cleaved compared with $\beta$-5 and $\beta$-$\beta$. After pretreatment, a significant decrease in relative abundance of $\beta$-O-4 and maintenance of the $\beta$-5 and $\beta$-$\beta$ similar to those of untreated softwoods suggested that lignin depolymerization was the dominant reaction as evidenced by a great decrease in the $\beta$-O-4 A with minimal carbon-carbon linkage degradation reaction (breaking $\beta$-$\beta$ C) and condensation reaction (formation of $\beta$-5 B; Wen et al., 2013). The residual lignin from this pretreatment was depolymerized with minimal formation of C—C bonds, an outcome that provides the opportunity to upgrade the resulting lignin into high-value products (aromatic chemicals, battery components, and carbon fibers; Liu et al., 2018; Hossain et al., 2019) and to make this process economically viable (Alonso et al., 2017).

Lignin has three aromatic units: syringyl (S) unit, guaiacyl (G) unit, and p-hydroxyphenyl (H) unit. The aromatic region of untreated pine and Douglas fir showed that both contained only guaiacyl (G) units, which was a signature of softwoods (Shuai, 2010). Examination of the aromatic region (FIG. 16) demonstrated that pretreated softwoods did not show any change in the signals of major aromatic units compared to that of untreated softwoods. After ionic liquid pretreatment of pine, the condensed lignin structure has shown C—H correlations between the 2- and 6-positions (G2-condensed structure at $\delta_C/\delta_H$ 112.5/6.65 ppm and G6-condensed structure at $\delta_C/\delta_H$ 120.5/6.55 ppm) of the guaiacyl units and the 5-position of other lignin side chains (Torr et al., 2012; Wang et al., 2017). These G2- and G6-condensed structures were absent from the aromatic region of the pretreated softwoods, which was consistent with the maintenance of the $\beta$-5 and $\beta$-$\beta$ linkages in the aliphatic region after pretreatment. These results suggested that, although $H_3PO_4$ pretreatment could hydrolyze lignin's $\beta$-aryl ether linkages into small lignin fragments, the remaining lignin in pretreated samples was not modified and/or condensed. Note that, by the 2D HSQC NMR technique, C5-substituted condensed phenolic compounds (5-5' linkage; Xu & Ferdosian, 2017) were not observed because C—H bonds did not exist in the 5-5' linkages.

The presently disclosed $H_3PO_4$ pretreatment process can also be applied to a variety of lignocellulosic feedstocks at a mild reaction temperature (e.g., 50° C.) and atmospheric pressure, including agricultural waste, bioenergy crops, and woody biomass (hardwoods and softwoods). $H_3PO_4$ pretreatment improved cellulose accessibility to cellulase, resulting in a high glucan digestibility of ~80-100% with a low enzyme loading of 5 FPUs/g glucan (FIG. 17; Sathitsuksanoh et al., 2012a). This process was biomass species-independent. Its mild reaction condition, high sugar yield at a low enzyme loading, and preservation of lignin will have a great impact on the economic viability of biorefineries.

Discussion of Examples 4-9

$H_3PO_4$ pretreatment of pine and Douglas fir at low temperature (50° C.) and atmospheric pressure is described herein. This process showed a low severity factor (0.91) and E-factor (168.9) compared with other pretreatment processes. After 48 hours, a high glucan digestibility of 78% for pine and 80% for Douglas fir was achieved, even at a low enzyme loading of 5 FPUs/g glucan. $H_3PO_4$ pretreatment produced cellulose accessibility to cellulase (CAC) values higher than the 11 m$^2$/g threshold, yielding >78% glucan digestibility at a low enzyme loading (5 FPU/g glucan). Examination of pretreated softwoods by CP/MAS, $^{13}$C NMR, and FTIR revealed breaking of the orderly hydrogen bonding of crystalline cellulose, which was responsible for an enhanced CAC value. The process was feedstock-independent. NMR revealed that lignin was depolymerized without being condensed, providing the opportunity to upgrade the pretreated lignin to value-added chemicals. In summary, the presently disclosed $H_3PO_4$ pretreatment process provides mild reaction conditions, high sugar yields at a low enzyme loading, and preservation of lignin.

REFERENCES

All references cited in the instant disclosure, including but not limited to all patents, patent applications and publications thereof, scientific journal articles, and database entries (and all annotations available therein) are incorporated herein by reference in their entireties to the extent that they supplement, explain, provide a background for, or teach methodology, techniques, and/or compositions employed herein.

Abels et al. (2012) J. Membr. Sci. 405-406:1-10.

Agency, U.S.E.P. Inventory of U.S. Greenhouse Gas Emissions and Sinks: 1990-2015. https://www.epa.gov/ghgemissions/inventoryus-greenhouse-gas-emissions-and-sinks-1990-2015 (accessed Aug. 1, 2019).

Ahn et al. (2016) Phys. Chem. Chem. Phys. 18: 460-1469.

Alonso et al. (2017) Sci. Adv. 3(5):No. e1603301.

Alvarez et al. (2016) Microb Biotechnol 9(2):149-156.

Alvarez-Vasco & Zhang (2013) Bioresour Technol 150:321-327.

Amarasekara & Wiredu (2011) Ind. Eng. Chem. Res. 50(21): 12276-12280.

Amin et al. (2010) Hydrometallurgy 105(1):115-119.

Andre et al. (2016) Front. Plant Sci. 7:19.

Anwar et al. (2014) J Radiat Res Appl Sci 7(2):163-173.

Asdrubali (2006) In Survey on the acoustical properties of new sustainable materials for noise control, Proceedings of Euronoise.

Ash (1948) Economic Botany 2(2):158-169.

Assuncao et al. (2017) RSC Adv. 7(12):6922-6930.

Barberà et al. (2011) Industrial Crops and Products 34(1): 865-872.

Barta et al. (2010) Chemical and Biochemical Engineering Quarterly 24(3):331-339.

Binder & Raines (2009) JACS 131(5):1979-1985.

Binder & Raines (2010) Proc Natl Acad Sci USA 107(10): 4516-4521.

Binder et al. (2010) Energy Environ. Sci. 3:765-771.

Biswas et al. (2015) Bioresour. Technol. 192:46-53.

Blanchard & Brennecke (2001) Ind. Eng. Chem. Res. 40:287-292.

Bozell et al. (2000) Resour. Conserv. Recycl. 28:227-239.

Braden et al. (2011) Green Chemistry 13(7):1755-1765.

Brady (2003) San Joaquin Agric. L. Rec. 13:85-108.

Brandt et al. (2015) Green Chem. 17(11):5019-5034.

Brouwer et al. (2017) September Purif. Technol. 185:186-195.

Brownleader et al. (1997) 3-Carbohydrate Metabolism: Primary Metabolism of Monosaccharides. *In Plant Biochemistry*, Dey & Harborne (eds.) Academic Press: London. pp. 111-141.

Cao et al. (2010) J. Appl. Polym. Sci. 116(1):547-554.

Cao et al. (2014) Applied Catalysis A: General 481:49-53.

Chakar & Ragauskas (2004) Ind. Crops Prod. 20:131-141.

Chang et al. (2007) Bioresour. Technol. 98:1448-1453.

Chen et al. (2012) J. Chem. Technol. Biotechnol. 87:1634-1640.

Chen et al. (2018) Molecules 2018, 23 (3), 529.

Cheng et al. (2013) Anal. Chem. 85(6):3213-3221.

Chio et al. (2019) Renewable Sustainable Energy Rev. 107:232-249.

Choudhary et al. (2013) J. Am. Chem. Soc. 135:3997-4006.

Christensen et al. (2011) Energy & Fuels 25(11):5422-5428.

Cleveland & Morris (2014) C. Section 45—Climate Change. In Handbook of Energy. Cleveland & Morris (eds), Elsevier: Boston, Massachusetts United States of America. pp. 805-820.

Colom et al. (2003) Polymer Degradation and Stability 80(3):543-549.

Constant et al. (2016) Green Chem. 18(9):2651-2665.

Davison et al. (2006) Appl. Biochem. Biotechnol. 130(1-3): 427-435.

Dee & Bell (2011) ChemSusChem 4(8):1166-1173.

Deitch (2003) *Hemp: American history revisited: the plant with a divided history*. Algora Publishing.

Devinsky et al. (2014) Epilepsia 55(6):791-802.

Duchemin et al. (2009) Composites Part A 40(12):2031-2037.

Dutta et al. (2018) ACS Sustainable Chem. Eng. 6(3):3079-3090.

Edenhofer (2014) *Climate change* 2014: *Mitigation of Climate Change*, Cambridge University Press, Vol. 3.

Edens 2005) *Polysaccharides: Structural Diversity and Functional Versatility, 2nd ed.* Edited by Severian Dumitriu (University of Sherbrooke, Quebec). Marcel Dekker: New York.

Ehrensing (1998) Feasibility of industrial hemp production in the United States Pacific Northwest; Corvallis, Or.: Agricultural Experiment Station, Oregon State University.

Enslow & Bell. (2015) Catal. Sci. Technol. 5:2839-2847.

Ewanick et al. (2007) Biotechnol. Bioeng. 98(4):737-746.

Faix (1992) Fourier Transform Infrared Spectroscopy. In *Methods in Lignin Chemistry*. Lin & Dence (eds.), Springer: Berlin, pp. 83-109.

Fan et al. (2012) Fourier transform infrared spectroscopy for natural fibres. In *Fourier Transform-Materials Analysis*, InTech.

Fang & Hanna (2002) Bioresour. Technol. 81:187-192.

Fathead Minnow Hazardous Waste Screen Bioassay, Contract Report No. 1219186; BC Laboratories Inc. Bakersfield, California, USA.

Ferrer et al. (2008) Plant Physiol. Biochem. 46(3):356-370.

Fitzpatrick (1997) Production of Levulinic Acid from Carbohydrate-Containing Materials. U.S. Pat. No. 5,608,105.

Frey et al. (2015) Method for producing levulinic acid from lignocellulosic biomass. U.S. Patent Application Publication No. 2015/0052806.

Fujii et al. (2009) Biotechnol. Biotechnol. Biofuels 2(1):24.

Funaoka et al. (1990) Wood Sci. Technol. 24(3):277-288.

Gao et al. (2014) Biotechnol. Biofuels 7(1):24-24.

Girisuta et al. (2006) Chemical Engineering Research and Design 84(5):339-349.

Girisuta et al. (2008) Bioresour. Technol. 99:8367-8375.

Gschwend et al. (2019) Green Chem 21(3):692-703.

Gupta & Jiang (2015) Chem. Eng. Sci. 121:180-189.

Ha et al. (2010) J. Chromatogr. A 1217:7638-7641.

Hall et al. (2010) FEBS J 2010:277(6):1571-1582.

Hayes et al. (2006) *The Biofine Process-production of Levulinic Acid, Furfural, and Formic Acid from Lignocellulosic Feedstocks*. pp. 139-164.

Heikkinen et al. (2003) J. Am. Chem. Soc. 125(14):4362-4367.

Heinze et al. (2005) Macromol. Biosci. 5:520-525.

Hewetson et al. (2016) Energy Fuels 30(11):9975-9977.

Hong et al. (2007) Langmuir 23(25):12535-12540.

Hong et al. (2008) Anal. Chim. Acta 621(2):193-199.

Horvat et al. (1985) Tetrahedron Letters 26(17):2111-2114.

Hossain et al. (2019) Appl. Catal, A 582:117100.

Hsu & Bates (1964) Mineral. Mag 33(264):749-768.

Hu et al. (2017) Chemical Communications 53(20):2938-2941.

Jia et al. (2013) J. Agric. Food Chem. 61(50):12405-12414.

Jia et al. (2013) Journal of Agricultural and Food Chemistry 61(50):12405-12414.

Jin et al. (2017) Biotechnol. Bioeng. 114:980-989.

John. 1.2 Billion Vehicles On World's Roads Now: 2 Billion By 2035: Report. https://www.greencarreports.com/news/1093560_1-2-billion-vehicles-on-worlds-roads-now-2-billion-by-2035-report (accessed 3 Jun. 2019).

Käldström et al. (2014) Green Chem. 16(7):3528-3538.

Kang et al. (2012) Carbohydr. Polym. 90(4):1771-1778.

Kang et al. (2018) Energy Fuels 32:3526-3531.

Khan et al. (2015) J. Appl. Polym. Sci. 132:1-6.

Kim & Kim (2018) Front. Energy Res. 6: No. 92.

Kim & Ralph (2010) Org. Biomol. Chem. 8(3):576-591.

Kim & Ralph (2014) RSC Adv. 4(15):7549-7560.

Kim et al. (2008) BioEnergy Res. 1(1):56-66.

Kim et al. (2012) September Purif. Technol. 90:64-68.

Kishimoto et al. (2010) J Agric Food Chem 58(2):895-901.

Klein-Marcuschamer et al. (2010) Biomass Bioenergy 34(12):1914-1921.

Klein-Marcuschamer et al. (2011) Biofuels: Bioprod. Biorefin. 5:562.

Kobayashi & Manabe (2002) Acc. Chem. Res. 35:209-217.

Kreuger et al. (2011) Bioresource Technology 102(3):3457-3465.

Leizer et al. (2000) Journal of Nutraceuticals, Functional & Medical Foods 2(4):35-53.

Li et al. (2007) Bioresour. Technol. 98:3061-3068.

Li et al. (2009) Bioresour. Technol. 100(13):3245-3251.

Li et al. (2018a) ChemCatChem 10:4084-4089.

Li et al. (2018b) Green Chem. 20(18):4224-4235.

Li et al. (2018c) Chem. Sci. 9:4027-4043.

Licursi et al. (2018) Bioresour. Technol. 264:180-189.

Liimatainen et al. (2011) Carbohydr. Polym. 83(4):2005-2010.

Liu & Chen (2008) Phosphorus Cycle. In Encyclopedia of Ecology. Jorgensen & Fath (eds.) Academic Press: Oxford, pp. 2715-2724.

Liu et al. (2018) ACS Sustainable Chem. Eng. 6(9):12251-12260.

Lu et al. (2010) Appl. Biochem. Biotechnol. 160:360-369.

Mabee et al. (2006) Appl. Biochem. Biotechnol. 129:55-70.

Mansfield et al. (2012) Nat. Protoc. 7(9):1579-1589.

Marchessault & Liang (1962) J. Polym. Sci. 59(168):357-378.

Marchessault (1962) Pure Appl. Chem. 5(1-2):107-130.

McDonald et al. (2017) System and method for treatment of biomass for the production of biofuels and biochemicals. WHO 2017.

Mes-Hartree & Saddler (1983) Biotechnol Lett 5(8):531-536.

Miyata & Miyafuji (2014) J. Wood Sci. 60:438-445.

Morone et al. (2015) Renewable and Sustainable Energy Reviews 51(Suppl C):548-565.

Mostofian et al. (2014) Cellulose 21:983-997.

Motagamwala et al. (2019) Energy Environ. Sci. 12:2212-2222.

Moxley et al. (2008) J. Agric. Food Chem. 56(17):7885-7890.

Muranaka et al. (2014) Ind. Eng. Chem. Res. 53:11611-11621.

Nair et al. (2017) J. Chem. Technol. Biotechnol. 92(6):1256-1265.

Nakagame et al. (2011) Bioresour. Technol. 102(6):4507-17.

Nelson & O'Connor (1964) Journal of Applied Polymer Science 8(3):1311-1324.

Nguyen et al. (2000) Appl Biochem Biotechnol 84-86:561-576.

Nhien et al. (2016) Ind. Eng. Chem. Res. 55:5180-5189.

Nitsos et al. (2016) ACS Sustainable Chem Eng 4(9):4529-4544.

Nitsos et al. (2018) Energies 11(1):50.

Normark et al. (2014) BMC Biotechnol 14(1):20.

Ohno & Miyafuji (2013) J. Wood Sci. 59:221-228.

Overend et al. (1987) Philos. Trans. R. Soc., A 321(1561):523-536.

Pan et al. (2004) Appl. Biochem. Biotechnol. 115(1-3):1103-1114.

Pang et al. (2016) Bioresour. Technol. 214:96-101.

Park et al. (2009) Cellulose 16(4):641-647.

Park et al. (2010) Biotechnol. Biofuels 3:10-10.

Parthasarathi et al. (2011) J. Phys. Chem. Lett. 2(20):2660-2666.

Patil et al. (2012) Energy Fuels 26:5281-5293.

Peleteiro et al. (2014) J Cleaner Prod 76:200-203.

Perlack (2005) Biomass as feedstock for a bioenergy and bioproducts industry: the technical feasibility of a billion-ton annual supply; Oak Ridge National Laboratory: Oak Ridge, Tennessee, United States of America.

Pielhop et al. (2016) Biotechnol Biofuels 9(1):152.

Pileidis & Titirici (2016) ChemSusChem 9(6):562-582.

Puls (1997) Macromol. Symp, Wiley Online Library: Weinheim, Germany. pp. 183-196.

Rabideau et al. (2014) J. Phys. Chem. B 118(6):1621-1629.

Rackemann & Doherty (2011) Biofuels, Bioprod. Biorefin. 5(2):198-214.

Rackley (2017) Carbon capture from power generation. In Carbon Capture and Storage, 2nd ed., Rackley (ed) Butterworth-Heinemann: Boston, Massachusetts, United States of America. pp. 75-101.

Rajan & Carrier (2014) Biomass Bioenergy 62:222-227.

Rana et al. (2012) Bioresour. Technol. 121:61-67.

Ranalli & Venturi (2004) Euphytica 140(1):1-6.

Remsing et al. (2006) Chem. Commun. 71:1271-1273.

Rinaldi & Schüth (2009) ChemSusChem 2(12):1096-1107.

Rinaldi et al. (2016) Angew. Chem. Int. Ed. 55(29):8164-8215.

Robinson (1996) *The Great Book of HEMP: The Complete Guide to the Environmental, Commercial. and Medicinal Uses of the World's Most Extraordinary Plant*, Inner Traditions/Bear & Co.

Rollin et al. (2011) Biotechnol. Bioeng. 108(1):22-30.

Runge & Zhang (2012) Ind. Eng. Chem. Res. 51:3265-3270.

Samuel et al. (2011) Polym. Degrad. Stab. 96:2002-2009.

Sannigrahi et al. (2010) Carbohydr. Res. 345(7):965-970.

Satari et al. (2019) Sustain. Energy Fuels 3(1):11-62.

Sathitsuksanoh & Renneckar (2017) Characterization Methods and Techniques. In *Introduction to Renewable Biomaterials: First Principles and Concepts*. Ayoub & Lucia (eds.), Wiley, Weinheim, Germany. pp. 107-140.

Sathitsuksanoh et al (2009) Ind. Eng. Chem. Res. 48(13):6441-6447.

Sathitsuksanoh et al. (2011) Biotechnol. Bioeng. 108(3):521-529.

Sathitsuksanoh et al. (2012a) Bioresour. Technol. 117:228-233.

Sathitsuksanoh et al. (2012b) Cellulose 19(4):1161-1172.

Sathitsuksanoh et al. (2013) J. Chem. Technol. Biotechnol. 88(2):169-180.

Sathitsuksanoh et al. (2014) Green Chem. 16(3):1236-1247.

Sathitsuksanoh et al. (2015) BioEnergy Res. 8(3):973-981.

Schafer et al. (2001) Chem. Commun. 17:1622-1623.

Schultz & Glasser (1986) Holzforschung 40:37-44.

Schutyser et al. (2018) Chem. Soc. Rev. 47:852-908.

Segal et al. (1959) Text. Res. J. 29(10):786.

Serrano-Ruiz et al. (2010) Green Chemistry 12(4):574-577.

Sette et al. (2011) Chem.—Eur. J 17(34):9529-9535.

Sette et al. (2013) Comput. Struct. Biotechnol. J. 6(7):1-7.

Sheldon & Sanders (2015) Catal. Today 239:3-6.
Sheldon (2007) Green Chem. 9(12):1273-1283.
Sheldon (2017) Green Chem. 19(1):18-43.
Shen & Wyman (2012) AIChE J. 58(1):236-246.
Shuai (2010) Bioresour Technol 101:3106-3114.
Sills & Gossett (2012) Biotechnol. Bioeng. 109(2):353-362.
Sipos et al. (2009) Appl Biochem Biotechnol 153(1-3):151-162.
Sipos et al. (2010) Biomass and Bioenergy 34(12):1721-1731.
Siripong et al. (2016) Bioresour. Technol. 203:303-308.
Sluiter et al. (2008) Determination of ash in biomass. Laboratory Analytical Procedure (LAP). Technical Report, 1-5 NREL/TP-510-42622.
Sluiter et al. (2010) J. Agric. Food. Chem. 58:9043-9053.
Sluiter et al. (2011) Determination of structural carbohydrates and lignin in biomass. Laboratory Analytical Procedure (LAP). Technical Report, NREL/TP-510-42618.
Soderstrom et al. (2002) Appl Biochem Biotechnol 98-100:5-21.
Son et al. (2012) Reaction Kinetics, Mechanisms and Catalysis 106(1):185-192.
Ståhlberg et al. (2010) Green Chem. 12:321-325.
Stevanovic (2016) Chemical Composition and Properties of Wood. Lignocellulosic Fibers and Wood Handbook. 49.
Sun et al. (2009) Green Chemistry 11(5):646-655.
Sun et al. (2013) Biotechnology for Biofuels 6(1):39.
Sun et al. (2015) Bioresour. Technol. 186:200-206.
Sun et al. (2018) Chem Rev 118(2): 614-678.
Swatloski et al. (2002) J. Am. Chem. Soc. 124(18):4974-4975.
Swift et al. (2015) Green Chem. 17(10):4725-4735.
Swift et al. (2016) J. Catal. 333:149-161.
SzijártÓ et al. (2008) J Biotechnol 136(3):140-147.
Takada et al. (2019) Biotechnol. Bioeng. 116(11):2864-2873.
Tarasov et al. (2018) Biotechnol. Biofuels 2018:11:269-269.
Taylor et al. (2010) Phys. Chem. Chem. Phys. 12:1772-1783.
Torr et al. (2012) Green Chem. 14(3):778-787.
Trinh et al. (2015) Biomass Bioenergy 81:1-8.
Tuercke et al. (2009) Chem. Eng. Technol. 32:1815-1822.
U.S. Patent Application Publication Nos. 2015/0052806, 2017/0190682, 2017/0183322.
U.S. Pat. Nos. 5,608,105; 5,916,780; 8,663,392; 9,346,730; 9,663,835.
van der Werf & Turunen (2008) Industrial Crops and Products 27(1):1-10.
van Zandvoort et al. (2013) ChemSusChem 6:1745-1758.
Vanoye et al. (2009) Green Chem. 11:390-396.
Vogl et al. (2004) Journal of Industrial Hemp 9(1):51-68.
VoteHemp 2016 Annual Retail Sales for Hemp Products Estimated at $688 Million. http://www.votehemp.com/PR/2017-4-14_2016_Annual-Retail-Sales-for-Hemp-Products-Estimated-at-$688 Million.html (accessed Apr. 14, 2017).
VoteHemp. U. S. HEMP CROP REPORT. https://www.votehemp.com/u-s-hemp-crop-report. (accessed Oct. 10, 2019).
Wada et al. (2010) Polym. Degrad. Stab. 95(4):543-548.
Wagner et al. (2015) Proc Natl Acad Sci USA 112(19):6218.
Wang et al. (2012) Top. Catal. 55:657-662.
Wang et al. (2016) Green Chemistry 18(5):1218-1223.
Wang et al. (2017) Sci. Rep. 7(1):593.
Weingarten et al. (2012) Energy Environ. Sci. 5:7559-7574.
Weingarten et al. (2013) J. Catal. 304:123-134.
Weiqi & Shubin (2017) Chem. Eng. J. 307:389-398.
Wen et al. (2013) Bioresour. Technol. 150:278-286.
Willfor et al. (2008) Carbohydr. Polym. 72(2):197-210.
Wiman et al. (2012) Bioresour. Technol. 126:208-215.
Windom et al. (2011) Energy & Fuels 25(4):1878-1890.
Wright et al. (2012) ChemSusChem 5(9):1657-1667.
Wu et al. (2018) Bioresour. Technol. 251:171-180.
Xin et al. (2017) RSC Adv. 7:41546-41551.
Xu & Ferdosian (2017) Conversion of lignin into bio-based chemicals and materials. Springer, Berlin.
Xu et al. (2010) Green Chem. 12:268-275.
Xu et al. (2019) ACS Appl. Energy Mater. 2:6979-6983.
Yang & Wyman (2008) Biofuels Bioprod Biorefin 2(1):26-40.
Yang et al. (2002) Biotechnol. Bioeng. 77(6):678-84.
Yelle et al. (2008) Magn. Reson. Chem. 46(6):508-517.
Yi et al. (2020) Fuel 259: No. 116208.
Yoon et al. (2014) Energy 77:19-24.
Yu et al. (2019) Bioresour. Technol. 282:69-74.
Zeke. State of the climate: 2018 set to be fourth warmest year despite cooler start. https://www.carbonbrief.org/state-of-theclimate-2018-set-to-be-fourth-warmest-year-despite-cooler-start (accessed Jul. 19, 2019).
Zhang & Lynd (2004) Biotechnol. Bioeng. 88:797-824.
Zhang et al. (2006) Biomacromolecules 7(2):644-648.
Zhang et al. (2009) Molecules 14(12):5027-5041.
Zhang et al. (2015) J. Nanomater. 2015:6.
Zhang et al. (2016) ACS Sustainable Chem Eng 4(12):6618-6628.
Zhang et al. (2019) Ind. Crops Prod. 133:241-249.
Zhao et al. (2007) Science 316:1597-1600.
Zhao et al. (2009) J. Biotechnol. 139:47-54.
Zheng et al. (2018) Ind. Eng. Chem. Res. 57:8518-8528.
Zhu et al. (2009) Biotechnol. Bioeng. 103(4):715-724.
Zhu et al. (2011) Bioresour. Technol. 102:8921-8929.
Ziebell et al. (2010) J. Biol. Chem. 285(50):38961-38968.

It will be understood that various details of the presently disclosed subject matter can be changed without departing from the scope of the presently disclosed subject matter. Furthermore, the foregoing description is for the purpose of illustration only, and not for the purpose of limitation.

What is claimed:

1. A method for producing levulinic acid from lignocellulosic biomass of hemp hurds in a singular reaction vessel, the method comprising:

(a) dissolving lignocellulosic biomass of hemp hurds in an amount of greater than 15 wt % in an ionic liquid medium to produce a cellulose-rich product in a reaction vessel;

hydrolyzing cellulose present in the cellulose-rich product to produce a glucose-(b) rich product in the reaction vessel of a);

(c) adding a phosphoric acid pretreated softwood into the vessel comprising the hydrolyzed product of b);

(d) dehydrating glucose from the glucose-rich product of c), and/or dehydrating fructose from isomerization of the glucose of c), to produce 5-hydroxymethyl furfural (HMF) in the reaction vessel of a); and (e) hydrolyzing the HMF to levulinic acid in the reaction vessel of a).

2. The method of claim 1, wherein the ionic liquid medium comprises:

a first component selected from the group consisting of 1-ethyl-3-methylimidazolium chloride ([$C_2C_1$im] Cl), 1-butyl-3-methylimidazolium chloride, 1-butyl-3-methylimidazolium hexafluorophosphate, 1-butyl-3-methylimidazolium acetate, 1-butyl-1-methylpyrrolidinium chloride, 1-butyl-3-methylimidazolium methylsulfate, N,N-dimethylethanolamonium hydrogen sulfate, N,N-dimethylethanolamonium acetate, N,N-dimethylethanolamonium glycolate, N,N-dimethylethanolammonium succinate, 1-ethyl-3-methylimidazolium acetate, 1-ethyl-3-methylimidazolium diethyl phosphate, 1-ethyl-3-methylimidazolium chloride, 1,3-dimethylimidazolium dimethyl phosphate, Cholinium glycinate, and Cholinium lysinate; and optionally a second component comprising an acid selected from the group consisting of hydrochloric acid, sulfuric acid, nitric acid, trifluoroacetic acid, and phosphoric acid.

3. The method of claim 2, wherein the second component is present in the ionic liquid medium at about a 0.1 acid/biomass weight ratio.

4. The method of claim 2, wherein the ionic liquid medium comprises $[C_2C_1im]Cl$ and hydrochloric acid (HCl) at about a 0.1 HCl/Biomass weight ratio.

5. The method of claim 1, wherein the dissolving occurs at a temperature of about 140° C. to about 200° C. and/or for time of about 60 minutes to about 360 minutes.

6. The method of claim 5, wherein dissolving occurs at a temperature of about 150° C. to about 175° C. and/or for time of about 60 minutes to about 120 minutes.

7. The method of claim 1, wherein the hydrolyzing of the cellulose-rich product occurs at a temperature of about 95° C. to about 125° C. for about two hours or occurs at about 95° C. for about 1 hour to about 6 hours and provides a yield of at least 25% glucose or occurs at a temperature of about 95° C. to about 120° C. for about two hours or occurs at about 95° C. for at least 2 hours and provides a yield of at least 40% glucose.

8. The method of claim 1, wherein the hydrolyzing of the cellulose-rich product is performed in the presence of an acid catalyst, optionally wherein the acid catalyst comprises a Lewis acid.

9. The method of claim 8, wherein the Lewis acid is selected from $CrCl_3 \cdot 6H_2O$, $AlCl_3 \cdot 6H_2O$, $ZrCl_4$, $SnCl_2$, $HfCl_4$, or $SnCl_4 \cdot 5H_2O$.

10. The method of claim 1, wherein the loading of lignocellulosic biomass of hemp hurds is about 15 wt % to about 25 wt %.

11. The method of claim 1, wherein the softwood is pretreated with phosphoric acid at a temperature from about 20° C. to about 180° C., or for about 0.1 hours to about 24 hours, or both the temperature and the time.

12. The method of claim 1, further comprising treating the phosphoric acid pre-treated softwood with an enzyme after the softwood is pretreated to hydrolyze the phosphoric acid pre-treated softwood, wherein the enzyme is cellulase, hemicellulase, β-glucosidase, or a combination thereof for a time and at a temperature sufficient to hydrolyze the glucan present in the pre-treated softwood.

13. The method of claim 12, wherein the enzyme combination is a mixture of cellulase and hemicellulase, optionally at a ratio of about 9:1 by weight.

14. The method of claim 12, wherein the enzyme combination comprises about 5 FPUs of cellulase and 10 units of β-glucosidase per gram of glucan, or the enzyme combination comprises about 15 FPUs of cellulase and 30 units of β-glucosidase per gram of glucan.

15. A method for producing levulinic acid from lignocellulosic biomass of hemp hurds in a singular reaction vessel, the method comprising:

(a) dissolving greater than 15 wt % of lignocellulosic biomass of hemp hurds in an ionic liquid medium at a temperature of about 140° C. to about 200° C. and/or for time of about 60 minutes to about 360 minutes to produce a cellulose-rich product in a reaction vessel;

(b) hydrolyzing cellulose in the cellulose-rich product at a temperature of about 95° C. to about 125° C. for about 1 hour to about 6 hours in the presence of an acid catalyst, to produce a glucose-rich product in the reaction vessel of a);

(c) adding a phosphoric acid pretreated softwood into the vessel comprising the hydrolyzed product of b);

(d) dehydrating glucose from the glucose-rich product of c), and/or dehydrating fructose from isomerization of the glucose of c), to produce 5-hydroxymethyl furfural (HMF) in the reaction vessel of a); and (e) hydrolyzing the HMF to levulinic acid in the reaction vessel of a).

* * * * *